US012667704B2

(12) United States Patent (10) Patent No.: US 12,667,704 B2
Nitzan et al. (45) Date of Patent: Jun. 30, 2026

(54) DEVICES AND METHODS FOR TREATING EDEMA

(71) Applicant: White Swell Medical Ltd, Kibbutz Shefayim (IL)

(72) Inventors: Yaacov Nitzan, Hertzelia (IL); Ronan Keating, Galway (IE); Shahaf Marmur, Tel Aviv (IL); Or Inbar, Tel-Aviv (IL); Eamon Brady, Galway (IE); Gerry McCaffrey, Galway (IE); Reed Williston, Galway (IE); Sagi Raz, Tel-Aviv (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 0 days.

(21) Appl. No.: 18/138,407

(22) Filed: Apr. 24, 2023

(65) Prior Publication Data

US 2023/0347113 A1 Nov. 2, 2023

Related U.S. Application Data

(63) Continuation of application No. 16/801,994, filed on Feb. 26, 2020, now Pat. No. 11,660,426.
(Continued)

(51) Int. Cl.
*A61M 60/237* (2021.01)
*A61M 25/10* (2013.01)

(52) U.S. Cl.
CPC ........ *A61M 25/1018* (2013.01); *A61M 25/10* (2013.01); *A61M 60/237* (2021.01);
(Continued)

(58) Field of Classification Search
CPC .............. A61M 25/1018; A61M 25/10; A61M 2025/1022; A61M 2025/3334;
(Continued)

(56) References Cited

U.S. PATENT DOCUMENTS 3,211,150 A   10/1965   Foderick
3,884,240 A   5/1975   Gilman
(Continued)

FOREIGN PATENT DOCUMENTS

AU      2018203640 A1   6/2018
CA         2250993 A1   10/1997
(Continued)

OTHER PUBLICATIONS

Canadian Exam Report issued in Canadian Application No. 3042153, date of mailing: Apr. 15, 2024, 6 pages.
(Continued)

*Primary Examiner* — George R Evanisko
(74) *Attorney, Agent, or Firm* — Brown Rudnick LLP; Adam M. Schoen

(57) ABSTRACT

The disclosure relates to devices and methods for the treatment of edema that uses an impeller with a balloon that may be mounted on the impeller housing. The invention provides devices and methods for treatment of edema that use an indwelling catheter with an impeller to lower pressure at an outlet of a lymphatic duct and a balloon on the impeller to guide and to restrict blood flow. The balloon restricts return flow from the jugular and guides that flow into the impeller cage. By funneling the flow into the impeller cage, a rate of flow down the vessel may be increased, resulting in a lateral pressure decrease effecting the lymphatic outlet. Because the lymphatic outlet is subject to a pressure decrease, fluids in the lymphatic system drain to the outlet and into the circulatory system.

12 Claims, 44 Drawing Sheets

Related U.S. Application Data

(60) Provisional application No. 62/810,653, filed on Feb. 26, 2019.

(52) U.S. Cl.
CPC .............. *A61M 2025/1022* (2013.01); *A61M 2205/3334* (2013.01); *A61M 2205/3341* (2013.01); *A61M 2210/125* (2013.01)

(58) Field of Classification Search
CPC .... A61M 2025/3341; A61M 2210/125; A61M 60/174; A61M 60/221; A61M 60/237; A61M 60/242; A61M 60/833
See application file for complete search history.

(56) References Cited

U.S. PATENT DOCUMENTS

| | | | |
|---|---|---|---|
| 3,926,175 A | 12/1975 | Allen et al. | |
| 4,714,460 A | 12/1987 | Calderon | |
| 4,822,341 A | 4/1989 | Colone | |
| 4,838,864 A | 6/1989 | Peterson | |
| 4,957,484 A | 9/1990 | Murtfeldt | |
| 4,957,504 A | 9/1990 | Chardack | |
| 5,005,564 A | 4/1991 | Grundei et al. | |
| 5,019,040 A | 5/1991 | Itaoka et al. | |
| 5,069,662 A | 12/1991 | Bodden | |
| 5,092,844 A | 3/1992 | Schwartz et al. | |
| 5,097,840 A | 3/1992 | Wallace et al. | |
| 5,108,370 A | 4/1992 | Walinsky | |
| 5,163,910 A | 11/1992 | Schwartz et al. | |
| 5,295,995 A | 3/1994 | Kleiman | |
| 5,366,504 A | 11/1994 | Andersen et al. | |
| 5,391,143 A | 2/1995 | Kensey | |
| 5,397,307 A | 3/1995 | Goodin | |
| 5,484,412 A | 1/1996 | Pierpont | |
| 5,509,897 A | 4/1996 | Twardowski et al. | |
| 5,554,119 A | 9/1996 | Harrison et al. | |
| 5,556,383 A | 9/1996 | Wang et al. | |
| 5,558,642 A | 9/1996 | Schweich, Jr. et al. | |
| 5,702,364 A | 12/1997 | Euteneuer | |
| 5,716,340 A | 2/1998 | Schweich, Jr. et al. | |
| 5,792,300 A | 8/1998 | Inderbitzen et al. | |
| 5,817,046 A | 10/1998 | Glickman | |
| 5,836,912 A | 11/1998 | Kusleika | |
| 5,893,841 A | 4/1999 | Glickman | |
| 5,897,533 A | 4/1999 | Glickman | |
| 5,908,407 A | 6/1999 | Frazee et al. | |
| 5,911,685 A * | 6/1999 | Siess ................... | F04D 29/047 |
| | | | 600/16 |
| 5,919,163 A | 7/1999 | Glickman | |
| 5,921,913 A | 7/1999 | Siess | |
| 5,954,714 A | 9/1999 | Saadat et al. | |
| 5,964,694 A | 10/1999 | Siess et al. | |
| 6,042,569 A | 3/2000 | Finch, Jr. et al. | |
| 6,139,517 A | 10/2000 | Macoviak et al. | |
| 6,152,945 A | 11/2000 | Bachinski et al. | |
| 6,158,984 A | 12/2000 | Cao et al. | |
| 6,165,196 A | 12/2000 | Stack et al. | |
| 6,179,796 B1 | 1/2001 | Waldridge | |
| 6,183,492 B1 | 2/2001 | Hart et al. | |
| 6,245,007 B1 * | 6/2001 | Bedingham ......... | A61M 60/812 |
| | | | 600/16 |
| 6,248,091 B1 | 6/2001 | Voelker | |
| 6,254,563 B1 | 7/2001 | Macoviak et al. | |
| 6,290,639 B1 | 9/2001 | Mussivand et al. | |
| 6,443,884 B1 | 9/2002 | Miyawaki | |
| 6,503,224 B1 | 1/2003 | Forman et al. | |
| 6,508,787 B2 | 1/2003 | Erbel et al. | |
| 6,524,323 B1 | 2/2003 | Nash et al. | |
| 6,555,057 B1 | 4/2003 | Bendera | |
| 6,616,623 B1 | 9/2003 | Kutushov | |
| 6,635,068 B1 | 10/2003 | Dubrul et al. | |
| 6,699,231 B1 | 3/2004 | Sterman et al. | |
| 6,840,949 B2 | 1/2005 | Barbut | |
| 6,878,140 B2 | 4/2005 | Barbut | |
| 6,936,057 B1 | 8/2005 | Nobles | |
| 7,022,097 B2 | 4/2006 | Glickman | |
| 7,195,608 B2 | 3/2007 | Burnett | |
| 7,645,259 B2 | 1/2010 | Goldman | |
| 7,766,892 B2 | 8/2010 | Keren et al. | |
| 7,766,961 B2 | 8/2010 | Patel et al. | |
| 7,780,628 B1 | 8/2010 | Keren et al. | |
| 8,109,880 B1 | 2/2012 | Pranevicius et al. | |
| 8,126,538 B2 | 2/2012 | Shuros et al. | |
| 8,216,122 B2 | 7/2012 | Kung | |
| 8,480,555 B2 | 7/2013 | Kung | |
| 8,679,057 B2 | 3/2014 | Fulton, III et al. | |
| 8,894,387 B2 | 11/2014 | White | |
| 9,179,921 B1 | 11/2015 | Morris | |
| 9,358,329 B2 | 6/2016 | Fitzgerald et al. | |
| 9,405,942 B2 | 8/2016 | Liao et al. | |
| 9,421,316 B2 | 8/2016 | Leeflang et al. | |
| 9,433,713 B2 | 9/2016 | Corbett et al. | |
| 9,486,566 B2 | 11/2016 | Siess | |
| 9,533,054 B2 | 1/2017 | Yan et al. | |
| 9,533,084 B2 | 1/2017 | Siess et al. | |
| 9,642,991 B2 | 5/2017 | Eversull et al. | |
| 9,669,142 B2 | 6/2017 | Spanier et al. | |
| 9,669,144 B2 | 6/2017 | Spanier et al. | |
| 9,675,739 B2 | 6/2017 | Tanner et al. | |
| 9,682,223 B2 | 6/2017 | Callaghan et al. | |
| 9,750,861 B2 | 9/2017 | Hastie et al. | |
| 9,770,543 B2 | 9/2017 | Tanner et al. | |
| 9,878,080 B2 | 1/2018 | Kaiser et al. | |
| 9,901,722 B2 | 2/2018 | Nitzan et al. | |
| 9,962,170 B2 | 5/2018 | Jansen et al. | |
| 10,149,684 B2 | 12/2018 | Nitzan et al. | |
| 10,154,846 B2 | 12/2018 | Nitzan et al. | |
| 10,195,405 B2 | 2/2019 | Nitzan et al. | |
| 10,207,086 B2 | 2/2019 | Nitzan et al. | |
| 10,226,604 B2 | 3/2019 | Nitzan et al. | |
| 10,226,605 B2 | 3/2019 | Nitzan et al. | |
| 10,245,363 B1 | 4/2019 | Rowe | |
| 10,285,708 B2 | 5/2019 | Nitzan et al. | |
| 10,300,254 B2 | 5/2019 | Nitzan et al. | |
| 10,514,044 B2 | 12/2019 | Schibli et al. | |
| 10,561,496 B2 | 2/2020 | Zhu et al. | |
| 10,639,460 B2 | 5/2020 | Nitzan et al. | |
| 10,653,824 B2 | 5/2020 | Bedworth et al. | |
| 10,653,871 B2 | 5/2020 | Nitzan et al. | |
| 10,709,878 B2 | 7/2020 | Nitzan et al. | |
| 10,912,873 B2 | 2/2021 | Nitzan et al. | |
| 10,926,069 B2 | 2/2021 | Nitzan et al. | |
| 10,960,189 B2 | 3/2021 | Nitzan et al. | |
| 11,007,353 B2 | 5/2021 | Gerrans et al. | |
| 11,166,730 B2 | 11/2021 | Nitzan et al. | |
| 11,179,550 B2 | 11/2021 | Nitzan et al. | |
| 11,179,551 B2 | 11/2021 | Nitzan et al. | |
| 11,179,552 B2 | 11/2021 | Nitzan et al. | |
| 11,357,959 B2 | 6/2022 | Nitzan et al. | |
| 11,406,393 B2 | 8/2022 | Nitzan | |
| 11,904,080 B2 | 2/2024 | Nitzan et al. | |
| 12,115,296 B2 | 10/2024 | Nitzan et al. | |
| 12,179,010 B2 | 12/2024 | Nitzan et al. | |
| 2001/0044598 A1 | 11/2001 | Parodi | |
| 2002/0010418 A1 | 1/2002 | Lary et al. | |
| 2003/0039544 A1 | 2/2003 | Yamazaki | |
| 2003/0040736 A1 | 2/2003 | Stevens et al. | |
| 2003/0093109 A1 | 5/2003 | Mauch | |
| 2003/0134416 A1 | 7/2003 | Yamanishi et al. | |
| 2003/0208097 A1 | 11/2003 | Aboul-Hosn et al. | |
| 2004/0006306 A1 | 1/2004 | Evans et al. | |
| 2004/0039438 A1 | 2/2004 | Alt | |
| 2004/0064091 A1 | 4/2004 | Keren et al. | |
| 2004/0147871 A1 | 7/2004 | Burnett | |
| 2004/0210296 A1 | 10/2004 | Schmitt et al. | |
| 2004/0230181 A1 | 11/2004 | Cawood | |
| 2005/0085772 A1 | 4/2005 | Zafirelis et al. | |
| 2005/0228474 A1 | 10/2005 | Laguna | |
| 2005/0251180 A1 | 11/2005 | Burton et al. | |
| 2006/0030814 A1 | 2/2006 | Valencia et al. | |
| 2006/0064059 A1 | 3/2006 | Gelfand et al. | |
| 2006/0100658 A1 | 5/2006 | Obana et al. | |

(56)     References Cited

U.S. PATENT DOCUMENTS

| | | |
|---|---|---|
| 2006/0122456 A1 | 6/2006 | LaRose et al. |
| 2006/0161095 A1 | 7/2006 | Aboul-Hosn et al. |
| 2006/0178604 A1 | 8/2006 | Alderman |
| 2007/0055299 A1 | 3/2007 | Ishimaru et al. |
| 2007/0282303 A1 | 12/2007 | Nash et al. |
| 2007/0282382 A1 | 12/2007 | Shuros et al. |
| 2008/0009719 A1 | 1/2008 | Shuros et al. |
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0103591 A1 | 5/2008 | Siess |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0100057 A1 | 4/2010 | Atanasoska et al. |
| 2010/0168649 A1 | 7/2010 | Schwartz et al. |
| 2010/0179389 A1 | 7/2010 | Moroney, III et al. |
| 2010/0280451 A1 | 11/2010 | Teeslink et al. |
| 2010/0318114 A1 | 12/2010 | Pranevicius et al. |
| 2011/0004046 A1 | 1/2011 | Campbell et al. |
| 2011/0060313 A1 | 3/2011 | Liu et al. |
| 2011/0084019 A1 | 4/2011 | Shiratori et al. |
| 2011/0092955 A1 | 4/2011 | Purdy et al. |
| 2011/0143014 A1 | 6/2011 | Stankus et al. |
| 2011/0257462 A1 | 10/2011 | Rodefeld et al. |
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 | 2/2012 | Callaghan et al. |
| 2012/0071870 A1 | 3/2012 | Salahieh et al. |
| 2012/0157913 A1 | 6/2012 | Aziz et al. |
| 2012/0178986 A1 | 7/2012 | Campbell et al. |
| 2012/0197194 A1 | 8/2012 | Osypka |
| 2012/0215166 A1 | 8/2012 | Barki |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0177432 A1 | 7/2013 | Toellner et al. |
| 2013/0237954 A1 | 9/2013 | Shuros et al. |
| 2013/0245607 A1 | 9/2013 | Eversull et al. |
| 2013/0303969 A1 | 11/2013 | Keenan et al. |
| 2013/0317535 A1 | 11/2013 | Demmy |
| 2013/0331814 A1 | 12/2013 | Fulton, III et al. |
| 2013/0338559 A1 | 12/2013 | Franano et al. |
| 2014/0010686 A1 | 1/2014 | Tanner et al. |
| 2014/0079557 A1 | 3/2014 | LaRose et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0249614 A1 | 9/2014 | Levi et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0258260 A1 | 9/2015 | Tuseth |
| 2015/0283360 A1 | 10/2015 | Kelly |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0082178 A1 | 3/2016 | Agah et al. |
| 2016/0129266 A1 | 5/2016 | Schmidt |
| 2016/0166463 A1 | 6/2016 | Douglas et al. |
| 2016/0169630 A1 | 6/2016 | Augustine et al. |
| 2016/0213826 A1 | 7/2016 | Tanner et al. |
| 2016/0331378 A1* | 11/2016 | Nitzan ............ A61B 17/12136 |
| 2017/0014563 A1 | 1/2017 | Khir |
| 2017/0049944 A1 | 2/2017 | Kinoshita et al. |
| 2017/0095395 A1 | 4/2017 | Wennen et al. |
| 2017/0122373 A1 | 5/2017 | Gebert et al. |
| 2017/0197021 A1 | 7/2017 | Nitzan et al. |
| 2017/0224512 A1 | 8/2017 | Hingston |
| 2017/0319764 A1 | 11/2017 | Tanner et al. |
| 2018/0012630 A1 | 1/2018 | Thomee et al. |
| 2018/0020456 A1 | 1/2018 | Wan et al. |
| 2018/0055979 A1* | 3/2018 | Corbett ................ A61M 60/13 |
| 2018/0117288 A1 | 5/2018 | Lindsay et al. |
| 2018/0125499 A1 | 5/2018 | Nitzan et al. |
| 2018/0126130 A1* | 5/2018 | Nitzan ............... A61M 60/237 |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2018/0303986 A1 | 10/2018 | Meacham |
| 2019/0014991 A1 | 1/2019 | Maki et al. |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0105436 A1 | 4/2019 | Uchida |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0282741 A1 | 9/2019 | Franano et al. |
| 2019/0365973 A1 | 12/2019 | Flores |
| 2019/0366063 A1 | 12/2019 | Nitzan et al. |
| 2020/0016383 A1 | 1/2020 | Nitzan et al. |
| 2020/0030586 A1 | 1/2020 | Nitzan et al. |
| 2020/0030587 A1 | 1/2020 | Nitzan et al. |
| 2020/0046372 A1 | 2/2020 | Nitzan |
| 2020/0100792 A1 | 4/2020 | Levit |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0261706 A1 | 8/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0008263 A1 | 1/2021 | Leonhardt |
| 2021/0015982 A1 | 1/2021 | Kerkhoffs et al. |
| 2021/0121678 A1 | 4/2021 | Nitzan et al. |
| 2021/0170081 A1 | 6/2021 | Kanz |
| 2021/0236797 A1 | 8/2021 | D'Ambrosio et al. |
| 2021/0330958 A1 | 10/2021 | Stotz et al. |
| 2021/0378676 A1 | 12/2021 | Keating et al. |
| 2021/0378677 A1 | 12/2021 | Keating et al. |
| 2021/0378678 A1 | 12/2021 | Keating et al. |
| 2021/0379329 A1 | 12/2021 | Keating et al. |
| 2022/0039803 A1 | 2/2022 | Nitzan et al. |
| 2022/0104827 A1 | 4/2022 | Keating et al. |
| 2022/0104828 A1 | 4/2022 | Keating et al. |
| 2022/0218360 A1 | 7/2022 | Nitzan et al. |
| 2022/0218961 A1 | 7/2022 | Nitzan et al. |
| 2022/0280761 A1 | 9/2022 | Nitzan et al. |
| 2022/0280762 A1 | 9/2022 | Nitzan et al. |
| 2022/0331510 A1 | 10/2022 | Amstutz et al. |
| 2023/0007905 A1 | 1/2023 | Tschopp et al. |

FOREIGN PATENT DOCUMENTS

| | | |
|---|---|---|
| CN | 104771797 A | 7/2015 |
| CN | 107771089 A | 3/2018 |
| EP | 0526102 A1 | 2/1993 |
| EP | 0629412 A2 | 12/1994 |
| EP | 2353501 A1 | 8/2011 |

(56) References Cited

FOREIGN PATENT DOCUMENTS

| | | | |
|---|---|---|---|
| EP | 2353503 | A1 | 8/2011 |
| EP | 2353632 | A1 | 8/2011 |
| EP | 2497524 | A1 | 9/2012 |
| EP | 2637927 | A1 | 9/2013 |
| EP | 2662099 | A1 | 11/2013 |
| JP | 2000-511442 | A | 9/2000 |
| JP | 2001-515375 | A | 9/2001 |
| JP | 2002-536079 | A | 10/2002 |
| WO | 89/04193 | A1 | 5/1989 |
| WO | 2000/024337 | A2 | 5/2000 |
| WO | 01/013983 | A2 | 3/2001 |
| WO | 02085443 | A1 | 10/2002 |
| WO | 2008/106103 | A2 | 9/2008 |
| WO | 2010/078603 | A2 | 7/2010 |
| WO | 2012/036238 | A1 | 3/2012 |
| WO | 2012/135834 | A2 | 10/2012 |
| WO | 2013/025826 | A1 | 2/2013 |
| WO | 2013025821 | A2 | 2/2013 |
| WO | 2013/061281 | A1 | 5/2013 |
| WO | 2014/141284 | A2 | 9/2014 |
| WO | 2014/141287 | A1 | 9/2014 |
| WO | 2015/186003 | A2 | 12/2015 |
| WO | 2015/186005 | A2 | 12/2015 |
| WO | 2016/181217 | A2 | 11/2016 |
| WO | 2017/087556 | A1 | 5/2017 |
| WO | 2017159849 | A1 | 9/2017 |
| WO | 2018/158636 | A1 | 9/2018 |
| WO | 2018172848 | A2 | 9/2018 |
| WO | 2018/202776 | A1 | 11/2018 |
| WO | 2019/027380 | A1 | 2/2019 |
| WO | 2019/113541 | A1 | 6/2019 |
| WO | 2019/180179 | A1 | 9/2019 |
| WO | 2020/174285 | A2 | 9/2020 |
| WO | 2021/115562 | A1 | 6/2021 |

OTHER PUBLICATIONS

European Exam Report issued in European Application No. 20763700.0, date of mailing: May 2, 2024, 7 pages.

Extended European Search Report issued in European Application No. 20184530.2, date of mailing: Apr. 19, 2024, 8 pages.

Extended European Search Report issued in European Application No. 21821380.9, date of mailing: Apr. 19, 2024, 12 pages.

Extended European Search Report issued in European Application No. 24190127.1, date of mailing: Dec. 5, 2024, 13 pages.

"Can Stainless steel corrode?" Apr. 17, 2019, Thyssenkrupp Materials Hungary (Year:2019).

Children's Hospital of Philadelphia, Guidelines for Choosing Catheter Sizes in the Emergency Department, 2023.

Hong, 2005, Material-specific thrombin generation following contact between metal surfaces and whole bloood, Elsevier, Biomaterials 26, 1397-1403.

Surface Solutions Group, LLC, 2024, Hydrophilic Coatings in the Medical Field, retrieved from the internet on Feb. 6, 2024, URL: https://surfacesolutionsgroup.com/hydrophilic-coatings-in-the-medical-field/, 3 pages.

UnifiedAlloys, 2024, Stainless Steel 101, retrieved from the internet on Feb. 6, 2024, URL: <https://www.unifiedalloys.com/blog/what-is-stainelss-steel,> 11 pages.

Bannon, 2011, Anatomic considerations for central venous cannulation, Risk Manag Healthc Policy 4:27-39.

Biran, 2017, Heparin coatings for improving blood compatibility of medical devices, Adv Drug Delivery Rev, 112:12-23.

Blitz, 2014, Pump thrombosis—a riddle wrapped in a mystery inside an enigma, Ann Cardiothorac Surg, 3(5):450-471.

Chikly, 2005, Manual techniques addressing the lymphatic system: origins and development, JAOA 105(10):457-464.

Moscucci, 2014, Section III Hemodynamic principles 10 Pressure measurement, 223-244 in Grossman & Baim's Cardiac Catheterization, Angiography, and Intervention 8 Ed, 26 pages.

Ratnayake, 2018, The Anatomy and physiology of the terminal thoracic duct and ostial valve in health and disease: potential implications for intervention, J Anat 233:1-14.

Shimizu, 2014, Embolization of a fractured central venous catheter placed using the internal jugular apporach, int J Surg Case Rep 5:219-221.

Stone, 2010, The effect of rigid cervical collars on internal jugular vein dimensions, Acad Emerg Med 17(1):100-102.

Swan, 1970, Catheterization of the Heart in Man with Use of a Flow-directed Balloon-tipped Catheter, NEJM 283 (9):447-451.

Tchantchaleishvili, 2014, Evaluation and treatment of pump thrombosis and hemolysis, Ann Cardiothorac Surg, 3 (5):490-495.

Webb, 2012, Roughness parameters for standard description of surface nanoarchitecture, Scanning 34:257-263.

Yancy, 2013, 2013 ACCF/AHA Guideline for the Management of Heart Failure, Circulation 128(16):e240-e327.

* cited by examiner

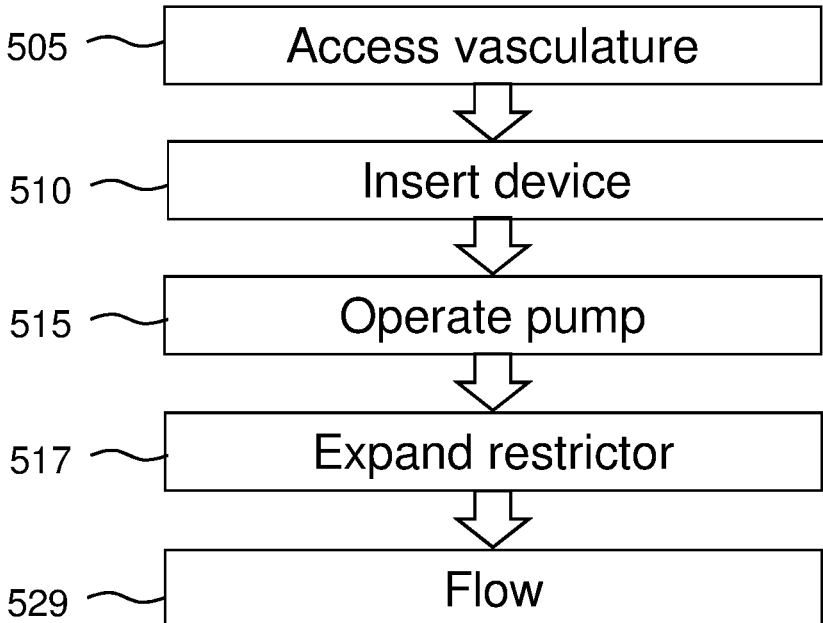
505 — Access vasculature
510 — Insert device
515 — Operate pump
517 — Expand restrictor
529 — Flow
FIG. 5

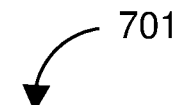
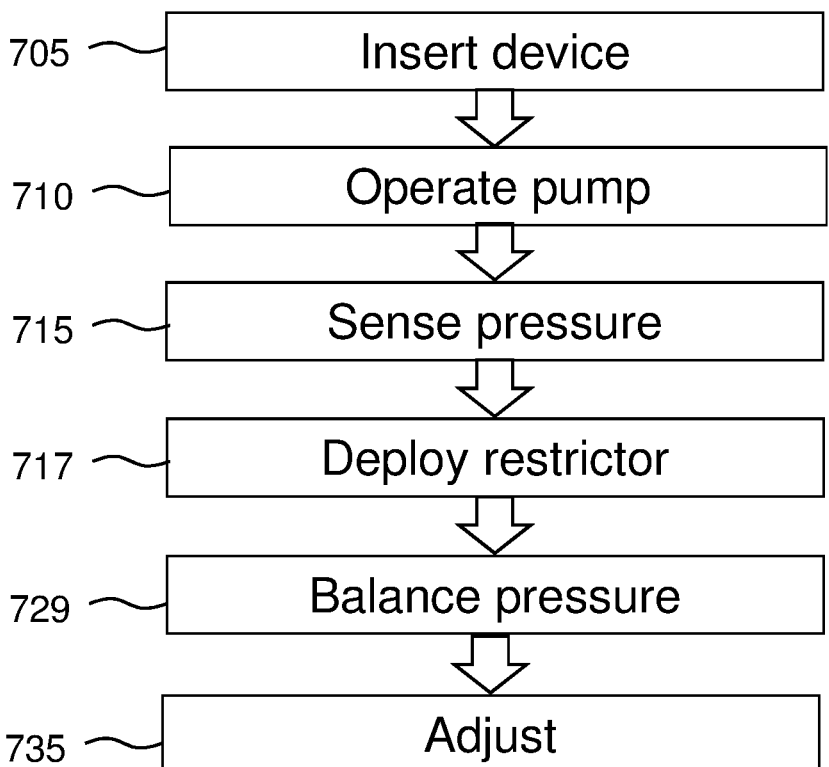
FIG. 7

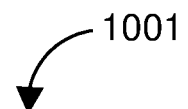
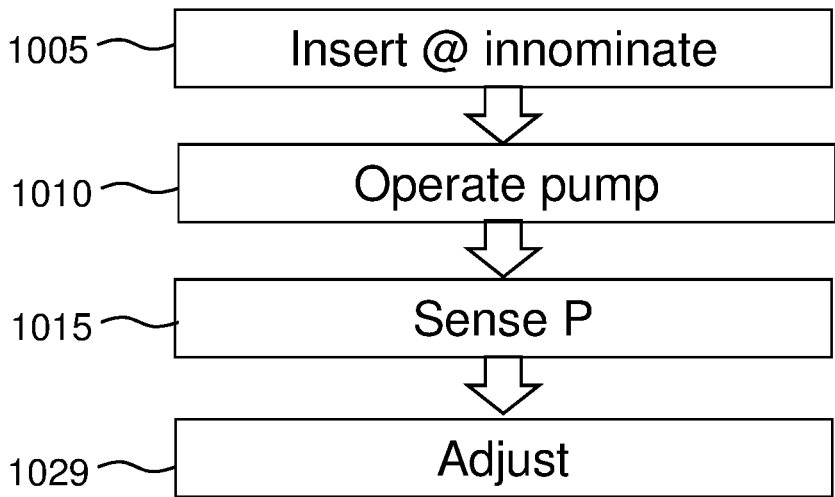
1005 —— Insert @ innominate
1010 —— Operate pump
1015 —— Sense P
1029 —— Adjust
FIG. 10

Cage

1201

1205 — Insert

1210 — Drive

1215 — Exclude

1217 — Decrease P

1229 — Inflate

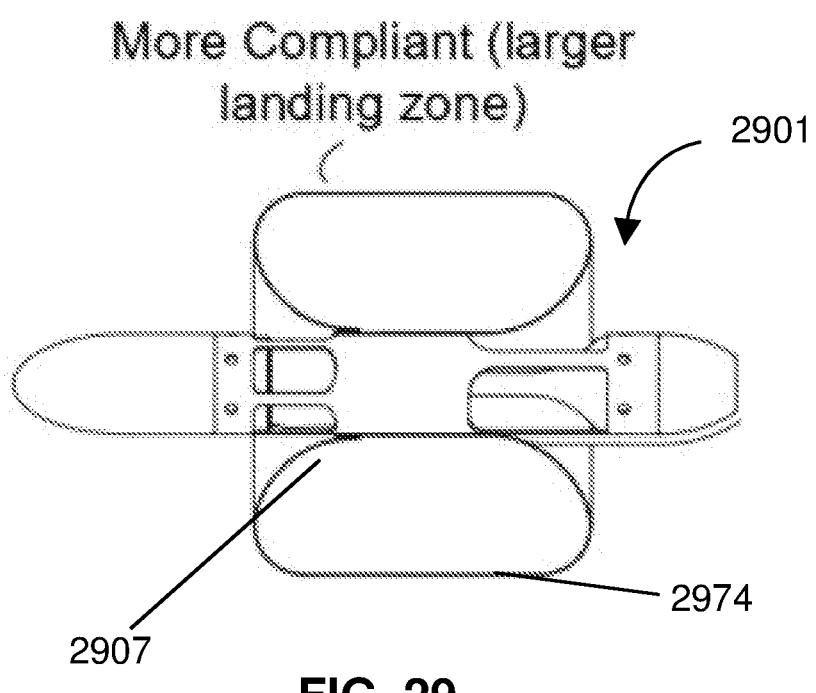
More Compliant (larger landing zone)
2901
2974
2907
FIG. 29
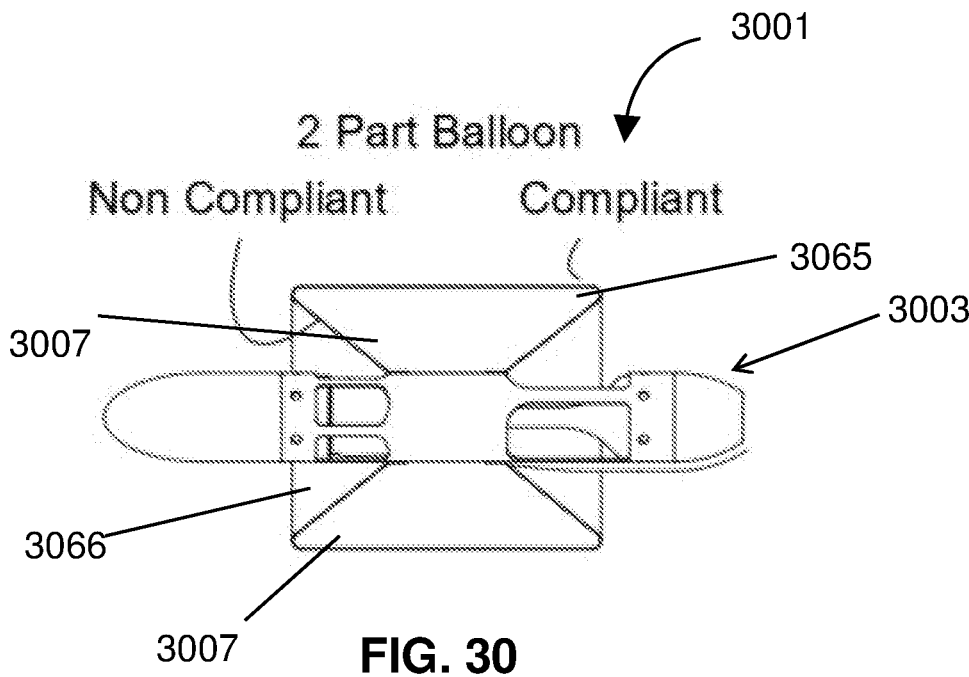
3001
2 Part Balloon
Non Compliant          Compliant
3065
3003
3007
3066
3007          FIG. 30

3101

Flexible Inflation Lumen

Flexible Shaft (Containing Drive Shaft)

3107

3103    3133    3139

3201

3207          Flexible Membrane          3255          3279

Coated NiTi          Pull Wire 3258    3203          3200

3500

3585

3581

3583

3501

3556

3508

3585

3507

3503

4392

4300

4500

Section A-A

5005

5029

5023

5101

5005

5201

5023

DEVICES AND METHODS FOR TREATING EDEMA

This application is a continuation of U.S. nonprovisional application Ser. No. 16/801,994, filed Feb. 26, 2020 (now issued as U.S. Pat. No. 11,660,426), which claims benefit of U.S. Provisional Application No. 62/810,653, filed Feb. 26, 2019, both of which are incorporated herein by reference.

TECHNICAL FIELD

The disclosure relates to devices and methods for the treatment of edema.

BACKGROUND

Congestive heart failure occurs when the heart is unable to pump sufficiently to maintain blood flow to meet the body's needs. A person suffering heart failure may experience shortness of breath, exhaustion, and swollen limbs. Heart failure is a common and potentially fatal condition. In 2015 it affected about 40 million people globally and around 2% of adults overall. As many as 10% of people over the age of 65 are susceptible to heart failure.

In heart failure, the pressures in the heart ventricles and atria are excessively elevated. As a result, the heart works harder to eject blood, leading to a buildup of blood pressure, which may result in edema forming within interstitial compartments of the body. Edema refers to the abnormal accumulation of fluid in tissues of the body and results when elevated blood pressure prevents lymphatic fluid from draining from the interstitium. The additional work of the heart, with time, weakens and remodels the heart thus further reducing the ability of the heart to function properly. The fluid accumulation leads to dyspnea and acute decompensated heart failure (ADHF) hospitalization. Those conditions may result in severe health consequences including death.

SUMMARY

The invention provides devices and methods for treatment of edema that use an indwelling catheter with an impeller to lower pressure at an outlet of a lymphatic duct and a balloon on the impeller to guide and to restrict blood flow. The balloon restricts return flow from the jugular and guides that flow into the impeller cage. By funneling the flow into the impeller cage, a rate of flow down the vessel may be increased, resulting in a lateral pressure decrease effecting the lymphatic outlet. Because the lymphatic outlet is subject to a pressure decrease, fluids in the lymphatic system drain to the outlet and into the circulatory system. These effects can be optimized by having the balloon disposed on or around the impeller cage and, in some embodiments, the balloon may be connected directly the impeller cage, surrounding the cage, and forming a torus that funnels fluid flow into the impeller cage. A shape of a balloon in a deployed state directs and facilitates blood flow into an inlet of an impeller. By using the impeller in conjunction with the balloon on the catheter, the ability of the device to lower pressure at the lymphatic outlet is optimized.

The geometry of the combined impeller cage and toroidal balloon employ flow dynamics to drain the lymphatic system. The impeller cage in combination with the balloon creates a local constriction (or choke) in the cross-sectional area of flow through the vessel (e.g., the innominate vein). This flow constriction results in a Venturi effect, in which fluid pressure is reduced as applicable to the outlet of the lymphatic duct. Due to the pressure decrease experienced by the lymphatic outlet, lymph drains from the lymphatic system to the circulatory system. Thus devices and methods of the disclosure use a balloon mounted to an impeller to exploit the laws of fluid mechanics to drain lymph. Since operating an impeller in an innominate vein near a lymphatic outlet with a balloon connected to the impeller cage is effective to reduce pressure at the lymphatic outlet and drain lymph, devices and methods of the invention are useful to relieve the symptoms of edema. Accordingly, the invention provides methods and devices that use a balloon mounted to an impeller cage to treat edema and congestive heart failure.

In certain aspects, the disclosure provides a device for treating edema. The device includes a catheter having a proximal portion and a distal portion, an impeller housing attached to the distal portion of the catheter with an impeller disposed therein, and an expandable member (e.g., a balloon) aligned over an outside of the impeller housing. An exterior surface of the expandable member may be physically coupled to an exterior surface of the impeller housing. Preferably, the exterior surface of the expandable member is physically coupled directly to the exterior surface of the impeller housing, i.e., without any membrane, sheath, or device between the exterior surface of the expandable member and the exterior surface of the impeller housing. The expandable member may surround the impeller housing.

Where the expandable member is a balloon, the balloon may inflatable and may surround the impeller housing. In some embodiments, the impeller housing comprises a metal and a portion of the expandable member is fixed to a surface of the metal by an adhesive. At least a portion of the surface of the metal may be impregnated with a polymer to promote bonding to the adhesive. Embodiments of the device may include a motor housing connected to the proximal portion of the catheter with a motor disposed within the motor housing. A drive cable may extend through the catheter from the motor to the impeller with an inflation lumen extending along the catheter to the expandable member. Related embodiments provide a method of using the device for treating edema. The method includes inserting the distal portion of the catheter into an innominate vein of a patient, operating the impeller, and expanding the expandable member to thereby decrease pressure at a lymphatic duct.

Aspects of the invention provide an edema treatment device that includes a catheter with a proximal portion and a distal portion, the distal portion dimensioned for insertion into a lumen of a patient and comprising a pump, and an expandable member connected to the pump. When expanded, the expandable member comprises a toroidal shape, in which a proximal surface of the toroidal shape directs fluid into the pump. Preferably an inner radius of the toroidal shape is substantially the same as a radius of the proximal end of the pump. The expandable member may include an inflatable balloon mounted on the pump. In some embodiments, the pump comprises an impeller housing with an impeller therein, with the balloon mounted around at least a portion of a proximal end of the impeller housing. In certain embodiments, the impeller housing has a distal portion and a proximal portion, in which an external diameter of the proximal portion is smaller than an external diameter of the distal portion, such that the expandable member, when not expanded, is disposed around the proximal portion of the impeller housing. The impeller may have one or more blades on a shaft, with a radius measured from an axis of the impeller to an outer edge of the blades decreasing from a distal to a proximal portion of the impeller. The outer edge of each blade may include a dogleg defining a step-down in radius located adjacent a transition between the distal portion and the proximal portion of the impeller housing. In preferred embodiments, the distal portion of the impeller housing has outlets and the impeller shaft flares outwards near a distal end of the impeller such that when the impeller is rotated, the impeller pumps blood through the impeller housing and out of the one or more outlets.

The pump may include an impeller disposed within an impeller housing and the expandable member may include an inflatable balloon connected to an exterior surface of the impeller housing. In certain embodiments, when the balloon is inflated, it defines a torus. When the balloon is inflated, a surface of the torus may be attached to a surface of the impeller housing. Preferably, when the expandable member is not expanded, the distal portion of the catheter may be passed through a 12 Fr introducer sheath.

Aspects of the disclosure provide a device and associated method that use a restrictor for compensation to pressure changes resulting from flow induced by a pump. In the restrictor for flow compensation aspects, the invention provides a method for treating edema. The method includes operating a pump to increase flow through an innominate vein of a patient and—subsequent to the operating step—deploying a restrictor upstream of the pump to thereby restrict flow from a jugular vein to the innominate vein in order to balance pressure downstream of the pump. The method may include operating the pump and then restricting the flow once the increased flow through the innominate vein affects pressure in the jugular vein. The method may further include sensing, with a pressure sensor, an increase in pressure in the jugular vein that results from the increased flow and restricting the flow in response to sensing the increased pressure in the jugular vein. Restriction of the flow may be adjusted according to the sensed pressure. Preferably, the method includes placing a device comprising the pump within vasculature of a patient prior to the operating step. The device comprises a catheter dimensioned to be at least partially implanted within the vasculature and the pump comprises an impeller assembly disposed at a distal portion of the catheter. In some embodiments, a proximal portion of the catheter is connected to a motor housing and the device includes a pressure sensor and a deployable restrictor attached to the catheter proximal to the pump. Preferably, the restrictor includes an inflatable balloon and restricting the flow includes inflating the restrictor. The sensing may be performed using a computer system communicatively connected to the pressure sensor. The inflation of the restrictor may be periodically or continually adjusted according to the sensed pressure.

Other aspects of the invention provide a method for treating edema. The method includes operating a pump to increase flow through an innominate vein of a patient, sensing a pressure change in a jugular vein of the patient that results from the increased flow, and adjusting a restrictor to restrict flow from the jugular vein to the innominate vein based on the sensed pressure. The method may further include inserting a catheter into the innominate vein, wherein the catheter comprises the pump, a pressure sensor, and the restrictor. Preferably, the restrictor includes an inflatable balloon and adjusting the restrictor includes at least partially inflating the balloon. The sensing may be performed using a pressure sensor. The method may include periodically or continually adjusting inflation of the restrictor according to the sensed pressure. Preferably, the method includes adjusting the inflation in order to balance pressure downstream of the pump. Optionally the pump comprises an impeller assembly disposed at a distal portion of the catheter. A proximal portion of the catheter may be connected to a motor housing having a motor therein operably coupled to the impeller assembly. In some embodiments, the catheter is coupled to a computer system operable to read the pressure or control the inflation.

Aspects of the invention provide a purge-free system, device, and method for treatment of edema. For example, aspects provide a purge-free device that includes a catheter with a proximal portion and a distal portion, an impeller connected to the distal portion of the catheter, a motor connected to the proximal portion of the catheter, a drive cable extending through the catheter from the motor to the impeller, and an impermeable sleeve extending through the catheter over the drive cable. The sleeve features a distal seal at the impeller and a proximal seal at the motor such that fluid external to the sleeve is prevented from entering the sleeve and contacting the drive cable. The sleeve and at least the distal seal exclude fluid from the drive cable. Either seal (or both) may include one or more O-rings. The device may include a first lumen and a second lumen, both extending through the catheter, in which the first and second lumen have respective first and second proximal ends accessible outside of the motor housing. Preferably the first lumen and the second lumen are symmetrically disposed about the drive cable to impart balance to the device. The catheter preferably does not include a purge system or a purge fluid. In some embodiments, the impeller sits in an impeller housing and the device also has at least one expandable member connected to the distal portion of the catheter. The expandable member may be connected to the impeller housing, and the device may also include a second expandable member disposed along the catheter. Preferably, the first expandable member comprises a toroidal balloon connected directly to a surface of the impeller housing. The device may also include at least one pressure sensor disposed along the catheter proximal to the impeller.

In some embodiments, the proximal seal comprises a fitting between the impermeable sleeve and a portion of the impeller, such that the fitting excludes fluids and allows the impeller and drive cable to rotate within the device.

A related aspect provides a method using the purge-free device. The purge-free device may be used in a method of treating edema. The method includes inserting into an innominate vein of a patient a distal portion of a catheter and driving an impeller connected to the distal portion of the catheter by means of motor at a proximal portion of the catheter. The motor is connected to the impeller by a drive cable extending through the catheter. Driving the impeller decreases pressure at a lymphatic duct. An impermeable sleeve extends through the catheter over the drive cable such that body fluid external to the impermeable sleeve is prevented from entering the impermeable sleeve and contacting the drive cable. The method may further comprise inflating a restrictor disposed along the distal portion of the catheter to restrict flow from a jugular vein into the innominate vein, wherein the inflating uses an inflation lumen extending through the catheter outside of the impermeable sleeve. The decreased pressure at a lymphatic duct promotes drainage from a lymphatic system into a circulatory system.

Preferably, the impermeable sleeve has a proximal seal at a housing of the motor and a distal seal at the impeller. The proximal seal prevents the blood and bodily fluid from escaping the patient through the motor housing or the proximal portion of the catheter. The distal seal may include a fitting between the impermeable sleeve and a portion of the impeller, in which the fitting excludes fluids and allows the impeller and drive cable to rotate within the device. The impermeable sleeve may be made of a polymer such as Teflon.

The method may include inflating at least one balloon disposed along the catheter by means of an inflation lumen having a proximal end accessible outside of the motor housing while the distal portion of the catheter is inserted into the innominate vein. Blood and bodily fluid is preferably excluded from the drive cable without the use of a purge fluid or purge system.

Other aspects of the disclosure related to methods and devices that use and deliver an anticoagulant to promote effective operation of a device of treatment of edema. For example, aspects of the disclosure provide a device that includes an intravascular pump with built-in delivery mechanism for an anticoagulant (i.e., to deliver the anticoagulant to moving parts of the pump). Thus the invention provides an edema treatment device that includes a catheter, an impeller assembly mounted at a distal portion of the catheter, and a medicament lumen extending through the catheter and terminating substantially at an inlet of the impeller assembly such that a medicament released from the medicament lumen flows through the inlet and impeller assembly. Preferably, the catheter and impeller assembly are dimensioned for insertion through a jugular vein of a patient. The device may further include a reservoir in fluid communication with the medicament lumen. The impeller assembly may comprise an impeller housing with an impeller rotatably disposed therein. The device may include a motor connected to a proximal end of the catheter and operably connected to the impeller via a drive cable extending through the catheter. Preferably, the port is located at the impeller housing, proximal to the impeller.

In some embodiments, the catheter comprises a tube with a drive cable extending therethrough, with a cap connected around a terminal portion of the tube. The impeller housing is mounted to the cap by a plurality of struts to define inlets into the impeller housing. The cap seals a terminus of the flexible tube to a shaft of the impeller, and the port may be located in the cap. The impeller housing may have one or more outlets around a distal portion of the impeller, such that operation of the impeller within a blood vessel drives blood into the impeller assembly via the inlets and out of the impeller assembly via the outlets.

The device may include an anticoagulant (e.g., tirofiban, heparin, warfarin, rivaroxaban, dabigatran, apixaban, edoxaban, enoxaparin, or fondaparinux) in the reservoir. When the device is inserted into a blood vessel of a patient and the impeller is operated, the anticoagulant is released from the port in the impeller cage and the released anticoagulant mixes with blood and washes over the rotating impeller.

Related aspects of the invention provide a method for treating edema. The method includes operating a pump to increase flow through an innominate vein of a patient and releasing an anticoagulant at or adjacent an inlet of the pump. The pump may include an impeller in a cage at a distal portion of a catheter and the anticoagulant may be released from a port in or adjacent a proximal portion of the cage. Optionally, a proximal end of the catheter terminates at a housing comprising a motor, with the motor operably coupled to the impeller by a drive cable extending through the catheter. The catheter may include a medicament lumen extending therethrough and terminating at the port. The method may include the steps of providing the anticoagulant in a reservoir in fluid communication with the medicament lumen; inserting the catheter into vasculature of the patient to position the impeller in the innominate vein; operating the motor to drive the impeller; and washing the anticoagulant over the impeller by releasing the anticoagulant from the port. Preferably, operating the pump decreases pressure at a lymphatic duct, thereby draining lymph from a lymphatic system of the patient.

In certain embodiments, the pump includes an impeller on a distal portion of a catheter and the anticoagulant is released from a port at a proximal portion of the impeller.

By the release of the anticoagulant, clotting or thrombosis is prevented from interfering with operation of the impeller. Optionally, the method may include restricting flow from a jugular vein to the innominate vein to thereby promote flow from a subclavian vein to the innominate vein.

BRIEF DESCRIPTION OF THE DRAWINGS

FIG. 5 shows steps of a method of using the device for treating edema.

FIG. 7 diagrams a method for treating edema that uses a restrictor to balance pressure and compensate for downstream flow.

FIG. 10 diagrams a related method for treating edema using a restrictor for balance/compensation.

FIG. 29 shows an impeller assembly with an expandable member having an elongated surface for interfacing with a wall of a blood vessel.

FIG. 30 shows an impeller assembly with a two-part expandable member.

DETAILED DESCRIPTION

The disclosure relates to devices and methods for treating edema or congestive heart failure. Devices of the disclosure include catheters dimensioned for insertion through a jugular vein, in which the catheters use or include various features each alone or in combination as described herein. Embodiments of the devices include treatment devices in which a flow restrictor such as a balloon is mounted to a cage or housing of an intravascular pump or impeller. In some of those embodiments, a shape of a balloon in a deployed state directs and facilitates blood flow into an inlet of an impeller. In certain embodiments, devices of the disclosure include an impeller that has a smaller diameter proximal end as compared to a distal end to compensate in size for positioning of a balloon on an impeller cage. Aspects of the invention relate to a purge-free system, or purge-free intravascular treatment catheters that do not use a purge fluid to protect an impeller from thrombosis or clotting. In certain embodiments, devices and methods of the disclosure use the release of an anticoagulant such as heparin at an inlet of an impeller cage. Other embodiments of the disclosure relate to devices and methods that use a restrictor such as a balloon to balance pressure and to compensate for downstream flow when an impeller is operated to drain a lymphatic duct. Features and embodiments of the disclosure include edema treatment devices that include an arrangement of lumens that is symmetrical about a drive shaft to impart balance to the drive shaft. In some embodiments, those lumens have a proximal terminus outside of a motor housing and extend down to a distal portion of a catheter. Device of the disclosure may include an atraumatic tip with a thread therein to allow for a smooth material transition. Embodiments of the disclosure may include a guidewire running through an impeller cage. Those embodiments are described and shown in greater detail herein and may be present in any suitable combination in a device of the disclosure.

Figure 1:
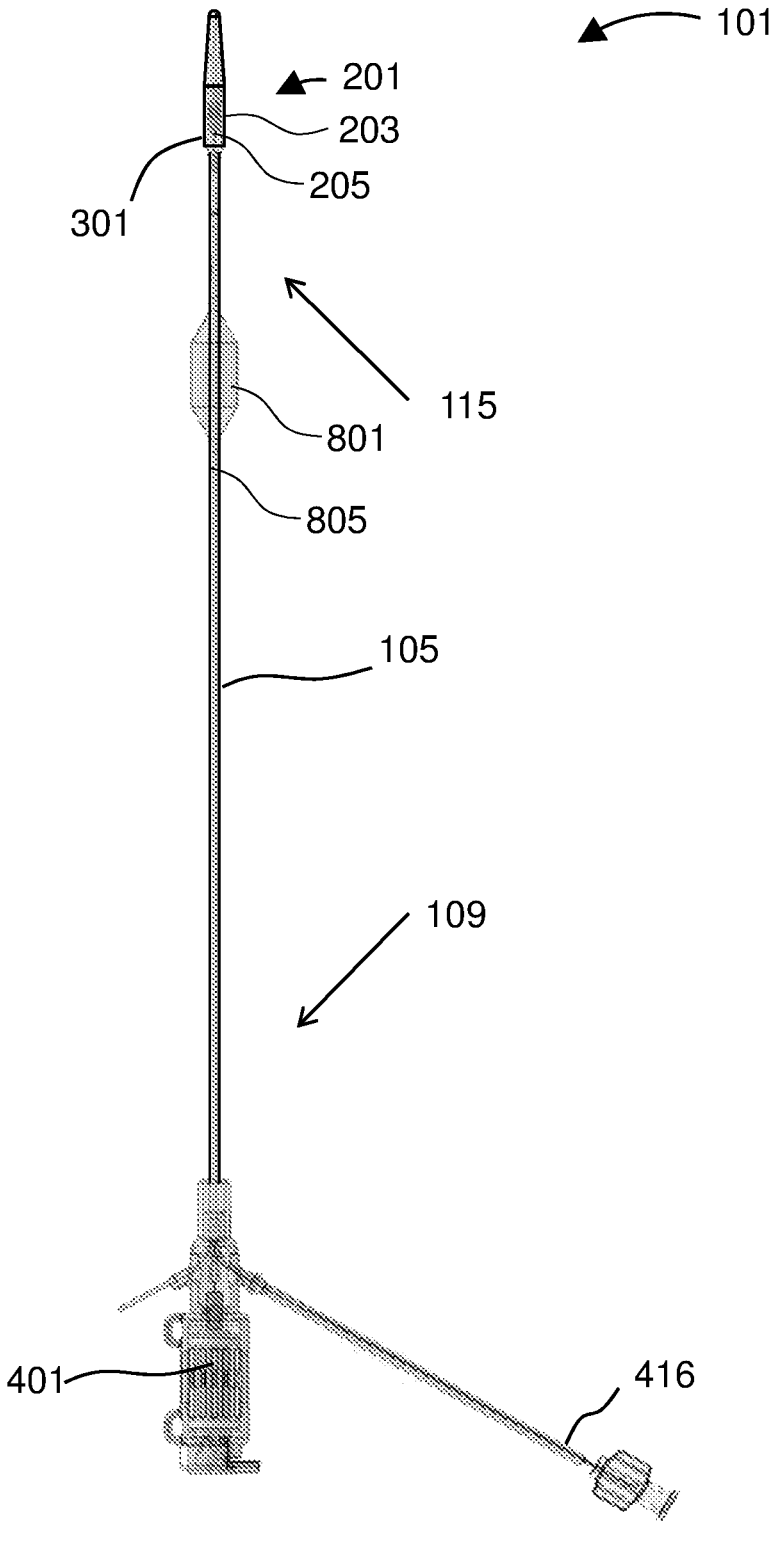
FIG. 1 shows a device for treatment of edema.

FIG. 1 shows a device 101 for treatment of edema. The device 101 includes a catheter 105 comprising a proximal portion 109 and a distal portion 115. An impeller housing 203 is attached to the distal portion 115 of the catheter 105 with an impeller disposed therein. An expandable member 301 may be aligned over an outside of the impeller housing 203. The expandable member 301 is depicted in a collapsed configuration, and thus appears as little more than a smooth continuation of the impeller housing 203.

The device 101 may include a restrictor 801 and at least one pressure sensor 805. In the depicted embodiment, the restrictor 801 is proximal to the expandable member 301. Preferably, each of the restrictor 801 and the expandable member 301 is independently selectively deployable to restrict, impede, guide, or direct fluid flow around the relevant portion of the device 101. In preferred embodiments, each of the restrictor 801 and the expandable member 301 sits in fluid communication with a dedicated inflation lumen that runs along a length of the catheter 105.

One feature of the device 101 is the impeller 205, which is preferably provided within an impeller assembly 201 that provides the impeller housing 203 and other mechanical features such as ports and openings useful to pump blood and fluid within blood vessels of a patient.

Figure 2:
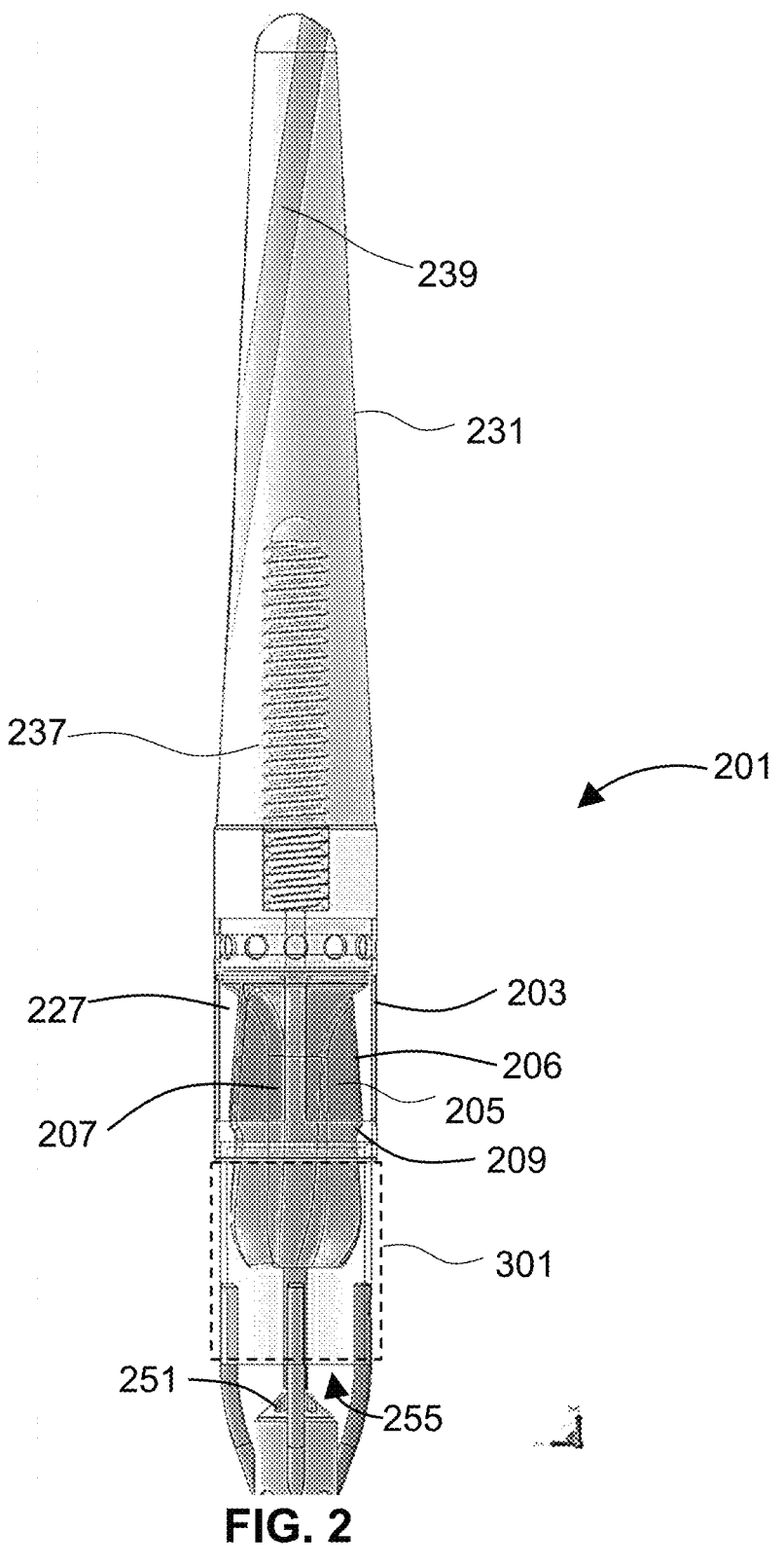
FIG. 2 gives a detail view of the impeller assembly.

FIG. 2 gives a detail view of the impeller assembly 201. The impeller assembly 201 includes an impeller housing 203 with an impeller 205 rotatably disposed therein. An expandable 301 member is aligned over an outside of the impeller housing 203. The expandable member is represented in FIG. 2 using dashed lines (ghosted lines to aid in seeing other features of the device 101). The dashed lines represent the location and disposition of the expandable member 301 in its collapsed or un-deployed state. The impeller housing 203 is attached to the distal portion 115 of the catheter 105 with an impeller disposed therein. An expandable 301 member is aligned over an outside of the impeller housing 203. The expandable member is represented in FIG. 2 using dashed lines (ghosted lines to aid in seeing other features of the device 101). The dashed lines represent the location and disposition of the expandable member 301 in its collapsed or un-deployed state.

As shown, the impeller comprises 205 has blades 206 on a shaft 207. A radius measured from an axis of the impeller 205 to an outer edge of the blades 206 decreases from a distal to a proximal portion of the impeller. This can be seen in that an outer edge of each blade 206 includes a dogleg 209 defining a step-down in radius located adjacent a transition between the distal portion and the proximal portion of the impeller housing 203.

When the distal portion 115 of the device 101 is inserted into vasculature of a patient and a motor in the motor in the motor housing 401 is operated, the impeller 205 rotates and drives fluid (i.e., blood) through the impeller housing 203. To that end, a proximal end of the impeller housing 203 includes one or more inlets 255 and a distal portion of the impeller housing 203 comprises one or more outlets 227. The impeller shaft 207 flares outwards near a distal end of the impeller 205 such that when the impeller 205 is rotated, the impeller pumps blood through the impeller housing 203 and out of the one or more outlets 227.

Figure 14:
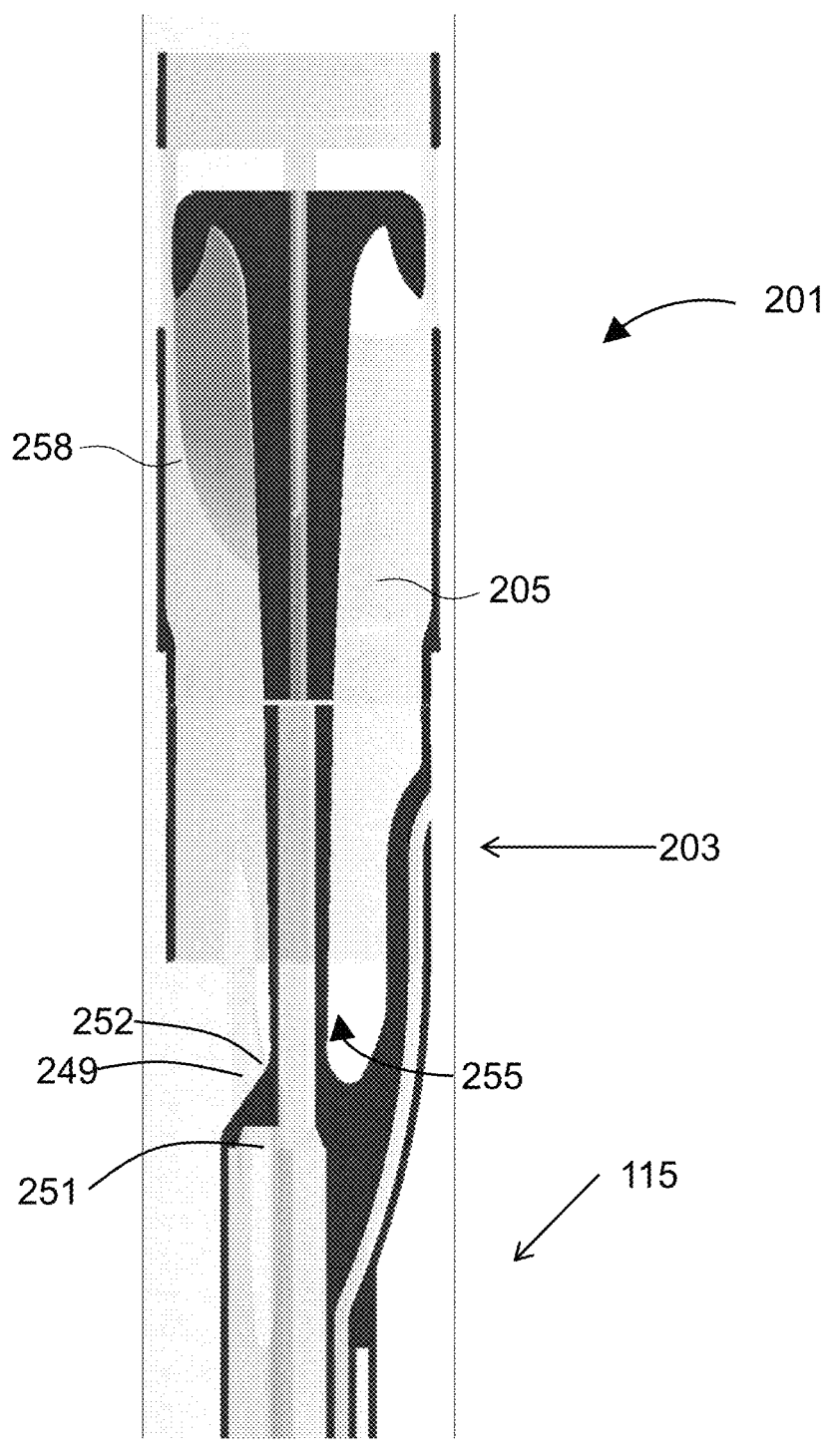
FIG. 14 is a cross-sectional view through an impeller assembly.

FIG. 14 is a cross-sectional view through the impeller assembly 201 on the distal portion 115 of the device 101. The impeller assembly 201 includes an impeller housing 203 with an impeller 205 rotatably disposed therein.

The impeller assembly 201 is connected to the distal portion 115 of the catheter. The impeller assembly has the impeller 205 operably disposed within the assembly. The cutaway view of the impeller assembly 201 shows a proximal portion of the impeller assembly is configured to facilitate flow into an inlet of the impeller assembly without recirculation.

When the impeller 205 operates within a blood vessel, blood flows through a housing 203 of the impeller assembly 201 without recirculation.

As illustrated by the cross-sectional view, in the depicted embodiment, the impeller assembly 201 comprises a cap 249 secured to the distal portion 115 and one or more struts 1405 extending from the cap 249 to the housing 203. Any one or more of the struts 1405 may include a lumen 415. The housing 203 has a diameter greater than a diameter of the cap 249. It can be seen that structurally, a proximal base of the housing 203, the cap 249, and the one or more struts 105 define one or more inlets into the impeller housing 201.

In the depicted embodiment, the strut 1405 has an inflation lumen 415 extending therethrough for inflating a balloon mounted on the impeller assembly. The strut 1405 is substantially parallel to an axis of the impeller 205 and protrudes radially inward from at least a portion of an inner surface of the impeller housing 203. When structured as such, each strut 1405 defines a vane within the impeller assembly 201 that channels fluid flow when the impeller 205 operates to thereby prevent the recirculation or vortices.

As shown, the strut 1405 has a fluidic lumen 415 extending therethrough. The fluidic lumen 415 is non-concentric with at least a portion of the body of the strut 1405 due to material of the strut 1405 forming the vane within the impeller assembly 201. With reference to, e.g., FIG. 3, it can be seen that the device 101 may include a plurality, e.g., at least three, of the struts. Together, the struts define vanes within the impeller assembly that channels fluid flow when the impeller operates to thereby prevent the recirculation or vortices.

The impeller housing 201 includes one or more outlets 258 around a distal portion of the impeller 205. Operation of the impeller 205 within a blood vessel drives blood into the impeller assembly 201 via the inlets 255 and out of the impeller assembly 201 via the outlets 258 such that the blood exhibits smooth laminar flow without the recirculation or vortices.

Figure 15:
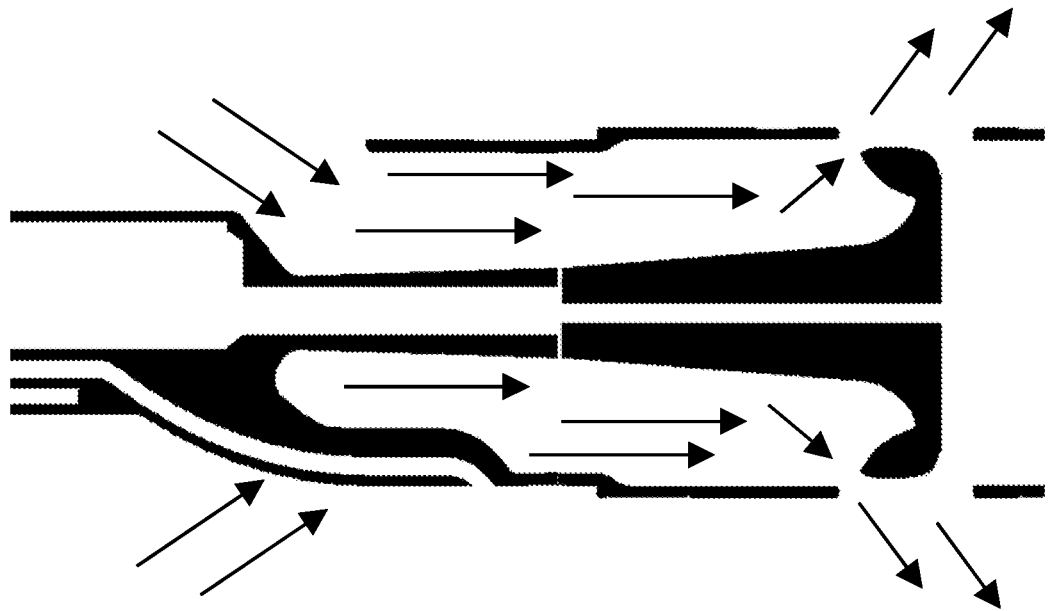
FIG. 15 shows results of a computerized flow model.

FIG. 15 shows how blood flows through the impeller assembly 201 via the inlets 255 and out of the impeller assembly 201 via the outlets 258 such that the blood exhibits smooth laminar flow without the recirculation or vortices. The image depicts results of a computerized flow model. The flow model shows that flow through an impeller assembly with a structure of the invention is smooth and does not exhibit recirculation.

Because the model test results show smooth and efficient flow, a device of the invention pumps blood more efficiently than other devices that lack structures as shown herein.

The computer model test results show that flow is smooth and that there are no vortices or recirculation within the flow.

Because devices of the invention are more efficient than other devices and pump blood without vortices or recirculation, devices of the invention are beneficial for treating patients with edema. Thus, using a device of the disclosure, a clinician may perform a method for treating edema. The method includes inserting into an innominate vein of a patient a distal portion 115 of a catheter. The catheter has an impeller assembly 201 on the distal portion 115. The method includes driving an impeller 205 disposed within the impeller assembly 201 to thereby decrease pressure at a lymphatic duct. A proximal portion of the impeller assembly 201 is configured to facilitate flow into an inlet of the impeller assembly without recirculation as clearly shown in the depicted computer flow model. The catheter may have any of the other features disclosed herein (e.g., a cap secured to the distal portion with one or more struts extending from the cap to support a housing of the impeller assembly in which the housing has a diameter greater than a diameter of the cap, and in which a proximal base of the housing, the cap, and the one or more struts define the inlet).

As shown by the image of results from the computer flow model, the struts define vanes within the impeller assembly that channel fluid flow when the impeller operates to thereby prevent the recirculation or vortices. The flow lines appearing in the computer flow model clear avoid any loops that would appear if the flow had recirculation or vortices. Because flow through the impeller assembly 201 has no recirculation or vortices, the image from the computer flow model shows only flow lines that do not have loops, circles, spirals, etc.

The impeller housing includes one or more outlets around a distal portion of the impeller. When the impeller is operated within a blood vessel, the impeller drives blood into the impeller assembly via the inlets and out of the impeller assembly via the outlets such that the blood exhibits smooth laminar flow without the recirculation or vortices.

Devices and methods of the disclosure may include other features.

A device 101 of the disclosure may further include a medicament lumen 251 extending through the catheter 105 and terminating substantially at an inlet 255 of the impeller assembly 201. In some embodiments, the impeller assembly 201 also includes an atraumatic tip 231 with a threaded fitment 237 therein to allow for a smooth transition of material properties between the rigid impeller cage 203 (e.g., a metal) and the softer material of the atraumatic tip 239. The tip 239 preferably includes a suitable soft material such as a polymer. The material may include, for example, polyether block amides such as those sold under the trademark PEBAX by Arkema Inc. (King of Prussia, PA).

Although polyether block amides are mentioned in detail, the polymer can comprise any number of other polymers such as polytetrafluoroethylene (PTFE), fluorinated ethylene propylene (FEP), polyurethane, polypropylene (PP), polyvinylchloride (PVC), polyether-ester, polyester, polyamide, elastomeric polyamides, block polyamide/ethers, silicones, polyethylene, Marlex high-density polyethylene, linear low density polyethylene, polyetheretherketone (PEEK), polyimide (PI), or polyetherimide (PEI). The threaded fitment 237 may include a threaded post (e.g., of metal or a plastic such as a polycarbonate) threadingly fitted to both the impeller housing 203 and the atraumatic tip 231. By including a long post for the fitment 237 (e.g., longer than its own maximal diameter, preferably at least about 2 or 3× longer), the tip 231 can deform but is prevented from assuming or exhibiting any kinks or discontinuities. Further, as shown, the tip 231 may include a guidewire lumen 239.

The expandable member 301 on the impeller assembly 201 is depicted in the collapsed configuration with dashed lines. The impeller assembly 201 operates as a pump and includes the impeller 205 disposed within the impeller housing 203. In preferred embodiments, the expandable member 301 comprises an inflatable balloon connected to an exterior surface of the impeller housing 203.

Figure 3:
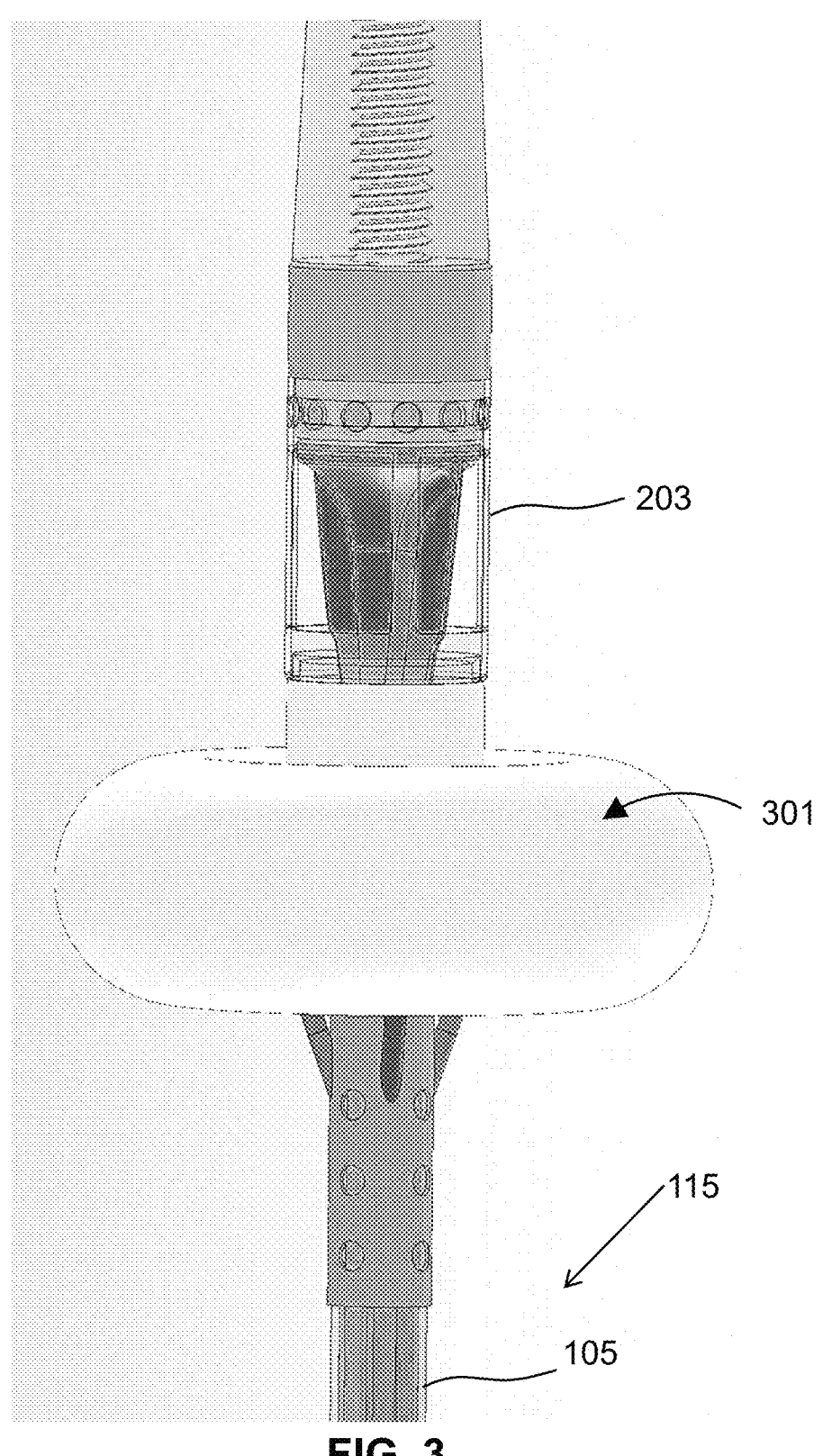
FIG. 3 shows the expandable member in a deployed state.

FIG. 3 shows the expandable member 301 in a deployed state. In the depicted embodiment, the expandable member 301 is provided as a balloon. As shown, when the balloon is inflated, it defines a torus. An exterior surface of the expandable member 301 is physically coupled to an exterior surface of the impeller housing 203 (e.g., the balloon may be cemented to the housing 203 with an adhesive).

Preferably, the exterior surface of the expandable member 301 is physically coupled directly to the exterior surface of the impeller housing 203 without any membrane, sheath, or device 101 between the exterior surface of the expandable member 301 and the exterior surface of the impeller housing 203. The expandable member 301 may partially or fully surround the impeller housing 203. The expandable member 301 may be provided as an inflatable balloon that surrounds the impeller housing 203.

Devices of the disclosure may include feature to facilitate bonding of the balloon to the impeller housing 203. For example, the impeller housing may include metal (e.g., stainless steel, steel, aluminum, titanium, a nickel-titanium alloy, etc.) and a portion of the expandable member 301 may be fixed to a surface of the metal by an adhesive. To facilitate bonding, at least a portion of the surface of the metal may be impregnated with a polymer. In some embodiments, the metal surface at least at the exterior, proximal portion of the impeller cage 203 is impregnated with polyurethane to a depth of at least 3 μm.

Using the expandable member 301 mounted to the impeller cage 203, the device 101 is configured for placement in a body vessel. The impeller housing comprises an axis that may be placed substantially parallel to an axis of the vessel. Preferably, the expandable member 301 is impervious to flow across the expandable member. The expandable member 301 is configured in use to appose the wall of a blood vessel and in so doing direct fluid flow to an inlet of the impeller housing 203.

In use, the expandable member 301 anchors or holds the impeller assembly 201 in a fixed position relative to the axis of the vessel. In that anchored state, the expandable member 301 conforms to the vessel wall at a region of apposition and the region of apposition comprises a substantially cylindrically segment of the vessel wall. The central axis of the expandable member and the central axis of the impeller housing are preferably substantially the same.

The expandable member is configured, in use, to allow the axis of the impeller housing to articulate relative to the axis of the balloon. The articulation of the impeller relative to the balloon preferably comprises two degrees of freedom.

In some embodiments, the expandable member 301 comprises a balloon and the membrane of the balloon comprises an omega shape in cross-section.

The impeller housing 203 may include a tubular member and a wall of the tubular member may include a hole extending through the wall of the tubular member to at least partially define an inflation port for the balloon. Preferably, the inflation port is connected via the catheter to an inflation system exterior of the patient. The connection may include a shaped metal tube or tubing that couples to, and forms a seal with (i.e., "sealingly coupled to") the inflation port. In certain embodiments, the coupling of the expandable member to the impeller housing comprises at least one circumferential seal around the outside diameter of the housing. More preferably, the coupling of the expandable member to the impeller housing comprises a first circumferential seal around the outside diameter of the housing and a second circumferential seal around the outside diameter, with the second circumferential seal spaced apart axially from the first circumferential seal. In some embodiments, the circumferential seal has an axial length and a part of the seal surrounds an inflation port that extends across the walls of the impeller housing and the expandable member. The impeller housing may include an inflation port positioned between the first circumferential seal and the second circumferential seal.

Referencing back to FIG. 2 and FIG. 3, preferably, the balloon has a collapsed state (FIG. 2) for delivery and retrieval and an expanded state (FIG. 3). In some embodiments, in the collapsed state at least a portion of the balloon material can slide relative to an axis of the impeller housing (i.e., is axially slidable relative to the impeller housing). For example, at least a portion of the balloon material may be configured to slide proximally during delivery and to slide distally during retrieval. It may be provided that the balloon comprises a toroidal shape with a first neck and a second neck coupled to the impeller housing. Preferably, a distance between the first neck and the second neck is smaller than the circumference of the toroidal shaped balloon.

A coupling between the expandable member 301 and the impeller housing 203 may include an interfacial layer. For example, the interfacial layer may include an interpenetrating layer. In certain embodiments, the impeller housing comprises interstices and the interpenetrating layer comprises an interpenetration of material of the membrane into the interstices of the impeller housing. The interpenetrating layer may include a tie layer, which may include an acrylate material.

In some embodiments, the expandable member 301 is configured to apply a radial outward force to the vessel wall. The device may be configured such that said application of said outward radial force substantially fixes at least a portion of the impeller housing 203 to a central axis of the vessel. The impeller housing comprises an inner lumen extending from a proximal section of the impeller housing to a distal section of, or outlets of, the housing, the inner lumen configured to house the impeller 205. The impeller housing comprises a first diameter adjacent the proximal section and a second diameter adjacent the distal section. In certain embodiments, a diameter of the inner lumen of the impeller housing varies between said proximal section and said distal section. Similarly, a radial dimension of the impeller blades 206 may vary between said proximal section and said distal section. The diameter of the variation of impeller housing inner lumen diameter may define a tapered, a step, a plurality of steps, a plurality of tapers, a dog bone, a parabola or a combination of these. The impeller blades are configured to be in fluidic engagement with the inner lumen of the impeller housing. Preferably, the impeller blades 206 are configured to be in clearance with the inner lumen of the impeller housing. The impeller assembly 201 has at least one inlet opening and at least one outlet opening. The at least one inlet opening and the at least one outlet opening may be separated by a distance of between 1-40 millimeters. Preferably, the at least one inlet opening and the at least one outlet opening are approximately 5 millimeters apart and may position a proximal end of the impeller 205 approximately 0.5 millimeters from a distal edge of the inlet. This configuration is preferable because it helps minimize recirculation at a transition from inlet to impeller 205. In some embodiments, discussed herein, for example, in FIG. 25, the distance between the inlet and outlet may be extended to the approx. 25-30 millimeters. This configuration provides a more laminar flow into the impeller 205. In other embodiments, the at least one inlet opening and the at least one outlet opening may be approximately 3 millimeters apart to bring the impeller 205 nearer or just inside the inlet. The at least one inlet opening comprises a proximal end and a distal end. A proximal part of the torus extends proximally of the distal end of the proximal inlet opening to define an entry funnel into the inlet opening. The distal portion 115 of the catheter 101 is configured for insertion into a vessel of a patient and the proximal portion 109 of the catheter is configured to extend exterior of the patient.

The proximal portion 109 of the catheter 101 may terminate at the motor housing 401.

Figure 4:
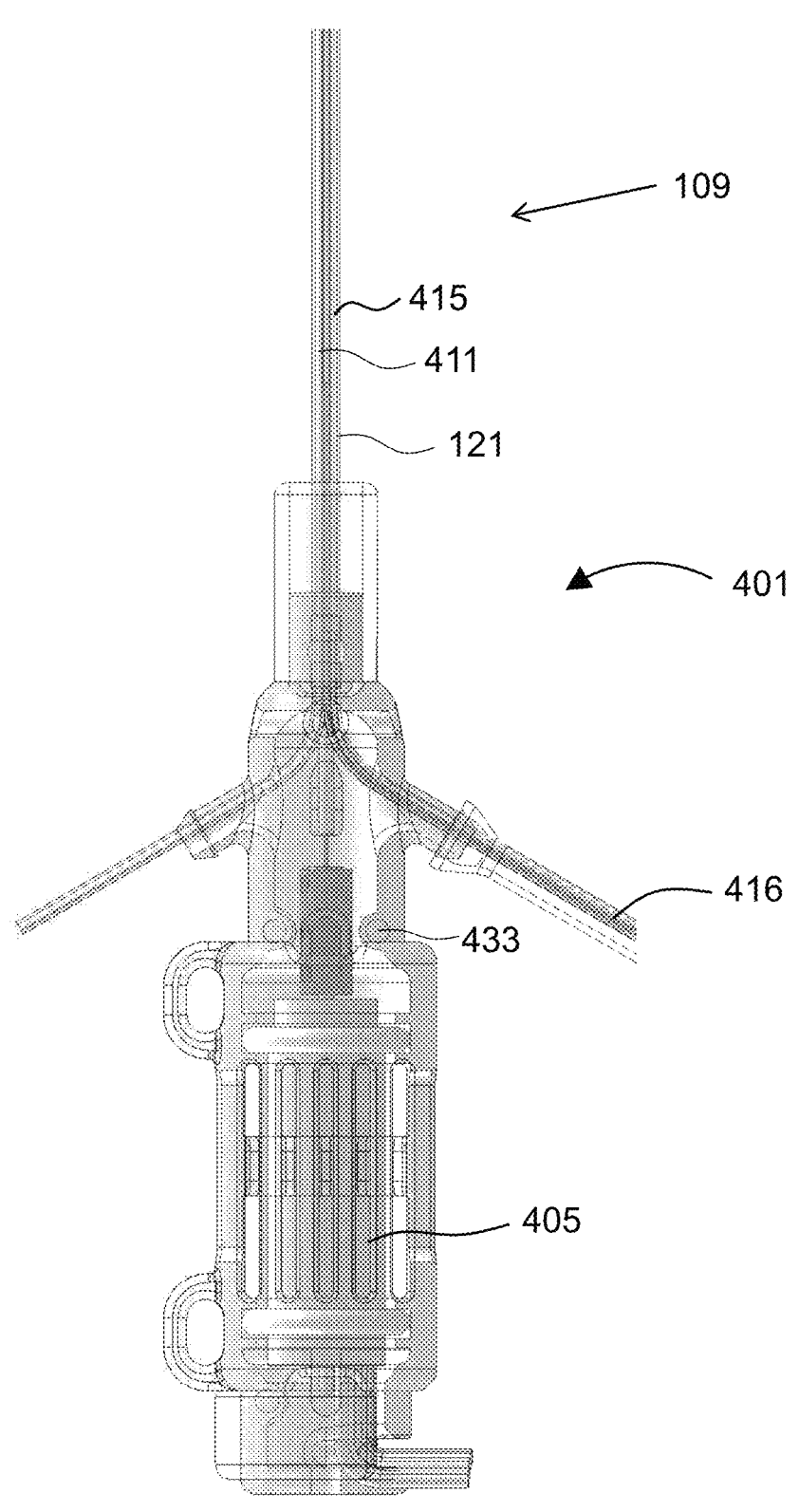
FIG. 4 shows a motor housing connected to the catheter.

FIG. 4 shows a motor housing 401 connected to the proximal portion 109 of the catheter 105. A motor 405 is disposed within the motor housing 401. A drive cable 411 extends through the catheter 105 from the motor 405 to the impeller. In preferred embodiments, an inflation lumen 415 extends along the catheter 105 to the expandable member 301. The drive cable 411 preferably extends through a sleeve within the catheter 101, such as an impermeable sleeve 121. In purge-free embodiments, the impermeable sleeve 121 may include a seal at one or both ends to exclude fluids from the drive cable 411. The impermeable sleeve 121 meets the motor housing 401 at the proximal seal 433.

In certain embodiments, the motor 405 includes a rotor operable to rotate at high speed and the catheter 101 includes a drive cable 411 to transmit said rotational speed through the catheter 101 to the impeller 205. The drive cable 411 may be able to transmit a rotational speed of greater than 5,000 rpms to the impeller 205 (e.g., >10,000 rpm, >15,000 rpm, or >20,000 rpm). Most preferably, the catheter is configured for heatless operation while transmitting high rotational speeds to the impeller.

The impermeable sleeve 121 may include a material such as polytetrafluoroethylene (PTFE). For example, the impermeable sleeve 121 may be provided by thick-walled PTFE tubing. The thick-walled PTFE tubing may have a wall thickness of greater than 75 micrometers, preferably >100 microns, >125 microns, or greater than 150 microns. Optionally, the drive shaft has a second moment of area with a value. The drive cable 411 may include a cylindrical super-elastic member over at least a portion of the length of the drive shaft. The clearance between the drive shaft may be less than a certain number of micrometers. In some embodiments, the impermeable sleeve 121 comprises hydrophobic material. The impermeable sleeve 121 may include a material with a Hildebrand solubility parameter ($\delta$) of less than 16 MPa^(0.5). The impermeable sleeve 121 may include a material with a Hildebrand solubility parameter of less than 14 MPa^(0.5). For example, $\delta$ of nylon is about 15.7 Mpa^0.5; $\delta$ of polytetrafluoroethylene (PTFE) is about 6.2 MPa^0.5. The impermeable sleeve 121 may include a PTFE material, and the drive cable 411 may include a nitinol rod and a gap between the rod and the sleeve may be less than a few microns. Preferably, a concentricity of the rod is greater than 95%. The drive cable may have a first diameter and a second diameter, with the first diameter being slightly larger than the second diameter. The impermeable sleeve may include a polymer material with a dynamic coefficient of friction of less than 0.08, or less than 0.07, 0.06, or 0.05.

Devices of the disclosure are useful for treating edema or congestive heart failure. Using a device of the disclosure, one may operate a pump to promote flow in an innominate vein, resulting in a decrease in pressure at an output of a lymphatic duct, which drains lymph from the lymphatic system. To compensate for what would otherwise be changes in pressure in the circulatory system that would result from operating the pump, the disclosure provides methods to compensate for a pressure change.

FIG. 5 shows steps of a method 501 of using the device 101 for treating edema. The method 501 includes inserting 510 the distal portion 115 of the catheter 105 into an innominate vein 939 of a patient, operating 515 the impeller, and expanding 517 the expandable member 301 to thereby decrease pressure at a lymphatic duct 907.

The method 501 may include the use of a device 101 that includes a catheter 105 with a proximal portion 109 and a distal portion 115, the distal portion 115 dimensioned for insertion into a lumen of a patient. The device 101 includes a pump (e.g., an impeller assembly 201) and an expandable member 301 connected to the pump. When expanded, the expandable member 301 comprises a toroidal shape, in which a proximal surface of the toroidal shape directs fluid into the impeller housing 203. Preferably, an inner radius of the toroidal shape is substantially the same as a radius of the proximal end of the impeller housing 203. In some embodiments, the expandable member 301 comprises an inflatable balloon mounted on the pump. The pump comprises an impeller housing 203 with an impeller therein, with the balloon mounted around at least a portion of a proximal end of the impeller housing 203. The impeller housing 203 may include a distal portion and a proximal portion, with an external diameter of the proximal portion being smaller than an external diameter of the distal portion. The expandable member 301, when not expanded, is disposed around the proximal portion of the impeller housing 203. When the balloon is inflated, a surface of the torus is attached to a surface of the impeller housing 203. When the expandable member 301 is not expanded, the distal portion 115 of the catheter 105 may be passed through a 12 Fr introducer sheath.

Figure 6:
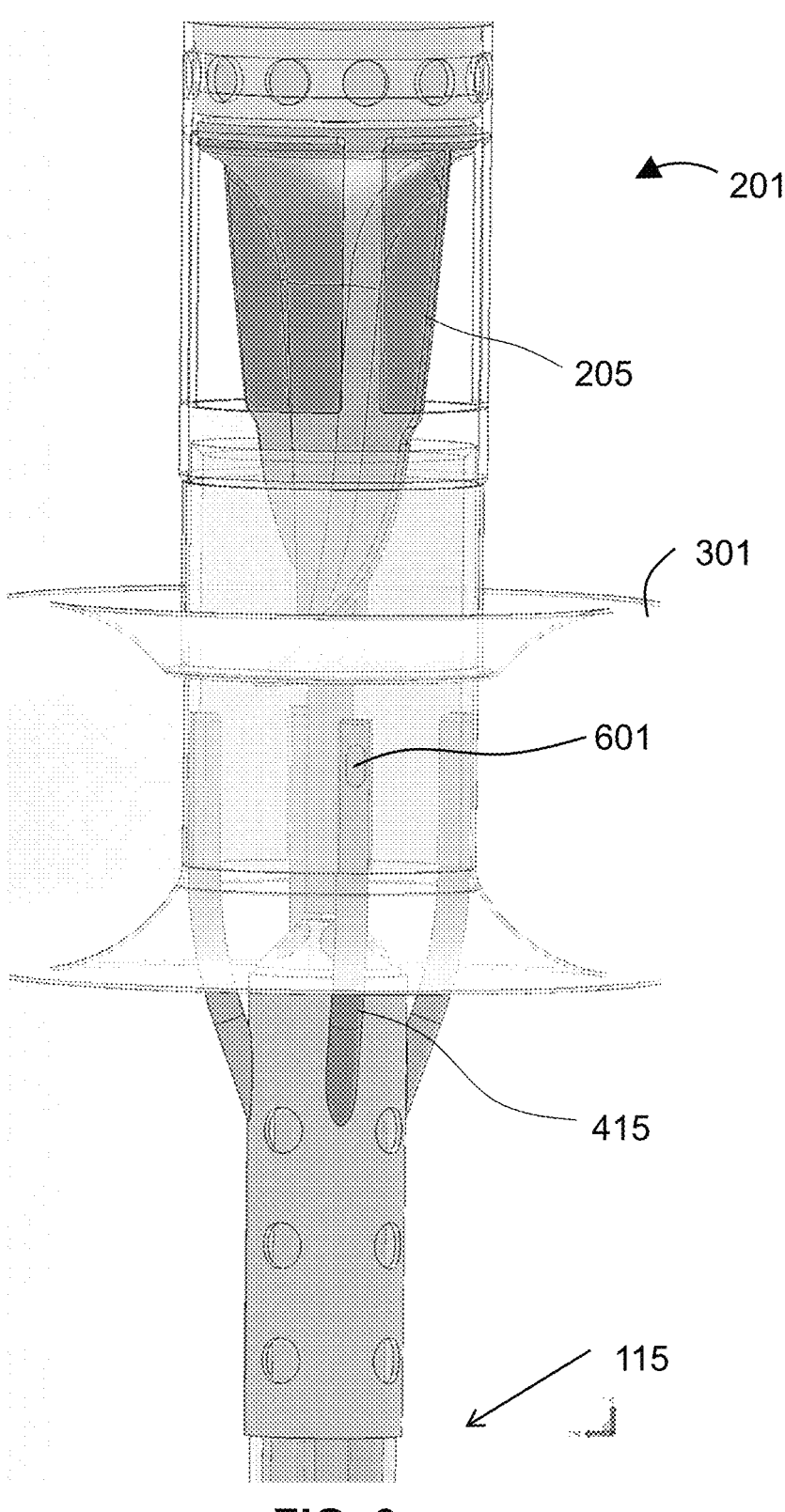
FIG. 6 is a detail view of the impeller assembly with the expandable member in a deployed state.

FIG. 6 is a detail view of the impeller assembly 201 with the expandable member 301 in a deployed state. The impeller 205 sits substantially within and/or just downstream of the deployed restrictor. An inflation lumen 415 extends through the distal portion 115 of the catheter and terminates at port 601 into the expandable member 301. Visual inspection of a surface of the expandable member 301 on a proximal side and an inner surface of the impeller housing 203 reveals that those surfaces form a smooth continuous surface that funnels fluid, under an impelling power of the impeller, through the impeller housing 203. This drives blood through blood vessels and modulates fluid pressure in the vicinity. When operated substantially within an innominate vein, pressure at an outlet of a lymphatic duct decreases, which promotes the drainage of lymph and relief from edema.

FIG. 7 diagrams a method 701 for treating edema. The method 701 includes operating 710 a pump to increase flow through an innominate vein 939 of a patient and—subsequent to the operating step—deploying 717 a restrictor upstream of the pump to thereby restrict flow from a jugular vein to the innominate vein 939 in order to balance 729 pressure downstream of the pump. The method 701 may include operating the pump and then restricting the flow once the increased flow through the innominate vein 939 affects pressure in the jugular vein.

The method 701 preferably includes sensing 715, with a pressure sensor 805, an increase in pressure in the jugular vein that results from the increased flow and restricting the flow in response to sensing the increased pressure in the jugular vein.

Figure 8:
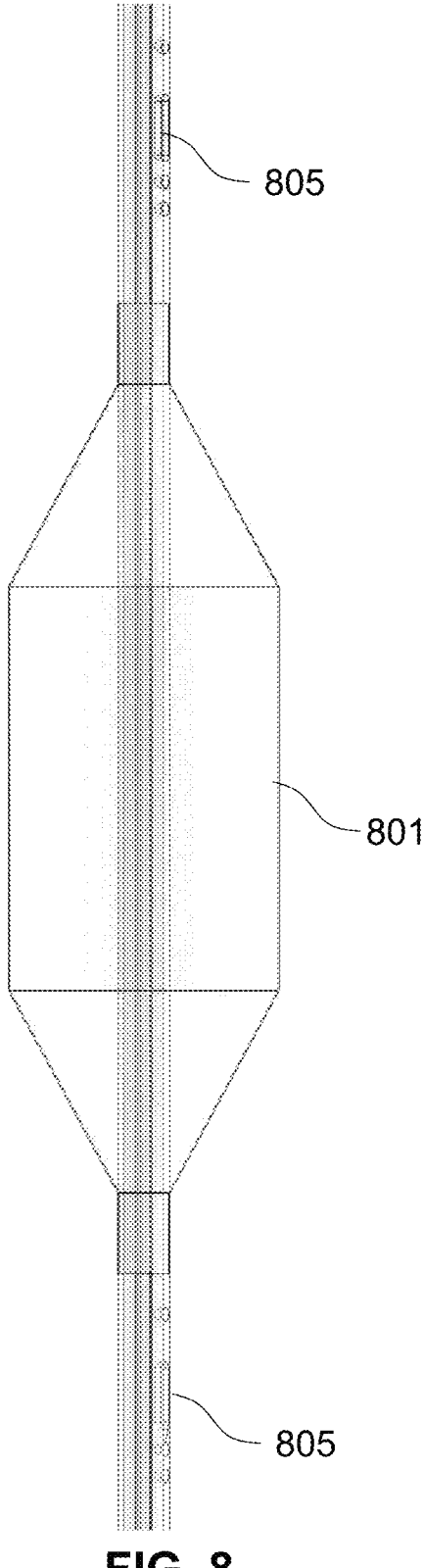
FIG. 8 shows the restrictor and a pressure sensor for the balance and compensation method.

FIG. 8 shows the restrictor 801 and a pressure sensor 805. In fact, as shown in FIG. 8, the device 101 includes pressure sensors 805 along the catheter 105 at locations both proximal and distal to the restrictor 801. In the depicted embodiment, the pressure sensors 805 include pressure sensing lumens extending along the catheter 105 and terminating at the skive-cut sensing apertures along the side of the catheter 105. The sensing lumens extend proximally along the catheter to the motor housing 401, where the sensing lumens preferably exit the housing 401 and make fluidic contact with a mechanical pressure sensor device such as a piezoelectric pressure sensor. The interior of the pressure sensing lumens preferably establish at least substantial hydrostatic equilibrium from the skive-cut sensing apertures along the side of the catheter 105 to the mechanical pressure sensor devices such that a reading from the sensing device(s) is informative of pressure in an area around the restrictor 801. Thus the pressure sensors 805 provide information that can feedback into the method 701 and be used as information to control deployment 717 of the restrictor 801. The method 701 preferably includes inserting 705 the device 101 comprising the pump into vasculature of a patient prior to the operating 710 step.

Figure 9:
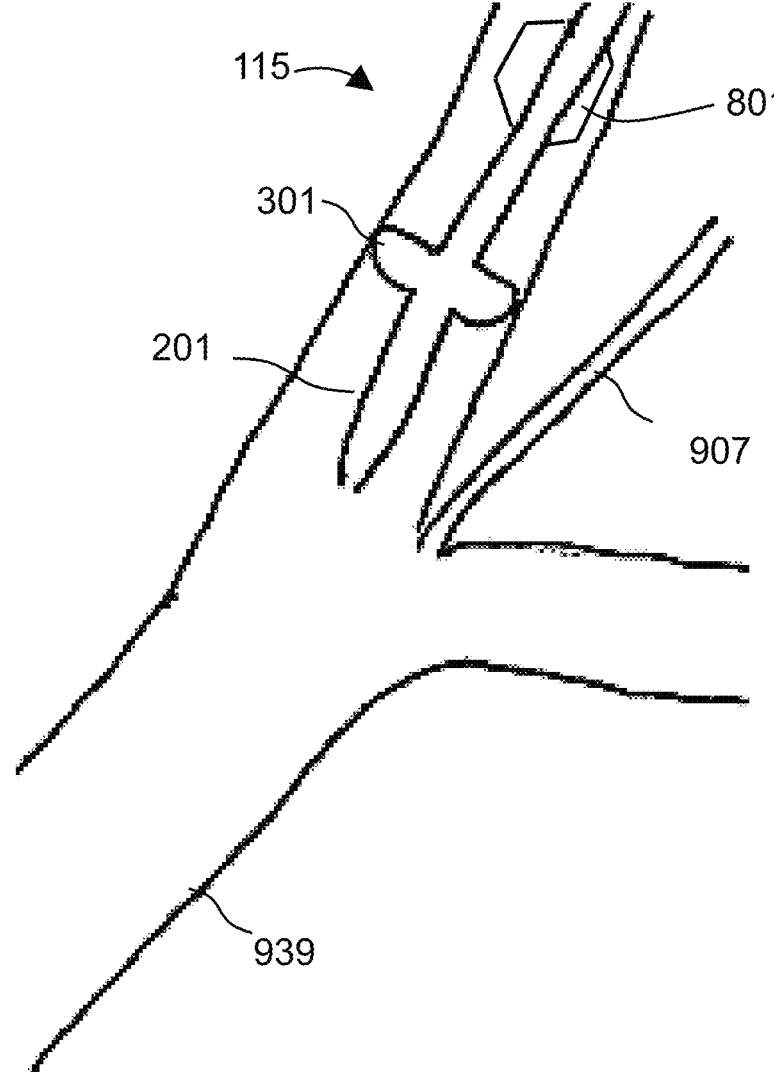
FIG. 9 shows a device inserted into vasculature of a patient.

FIG. 9 shows a device 101 inserted 705 into vasculature of a patient. The device 101 comprises a catheter 105 dimensioned to be at partially implanted within the vasculature and the pump comprises an impeller assembly 201 disposed at a distal portion 115 of the catheter 105. The distal portion 115 is inserted through the jugular vein and down and into the innominate vein 939. Preferably a proximal portion 109 of the catheter 105 is connected to a motor housing 401 and the device 101 one or more pressure sensor 805 and the deployable restrictor 801 attached to the catheter 105 proximal to the pump.

Once the impeller assembly is at least partially within the innominate vein 939, the impeller 205 is spun, which pumps blood through the impeller housing 203. This causes a decrease in pressure around an outlet of a lymphatic duct 907. The decrease in pressure causes lymph to drain from the lymphatic duct 907 and into the circulatory system. That drainage of lymph relieves edema or alleviates congestive heart failure. The method 701 further includes deploying 717 a restrictor 801 upstream of the impeller assembly 201 to thereby restrict flow from a jugular vein to the innominate vein 939 in order to balance 729 pressure downstream of the impeller assembly 201. The method 701 may further include sensing 715 pressure and adjusting 735 restriction of the flow according to pressure sensed 715 via one or more of the pressure sensors 805.

In some embodiments, the restrictor 801 includes an inflatable balloon and restricting 717 the flow includes inflating the restrictor. Optionally the sensing 715 is performed using a computer system communicatively connected to the pressure sensor(s) 805. The method 701 may include periodically or continually adjusting 735 inflation of the restrictor according to the sensed pressure.

FIG. 10 diagrams a related method 1001 for treating edema. The method 1001 includes inserting 1005 a pump into an innominate vein and operating 1010 the pump to increase flow through an innominate vein 939 of a patient. A pressure change in a jugular vein of the patient that results from the increased flow is sensed 1015, and a restrictor 801 is adjusted 1029 to restrict flow from the jugular vein to the innominate vein 939 based on the sensed pressure. Preferably, the method 1001 includes inserting 1005 a catheter 105 into the innominate vein 939. The catheter 105 comprises the pump, a pressure sensor 805, and the restrictor 801. The restrictor may include an inflatable balloon and adjusting 1029 the restrictor may include at least partially inflating and/or deflating the balloon. The sensing 1015 may be performed using the pressure sensor 805. The method 1001 preferably includes periodically or continually adjusting inflation of the restrictor according to the sensed pressure. The method 1001 may include adjusting 1029 the inflation in order to balance pressure downstream of the pump. In preferred embodiments, the pump comprises an impeller assembly 201 disposed at a distal portion 115 of the catheter 105. A proximal portion 109 of the catheter 105 is connected to a motor housing 401 having a motor 405 therein operably coupled to the impeller assembly. In certain embodiments, the catheter 105 is coupled to a computer system operable to read the pressure or control the inflation.

Aspects and embodiments of the disclosure relate to a purge-free system, which may be understood to refer to or include methods and devices for the treatment of edema that do not use a purge system or a purge liquid.

Figure 11:
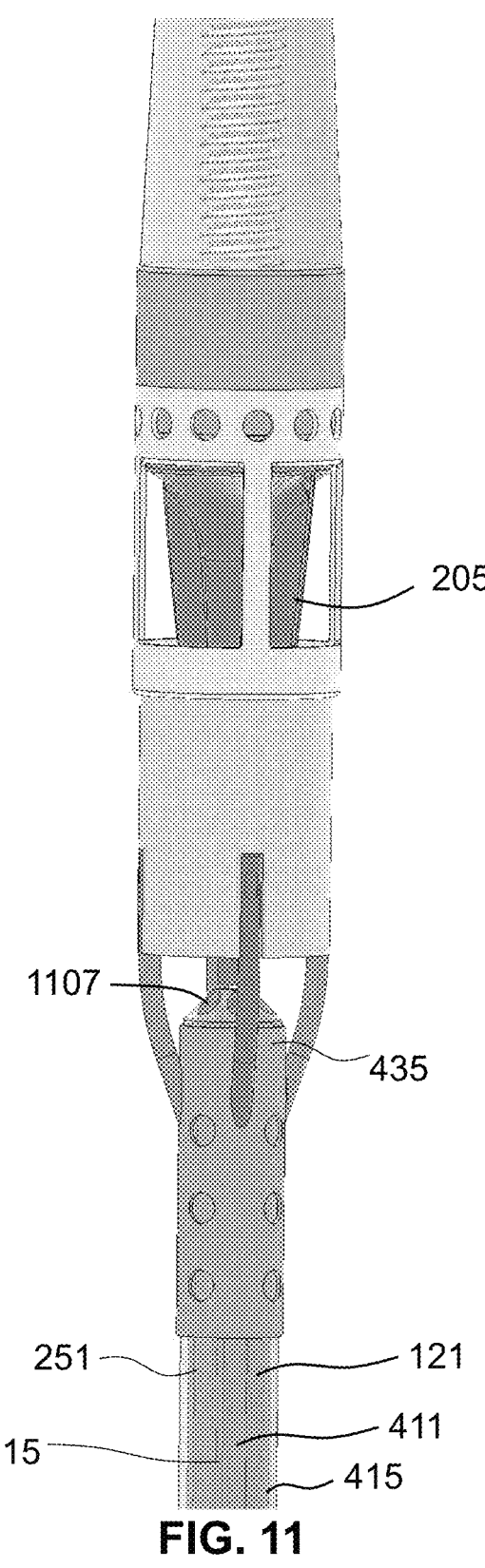
FIG. 11 is a detail view of features that provide for a purge-free system.

FIG. 11 is a detail view of features that provide for a purge-free system. The purge-free system may be provided by a device 101 that includes a catheter 105 comprising a proximal portion 109 and a distal portion 115, an impeller 205 connected to the distal portion 115 of the catheter 105, a motor 405 connected to the proximal portion 109 of the catheter 105, a drive cable 411 extending through the catheter 105 from the motor 405 to the impeller 205, and an impermeable sleeve 121 extending through the catheter 105 over the drive cable 411.

The sleeve 121 has a distal seal 435 at the impeller. With reference back to FIG. 4, the sleeve 121 may have a proximal seal 433 at the motor 405. Due to the sleeve 121 and at least the distal seal 435, a body fluid external to the impermeable sleeve 121 is prevented from entering the impermeable sleeve 121 and contacting the drive cable 411. The sleeve 121 and at least the distal seal 435 exclude fluid from the drive cable 411.

With reference back to FIG. 4, the proximal seal 433 (see FIG. 4) may include one or more O-rings. Similarly, the distal seal 435 between the sleeve 121 and the drive cable 411 may be provided by an O-ring, or a collar or press-fit, or extended, friction-fit tube. Any suitable seal may be included that prevents blood or bodily fluid from entering the sleeve and making contact with the drive cable 121. The drive cable 121 may be provided by any suitable material including, for example, a nickel-titanium alloy or a braided steel cable. Contact with blood would present a risk of hemolysis or clotting that could interfere with an ability of the drive cable 411 to rotate freely (e.g., at >5,000 rpm) within the sleeve 121 and within the catheter 105. The sleeve excludes blood and thus obviates concerns about clotting or hemolysis, allowing the drive cable 411 and impeller 205 to operate freely without impediment.

Embodiments of the device 101 may include multiple lumens. For example, the device 101 may include a first and second inflation lumen 415 (or a single inflation lumen 415). The device may include a medicament lumen 251 extending through the catheter 105. In preferred embodiments, the device 101 includes at least a first inflation lumen 415 and a second inflation lumen 415, both extending through the catheter 105. The first inflation lumen 415 and the second inflation lumen 415 have respective first and second proximal ends 416 (see FIG. 1) accessible outside of the motor housing 401. The first lumen and the second lumen are preferably symmetrically disposed about the drive cable 411 to impart balance to the device 101. As shown, the catheter 105 does not include a purge system or a purge fluid.

With reference back to FIGS. 1 and 3, the device 101 may include an impeller 205 sitting in an impeller housing 203. The device 101 includes at least a first expandable member 301 connected to the distal portion 115 of the catheter 105. The first expandable member 301 may be connected to the impeller housing 203, wherein the device 101 further comprises a second expandable member 801 disposed along the catheter 105. The first expandable member 301 may use a toroidal balloon connected directly to a surface of the impeller housing 203. The device 101 may further include at least one pressure sensor 805 disposed along the catheter 105 proximal to the impeller. In purge-free embodiments, the distal seal 435 may be provided using a fitting 1107 between the impermeable sleeve 121 and a portion of the impeller 205, in which the fitting 1107 excludes fluids and allows the impeller 205 and drive cable 411 to rotate within the device 101. The depicted device 101 is useful for the treatment of edema, and may be characterized as a purge-free device. The purge-free device may be used in a method of treating edema.

Figure 12:
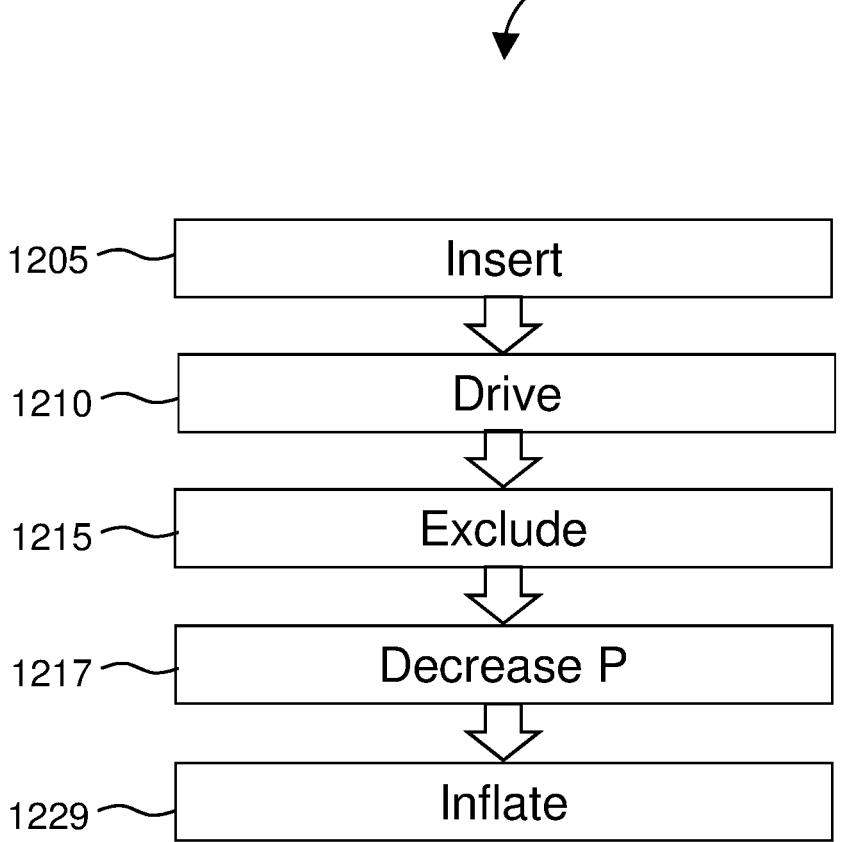
FIG. 12 diagrams a method of treating edema using a purge-free device.

FIG. 12 diagrams a method 1201 of treating edema using a purge-free device. The method 1201 includes inserting 1205 into an innominate vein 939 of a patient a distal portion 115 of a catheter 105 and driving 1210 an impeller 205 connected to the distal portion 115 of the catheter 105 by means of motor 405 at a proximal portion 109 of the catheter 105. The motor 405 is connected to the impeller 205 by a drive cable 411 extending through the catheter 105, to thereby decrease pressure 1217 at a lymphatic duct 907. An impermeable sleeve 121 extends through the catheter 105 over the drive cable 411 such that body fluid external to the impermeable sleeve is prevented from entering the impermeable sleeve and contacting the drive cable. The impermeable sleeve 121 and at least the distal seal 435 exclude 1215 fluid from entering into the impermeable sleeve 121 and making contact with the drive cable 411.

The method 1201 may include inflating 1229 a restrictor disposed along the distal portion 115 of the catheter 105 to restrict flow from a jugular vein into the innominate vein 939. The inflation 1229 may be performed using an inflation lumen 415 extending through the catheter 105 outside of the impermeable sleeve 121. In some embodiments, blood and bodily fluid is excluded 1215 from the drive cable 411 using a repulsive gap between the drive cable 411 and the impermeable sleeve 121. For example, the repulsive gap may include a hydrophobic material (PTFE) on one side of the gap, a smooth metallic shaft 411 on the other and a gap dimension that prevents influx of blood components. For example, a gap dimension of about 0.5 μm should prevent influx of red blood cells, leukocytes, and platelets. It may be found that a gap dimension of 0.1 μm excludes 1215 all blood and bodily fluid. The drive cable 411 may not lie concentric with the sleeve 121 so preferably the gap dimension is the largest gap between the two.

The decreased pressure at a lymphatic duct 907 promotes drainage from a lymphatic system into a circulatory system. Preferably, the impermeable sleeve 121 comprises a proximal seal 433 at a housing of the motor 405 and a distal seal 435 at the impeller 205. The proximal seal 433 prevents the blood and bodily fluid from escaping the patient through the motor housing 401 or the proximal portion 109 of the catheter 105. In some embodiments, the distal seal 435 comprises a fitting between the impermeable sleeve and a portion of the impeller, wherein the fitting excludes fluids and allows the impeller and drive cable to rotate within the device 101.

The method 1201 may include inflating at least one balloon 301, 801 disposed along the catheter 105 by means of an inflation lumen 415 having a proximal end accessible outside of the motor housing 401 while the distal portion 115 of the catheter 105 is inserted into the innominate vein 939. In various embodiments, the proximal seal 433 uses an O-ring; the impermeable sleeve 121 comprises PTFE; the drive cable 411 comprises a metal such as a nickel-titanium alloy; either or both of balloon 301 and restrictor 801 may comprises polyvinyl chloride, cross-linked polyethylene, polyethylene terephthalate (PET), or nylon; or any combination of the those materials are included. Employing the method 1201, blood and bodily fluid are excluded 1215 from the drive cable 411 without the use of a purge fluid or purge system.

Other features and benefits are provided by or within the scope of the disclosure.

Methods and devices of the disclosure avoid problems with thrombosis or hemolysis that may otherwise interfere with the functioning of mechanical systems or form surface irregularities that lead to other complications. For example, mechanical system may be most beneficial medically when blood clots or other coagulation-related phenomena are avoided. Accordingly, embodiments of devices and methods of the disclosure are provided that inhibit coagulation, thrombosis, hemolysis, or other issues that may present when treating edema.

Certain embodiments provide a device that operates with benefit from an anticoagulant. The device may include a pump (e.g., an impeller assembly) that is washed with a solution or suspension that comprises an anticoagulant such as, for example, heparin. Where the pump or impeller assembly is provided via a catheter, the catheter may include a lumen, reservoir, port, or other such feature to release the coagulant at or near the pump.

Figure 13:
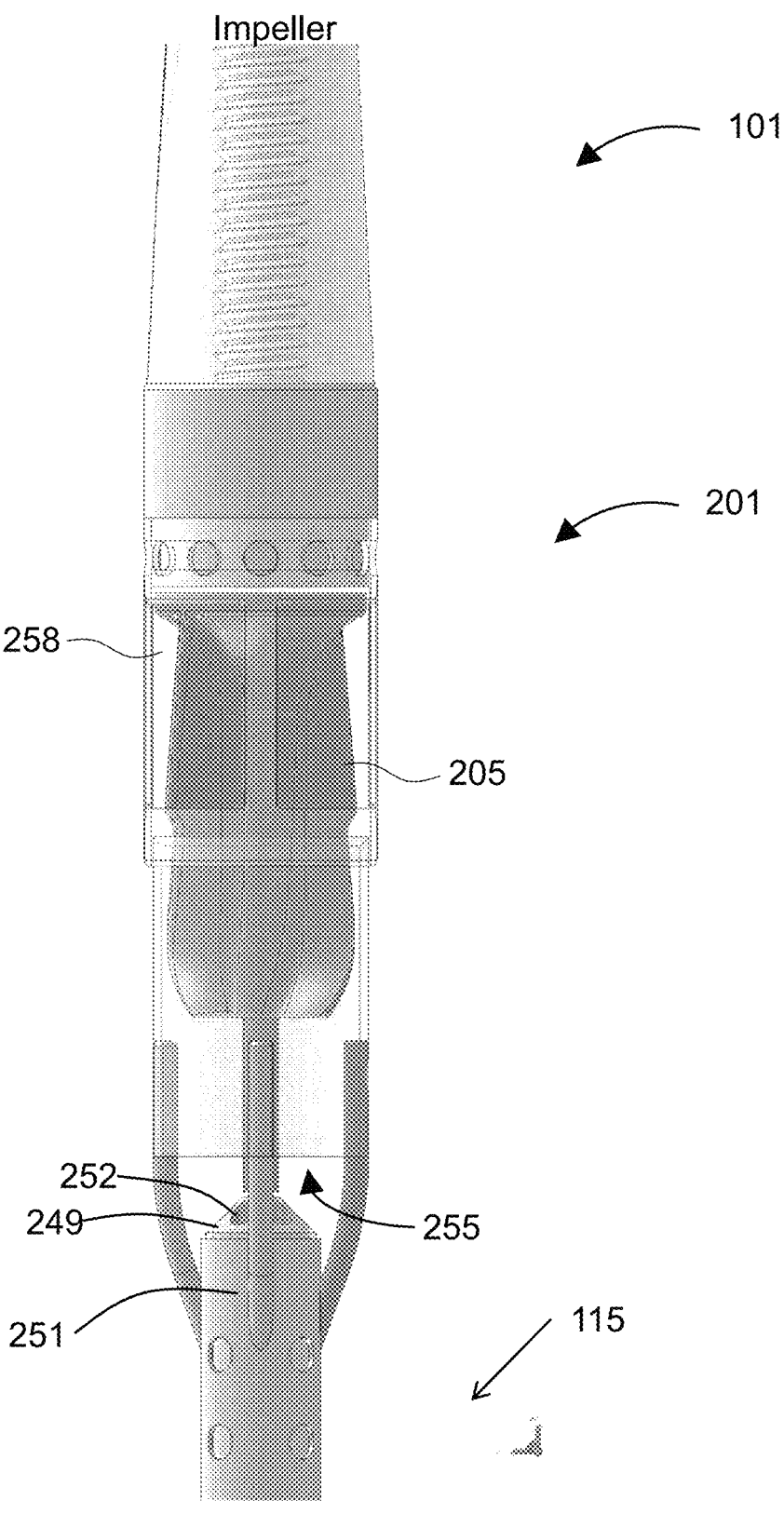
FIG. 13 illustrates a portion of an intravascular device for treatment of edema that releases an anticoagulant at an intravascular pump.

FIG. 13 illustrates a portion of an intravascular device 101 for treatment of edema that releases an anticoagulant at an intravascular pump. The device 101 includes a catheter 105, an impeller assembly 201 mounted at a distal portion 115 of the catheter 105, and a medicament lumen 251 extending through the catheter 105 and terminating substantially at an inlet 255 of the impeller assembly 201. When the device 101 is used (e.g., when the impeller 205 is operated within a blood vessel of a patient), a medicament released from the medicament lumen 251 flows through the inlet 255 and impeller assembly 201. Preferably, the catheter 105 and impeller assembly are dimensioned for insertion through a jugular vein of a patient The device 101 may include a reservoir in fluid communication with the medicament lumen 251. The reservoir may be, for example, a solution bag (aka an "IV bag") on a rack near the treatment gurney and in fluid communication with the medicament lumen 251 (e.g., via a Luer lock).

In certain embodiments of an anticoagulant delivery device 101, the impeller assembly 201 has an impeller housing 203 with an impeller 205 rotatably disposed therein. The device 101 preferably includes a motor 405 connected to a proximal end of the catheter 105 and operably connected to the impeller 205 via a drive cable 411 extending through the catheter 105. The medicament lumen 241 preferably extends through the catheter 105 (e.g., outside of a sleeve 121 surrounding the drive cable 411) and may terminate at a port 252 such that an anticoagulant released therefrom washes the impeller 205 or impeller assembly 201. Preferably, the port 252 is located at the impeller housing 203, proximal to the impeller.

To define the inlets 255, the catheter 105 may include a tube with a drive cable extending there through with a cap 249 connected around a terminal portion of the tube, with the impeller housing 203 mounted to the cap by a plurality of struts to define inlets 255 into the impeller housing 203. In some embodiments, the cap 249 seals a terminus of the flexible tube to a shaft of the impeller, and the port 252 is located in the cap 249. Preferably, the impeller housing 203 includes one or more outlets 258 around a distal portion 115 of the impeller, such that operation of the impeller 205 within a blood vessel drives blood into the impeller assembly 201 via the inlets 255 and out of the impeller assembly via the outlets 258.

The device 101 may include an anticoagulant in the reservoir. When the device 101 is inserted into a blood vessel of a patient and the impeller 205 is operated, the anticoagulant is released from the port 252 in the impeller cage 201 and the released anticoagulant mixes with blood and washes over the rotating impeller 205. Any suitable anticoagulant may be used. For example, the anticoagulant may include one or any combination of heparin, tirofiban, warfarin, rivaroxaban, dabigatran, apixaban, edoxaban, enoxaparin, and fondaparinux. Due to the anticoagulant, the device 101 may be used for the treatment of edema, using the impeller to cause drainage of a lymphatic duct or vessel.

Using such a device, aspects of the invention provide a method for treating edema. The method includes operating a pump to increase flow through an innominate vein 939 of a patient and releasing an anticoagulant at or adjacent an inlet of the pump. The pump may include an impeller 205 in a cage 203 at a distal portion 115 of a catheter 105 and the anticoagulant is released from a port 252 in or adjacent a proximal portion of the cage. Preferably, a proximal end of the catheter 105 terminates at a housing comprising a motor 405, and the motor 405 is operably coupled to the impeller by a drive cable extending through the catheter 105. In this method, the catheter 105 includes a medicament lumen extending therethrough and terminating at the port. This method may include providing the anticoagulant in a reservoir in fluid communication with the medicament lumen; inserting the catheter 105 into vasculature of the patient to position the impeller in the innominate vein 939; operating the motor 405 to drive the impeller; and washing the anticoagulant over the impeller by releasing the anticoagulant from the port. Preferably, this method includes operating the pump decreases pressure at a lymphatic duct 907, thereby draining lymph from a lymphatic system of the patient. The pump may include an impeller on a distal portion 115 of a catheter 105. This method may include releasing the anticoagulant from a port at a proximal portion 109 of the impeller, preventing clotting or thrombosis from interfering with operation of the impeller by the release of the anticoagulant, or both. The anticoagulant may include heparin, warfarin, rivaroxaban, dabigatran, apixaban, edoxaban, enoxaparin, or fondaparinux. Using a restrictor 801, 301, the method may include restricting flow from a jugular vein to the innominate vein 939 to thereby promote flow from a subclavian vein to the innominate vein 939.

Figure 16:
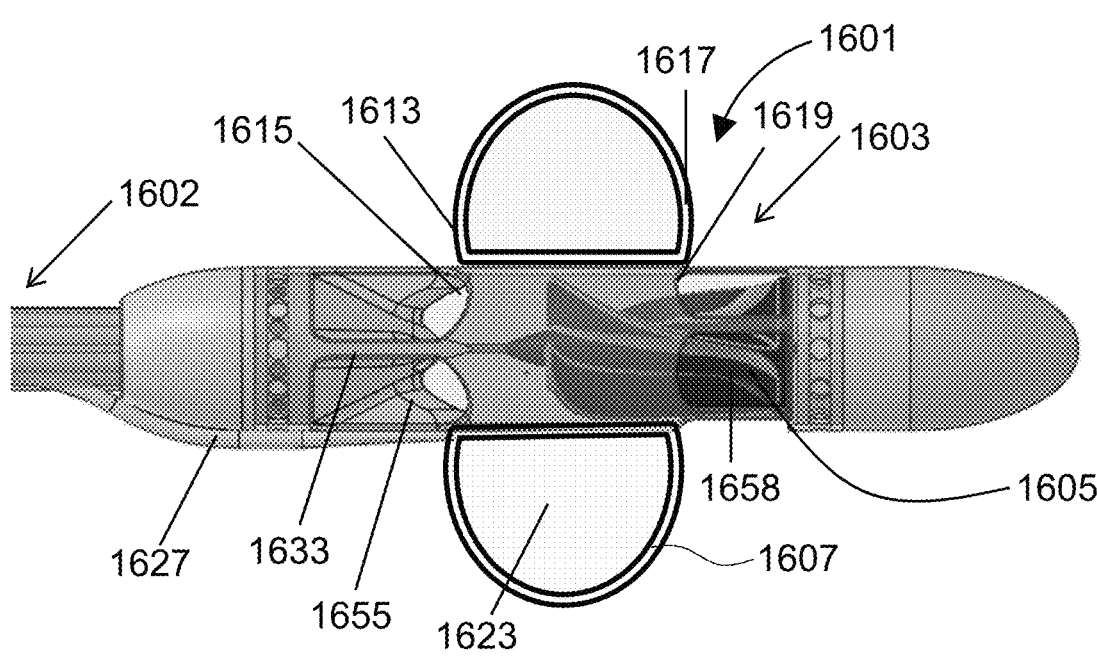
FIG. 16 is a partial cutaway view of an impeller assembly.

FIG. 16 is a partial cutaway view of an impeller assembly 1601. The impeller assembly 1601 includes an impeller housing 1603 with an impeller 1605 rotatably disposed therein. An expandable member 1607 is attached to an outside of the impeller housing 1603. The expandable member 1607 is depicted in an expanded state.

The impeller assembly 1601 is may be designed to facilitate a blood flow through the impeller housing 1603. To facilitate blood flow, the impeller housing 1603 may include proximal inlets 1655. Preferably, the impeller housing 1603 includes at least four proximal inlets 1655. The proximal inlets 1655 may be substantially rectangular and may include rounded corners. The impeller assembly 1601 may also include distal outlets 1658. For example, the impeller assembly 1601 may include four to five distal outlets 1658. Preferably, the proximal inlets 1655 and distal outlets 1658 include substantially rounded features, such as, rounded corners. Rounded features are preferable because rounded features provide smooth contact surfaces for blood that flows through the impeller housing 1603. This may reduce incidences of damage to particles in blood, e.g., blood cells, that occurs when blood strikes a sharp surface.

In preferred embodiments, an expandable member 1607 is attached to an outer surface of the impeller housing 1603. The expandable member 1607 may comprise a shape that facilitates a flow of blood into the impeller housing 1603 when the expandable member 1607 is in an expanded state. In some embodiments, the expandable member 1607 forms a D shaped ring around a circumference of the impeller housing 1603. In other embodiments, the expandable member 1607 forms an Omega shaped ring around a circumference of the impeller housing 1603. In other embodiments, the expandable member 1603 forms a substantially circular ring around the impeller housing 1603.

In an expanded state, a proximal face 1613 of the expandable member 1607 may be substantially aligned with a distal portion 1615 of the proximal inlets 1655. A distal face 1617 of the expandable member 1607 may be substantially aligned with the proximal extent 1619 of the distal outlets 1658.

In preferred embodiments, the expandable member 1607 comprises an elastomeric membrane, for example, a polyurethane membrane. The expandable member 1607 may be a balloon. The balloon may comprise a low durometer material, for example, a durometer of <80 shore D hardness, or <70 shore D hardness, or less than 60 shore D hardness, or between 60 shore A hardness and 60 shore D hardness.

The expandable member 1607 may include a fluidically sealed space, i.e., an inflation space 1623, that is radially expandable relative to the impeller housing 1603. The impeller assembly 1601 may include an inflation tube 1627 connecting the inflation space 1623 to a lumen of the catheter 1602. The inflation tube 1627 may extend between the catheter 1602 and the inflation space 1623, for example, parallel to a proximal strut 1633. The inflation tube 1627 may extend exterior of the proximal strut 1633 (as shown). Alternatively, the inflation tube 1627 may extend interior to the proximal strut 1633. The inflation tube 1627 may connect with the inflation space 1623 by extending through a wall of the expandable member 1607. Alternatively, the inflation tube 1627 may connect with the inflation space 1623 by extending through an interface between the expandable member 1607 and the impeller housing 1603, or by extending through a wall of impeller housing 1603. The fluidically sealed space 1623 may comprise an inflation port for expanding the expandable member 1607.

The inflation tube 1627 may comprise an outer surface and a lumen. The inflation tube 1627 preferably provides a sealingly penetrate into the inflation space 1623. The penetration of the inflation tube 1627 into the inflation space 1623 may comprise a seal of the region of penetration. The seal may comprise a melting or bonding operation.

Figure 17:
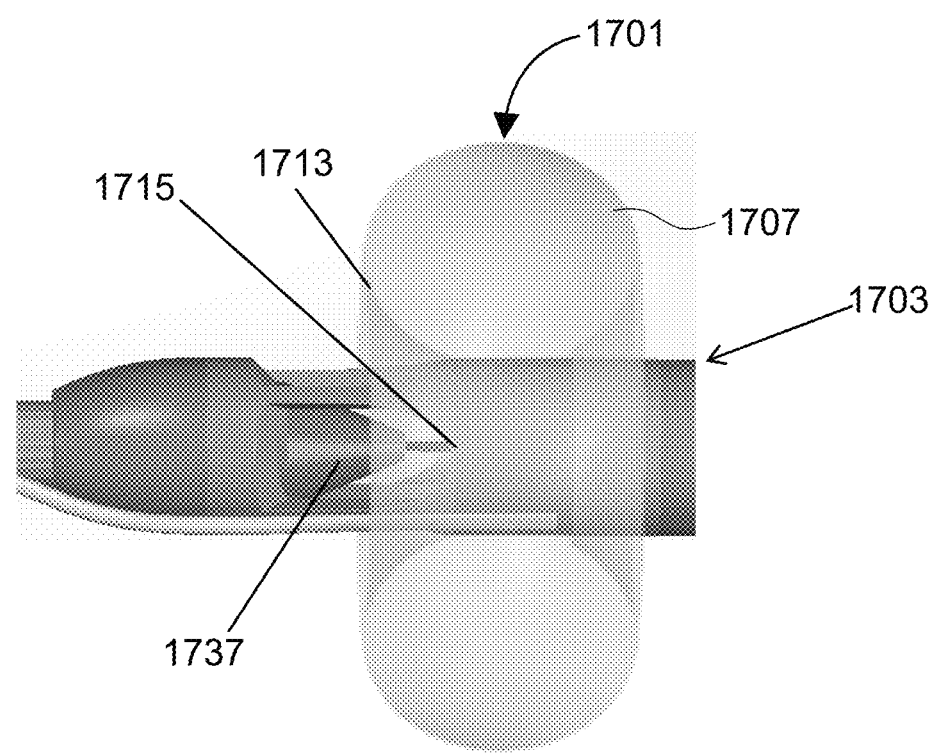
FIG. 17 is a side view of an impeller assembly.

FIG. 17 is a side view of an impeller assembly 1701. An expandable member 1707, e.g., a balloon, is attached to an outer surface of an impeller housing 1703. The expandable member 1707 may be substantially torpid in shape. The expandable member 1707 is depicted with muted lines to reveal structures beneath the expandable member 1707. A proximal face 1713 of the expandable member 1707 extends over a distal inlet region 1715. In this configuration, the proximal face 1713 of the expandable member 1707 provides a funnel to converge blood flow towards inlets of the impeller housing 1703 thereby facilitating blood flow through the device.

The impeller assembly 1701 is dimensioned for inserting into an innominate vein. The expandable member 1707 is dimensioned such that in a deployed state, the expandable member 1707 opposes walls of the innominate vein to impede, guide, or direct a flow of blood into the impeller housing 1703. In some embodiments, an inner diameter of the expandable member 1707 is substantially equivalent to the outer diameter of the impeller housing 1703. The inner diameter of the expandable member 1707 may extend over a portion of the proximal inlets. This arrangement helps funnel blood into the impeller assembly 1701 without the distal edge of the inlets disrupting blood flow. In some embodiments, the proximal inlets are substantially D shaped with rounded features to prevent shearing of blood cells.

The expandable member 1707 may comprises a bonded region, the bonded region comprising a substantially cylindrical section where the expandable member 1707 is bonded to the impeller assembly 1701. In some embodiments, the inlet region may comprise a conical element 1737 coaxial with the impeller. The conical element 1737 may be proximal to the impeller and may be configured to minimize flow recirculation regions.

Figure 18:
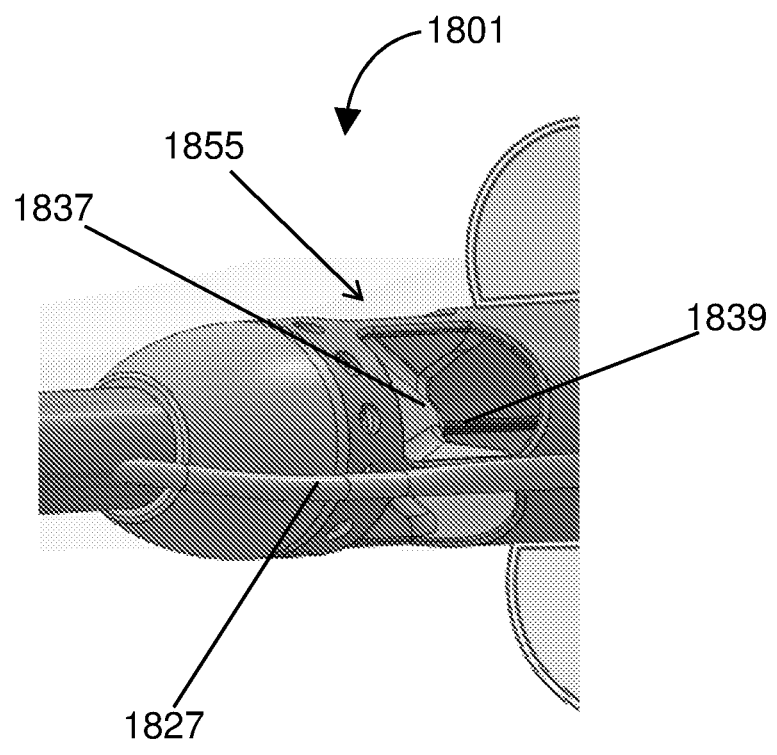
FIG. 18 shows an exemplary inlet region of an impeller assembly.

FIG. 18 shows an exemplary inlet region 1855 of an impeller assembly 1801. The inlet region 1855 comprises a conical element 1837 with flow directing features projecting radially outward from a surface of the conical element 1837. The flow directing features may be aligned with proximal struts. A drive element 1839 may extend through the conical element 1837 and connect with an impeller disposed inside the impeller assembly 1601. In the shown embodiment, an inflation lumen 1827 is exterior of the impeller assembly 1801.

Figure 19:
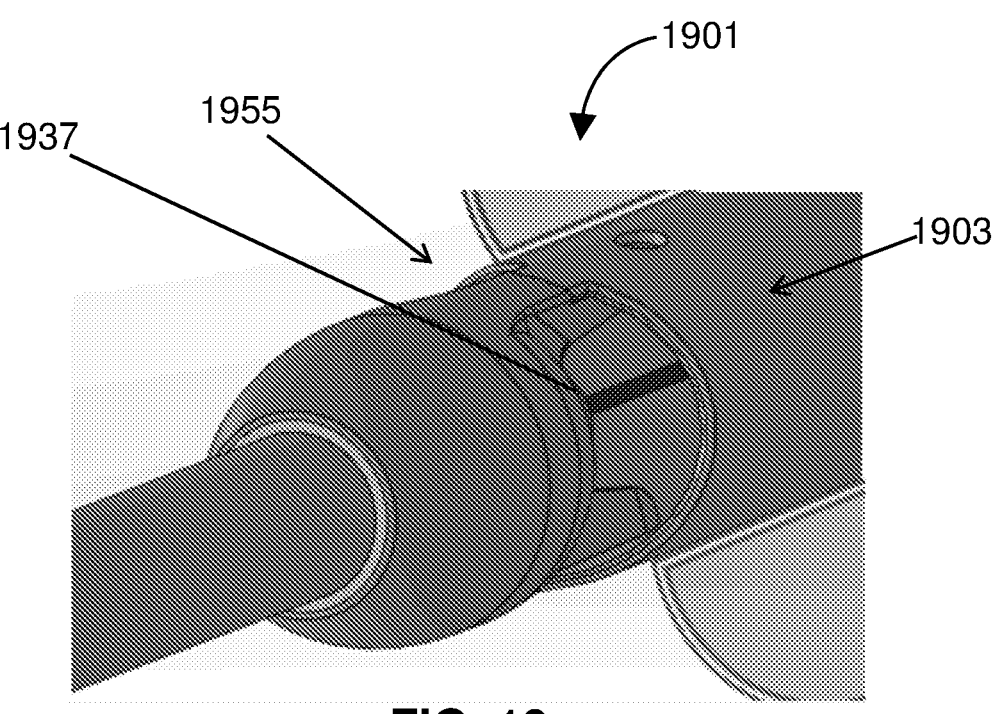
FIG. 19 shows an inlet region with an internal inflation lumen.

FIG. 19 shows an inlet region 1955 with an internal inflation lumen. The inflation lumen is internal to the impeller housing 1903. The inflation lumen may connect to and extend through the conical element 1937. The inflation lumen may, for example, extend through a wall of the impeller housing 1903. Alternatively, the inflation lumen may be interiorly located within the impeller housing 1903.

Figure 20:
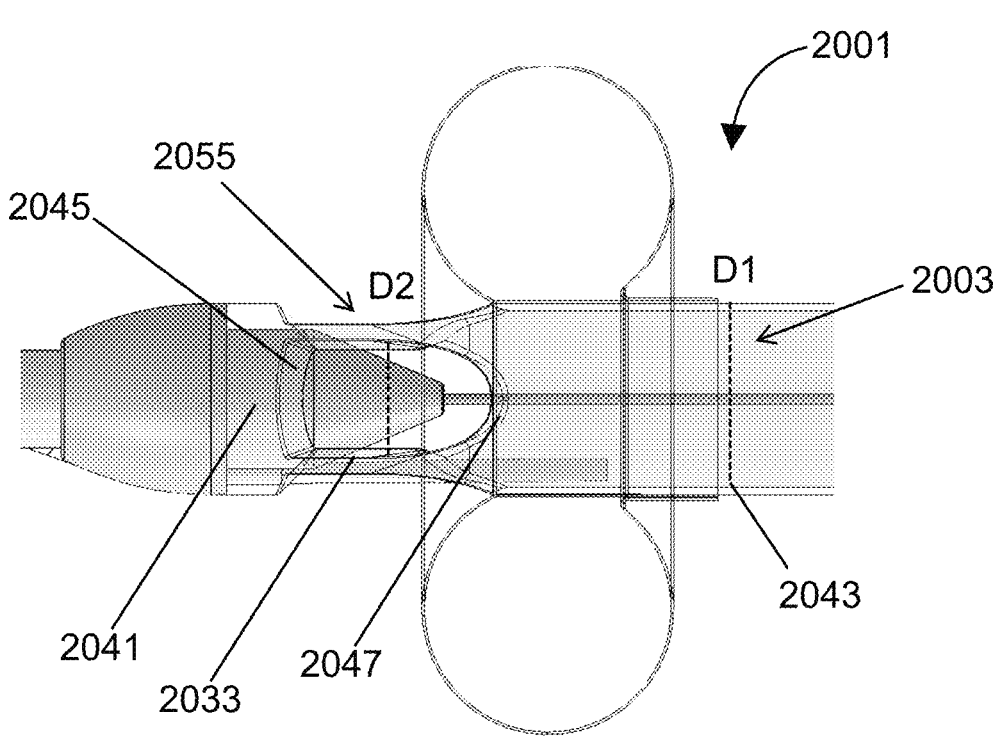
FIG. 20 is a detailed view of a proximal inlet.

FIG. 20 is a detailed view of a proximal inlet 2055. The proximal inlet 2055 is defined by proximal struts 2033. The proximal struts 2033 extend parallel to one another connecting a proximal portion 2041 of the impeller housing 2003 to a distal portion 2043 of the impeller housing 2003. The proximal struts 2033 are designed such that when the catheter is operating inside a patient's body, the proximal struts 2033 may separate and direct a flow of blood into the impeller housing 2003 without inducing a recirculation flow pattern. The proximal struts 2033 may include a proximal and distal rim 2045, 2047. The proximal struts 2033 and rims 2045, 2047 may, for example, define a generally rectangular inlet region 2055. In some embodiments, the generally rectangular inlet region 2055 comprises a curved rectangular inlet. The curved rectangular inlet may have, for example, a bevel around at least a portion of a rim 2045, 2047 of the inlet 2055. The bevel may provide a gentle transition region for blood to flow into the impeller housing 2003.

In some embodiments, the proximal struts 2033 comprise a substantially constant width along a length of the proximal strut 2033. In other embodiments, the width of the proximal struts 2033 may vary, for example, the width of the proximal struts 2033 may be greater at a proximal end than at a distal end, or vice versa. The proximal struts 2033 may comprise a first wall thickness and a second wall thickness, wherein said first wall thickness is greater than said second wall thickness. In some embodiments, the proximal struts 2033 may comprise a tapered wall thickness.

Preferably, the impeller housing 2003 is substantially cylindrical in shape for easy passage through an innominate vein. The impeller housing 2003 may comprise a plurality of inner diameters for manipulating a flow of blood through the impeller housing 2003 and such that the flow of blood experiences minimal disturbances such as recirculation or vortices within, or near, the impeller assembly 2001. For example, the impeller housing 2003 may comprise a first inner diameter D1 and at least a second inner diameter D2 wherein the first inner diameter is greater than said at least second diameter. In some embodiments, the impeller housing 2003 may comprise stepped portions defined by changes in inner diameters. In some embodiments, the impeller housing 2003 may comprise, for example, a tapered diameter, defined by a diminished or reduced internal diameter along the length of the impeller housing 2003 toward one end.

Figure 21:
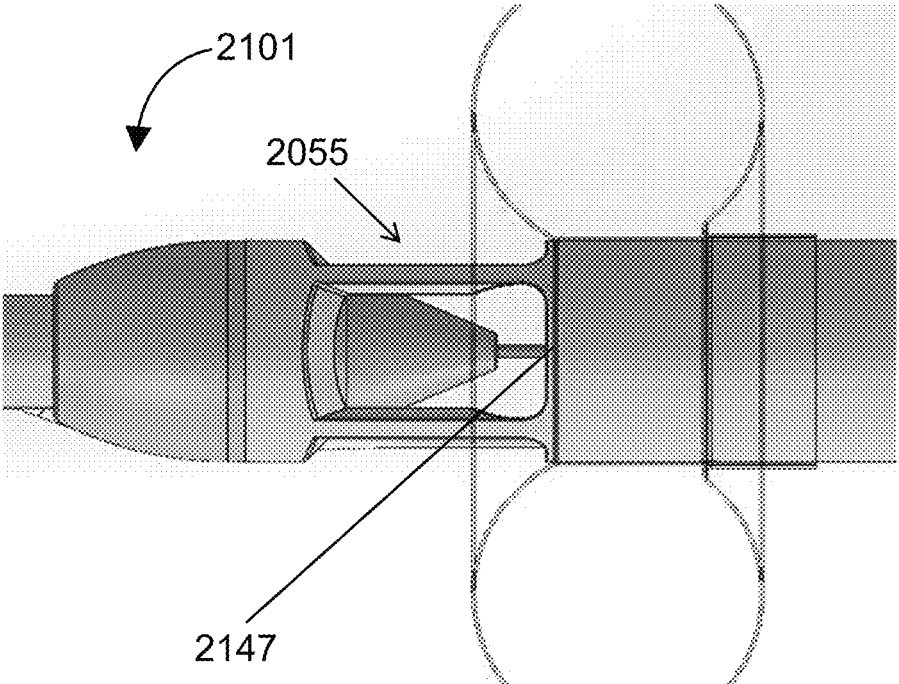
FIG. 21 shows a side view of an impeller assembly with rectangular proximal inlets.

FIG. 21 shows a side view of an impeller assembly 2101 with rectangular proximal inlets 2155. This configuration may reduce recirculation of blood at a proximal area of the impeller assembly 2101 by providing a larger inlet area at the distal-most region of the inlet 2147.

Figure 22:
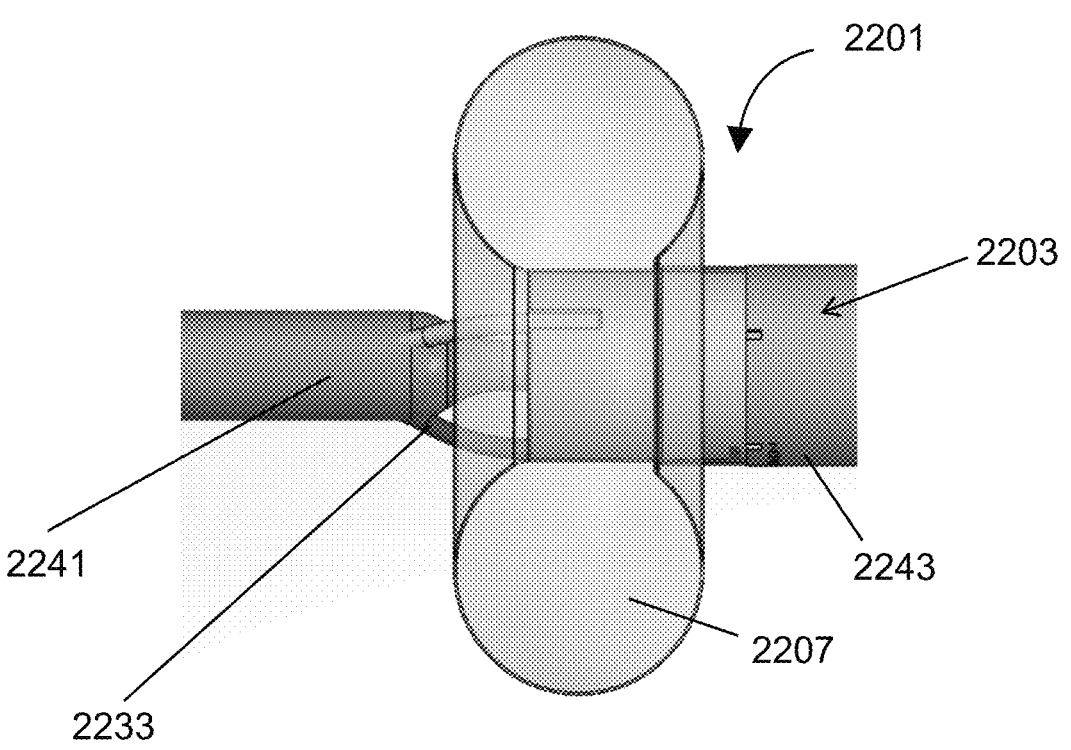
FIG. 22 shows an impeller assembly with arcuate proximal struts.

FIG. 22 shows an impeller assembly 2201 with arcuate proximal struts 2233. The arcuate proximal struts 2233 extend longitudinally and radially. In some embodiments, the arcuate proximal struts 2233 comprise tubular members. The tubular members may be welded to the impeller assembly 2201, connecting a proximal portion 2241 of the impeller housing 2203 to a distal portion 2243 of the impeller housing 2203. The arcuate proximal struts 2233 may connect to a proximal portion 2241 of the impeller housing 2203 integral with the catheter shaft. The arcuate proximal struts 2233 may comprise a monolithic structure. The monolithic structure may comprise a 3D printed structure.

The impeller assembly 2201 may be distally mounted to a catheter shaft (not shown) comprising a plurality of lumens and at least one of the lumens sealingly connected to an expandable member 2207 attached to an outer surface of the impeller housing 2203.

Figure 23:
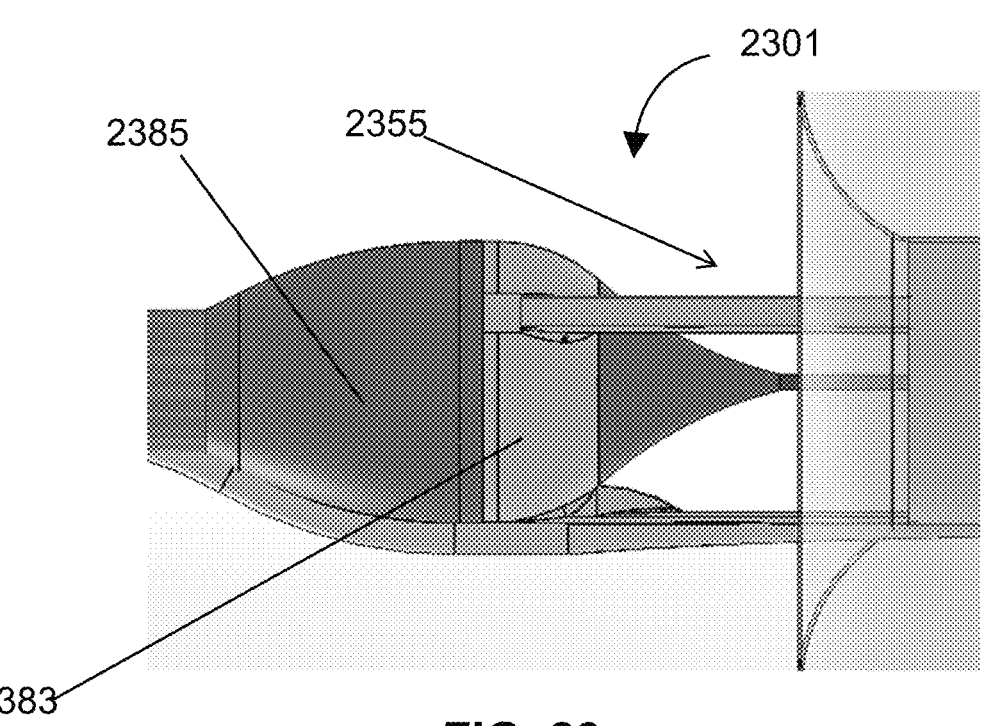
FIG. 23 shows a side view of a proximal portion of an impeller assembly.

FIG. 23 shows a side view of a proximal portion of an impeller assembly 2301. The proximal portion of the impeller assembly 2301 includes a proximal hub 2383, a proximal inlet 2355, and a body section 2385. The proximal hub 2383 may be configured to facilitate a smooth flow pattern as fluids, e.g., blood, are directed into the proximal inlet 2355. The hub 2383 may comprise a substantially circular outer geometry in axial cross section for easy movement within a vein. The hub 2383 may comprise a tapered geometry. For example, a cross-sectional diameter of the hub 2383 may decrease along a length of the hub 2383 from a first end to a second end. The hub 2383 may have a tapered outer geometry that may comprise a proximal diameter, an intermediate diameter, and a distal diameter wherein the intermediate diameter is greater than either the proximal diameter or the distal diameter and the transition between proximal, intermediate, and distal diameters is substantially smooth. The curve between the proximal, intermediate, and distal diameters may be without an inflection point.

Figure 24:
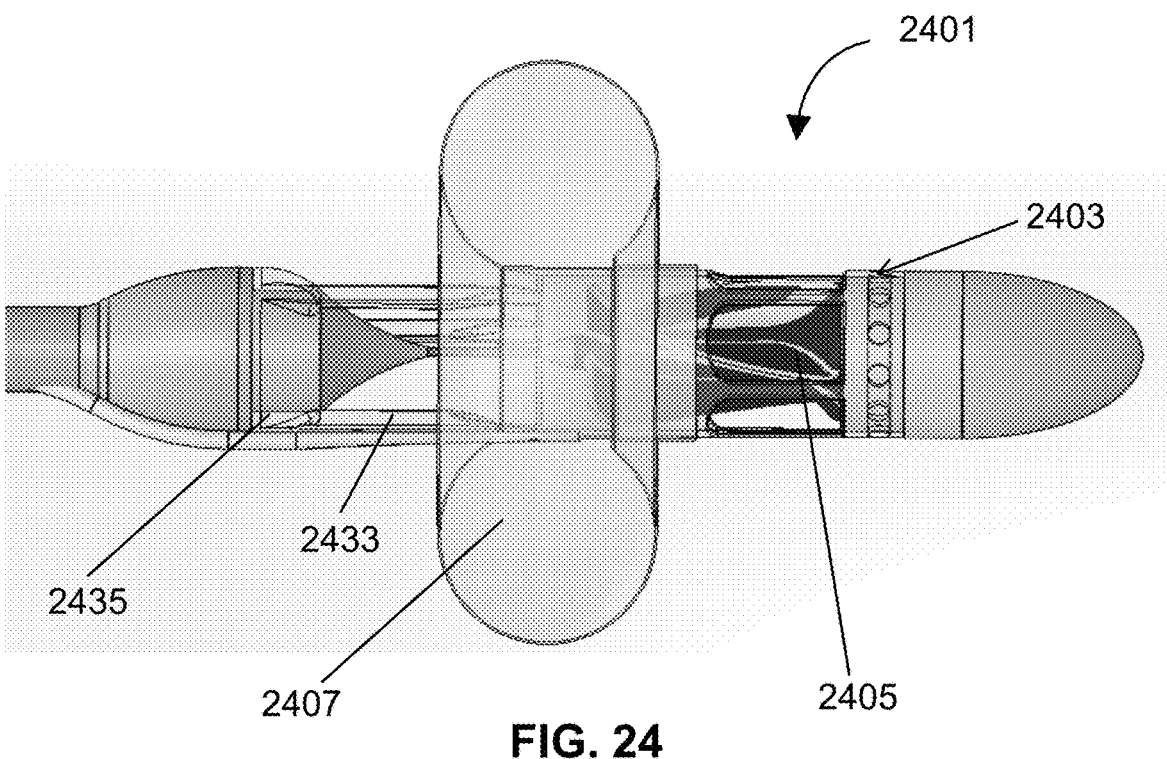
FIG. 24 illustrates an impeller assembly.

FIG. 24 shows an impeller assembly 2401. The impeller assembly 2401 includes an impeller housing 2403 with an impeller 2405 rotatably disposed therein. An expandable member 2407 depicted with ghosted lines is attached to an outer surface of the impeller housing 2403, the expandable member 2407 is shown in an expanded state.

The impeller assembly 2401 is designed to facilitate the flow of blood through the impeller housing 2403. The impeller assembly 2401 may include fillets 2435 under the proximal end of the proximal struts 2433 to provide mechanical support and prevent recirculation of blood in these regions when the catheter is inside a vein. In some embodiments, the proximal struts 2433 taper towards their distal ends.

Figure 25:
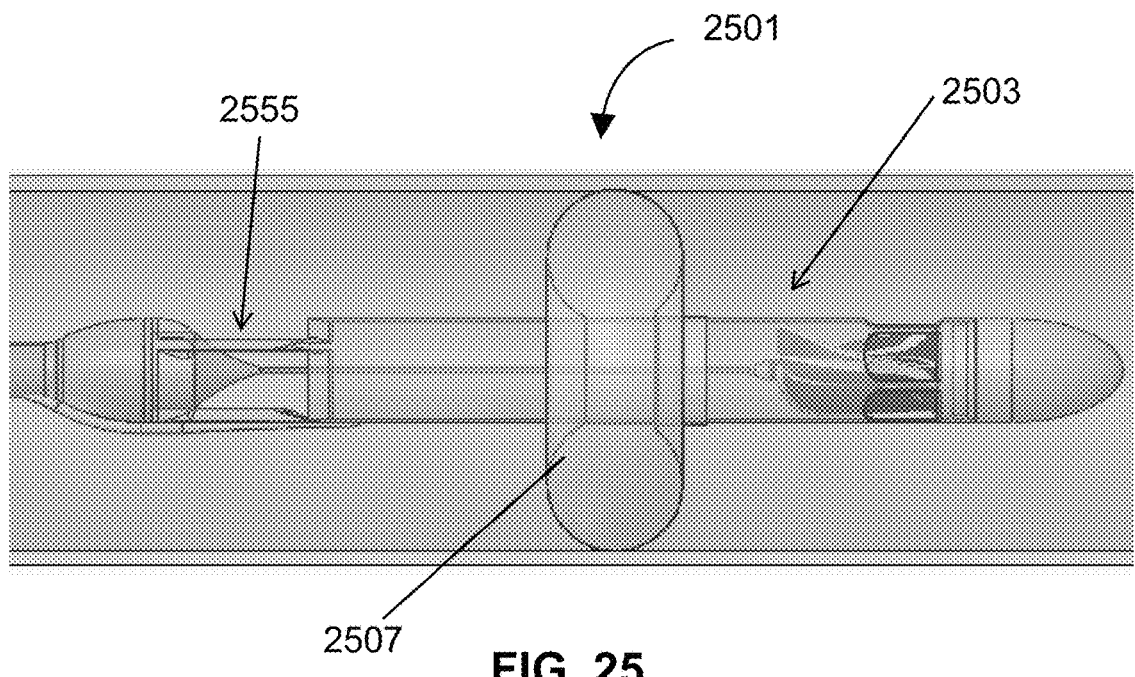
FIG. 25 shows an elongated impeller assembly.

FIG. 25 shows an elongated impeller assembly 2501. The elongated impeller assembly 2501 includes an expandable member 2507 spaced apart from a proximal inlet region 2555. The expandable member 2507 may be, for example, approximately 1-25 cm from the proximal inlet region 2555. Preferably, the expandable member is at least 1 cm from the proximal inlet region 2555.

Figure 26:
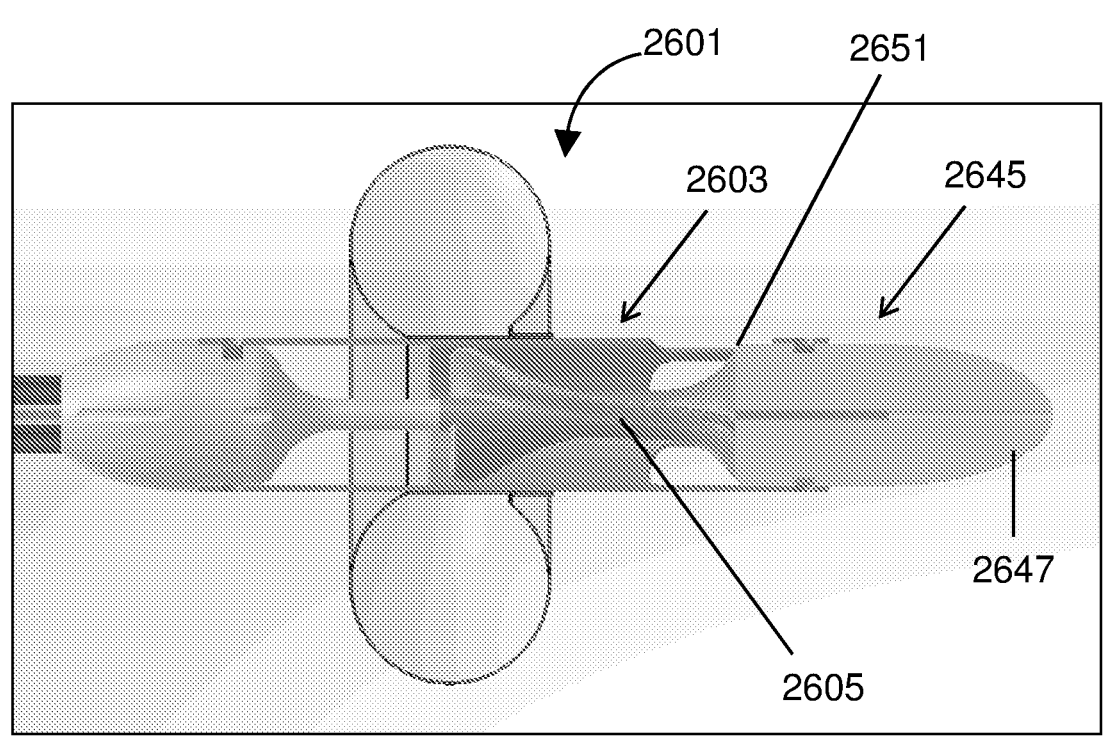
FIG. 26 shows a cross-sectional view of an impeller assembly.

FIG. 26 shows a cross-sectional view of an impeller assembly 2601. The impeller assembly 2601 includes an impeller housing 2603 with an impeller 2605 rotatably disposed therein. The impeller assembly 2601 includes a distal portion 2645. The distal portion 2645 may include a tip 2647 that is substantially disc shaped. The distal portion 2645 may have at least a partially flat surface. The disc-shaped tip 2647 may be spaced apart from a proximal surface of the distal portion 2645.

The impeller 2605 may comprises a substantially fixed axial position relative to the impeller housing 2603. The distal portion 2645 may comprise a substantially fixed axial position relative to the impeller housing 2603. The fixed axial positions of the impeller 2605 and the distal portion 2645 may define a distal gap 2651 between the distal portion 2645 and the impeller 2605. The gap 2651 is preferably greater than 5 um. The gap 2651 may be greater than 10 um or 20 um. The gap 2651 may be preferably less than 150 um, 120 um, or 100 um. Ideally, the gap 2651 is between 25 um and 50 um.

Figure 27:
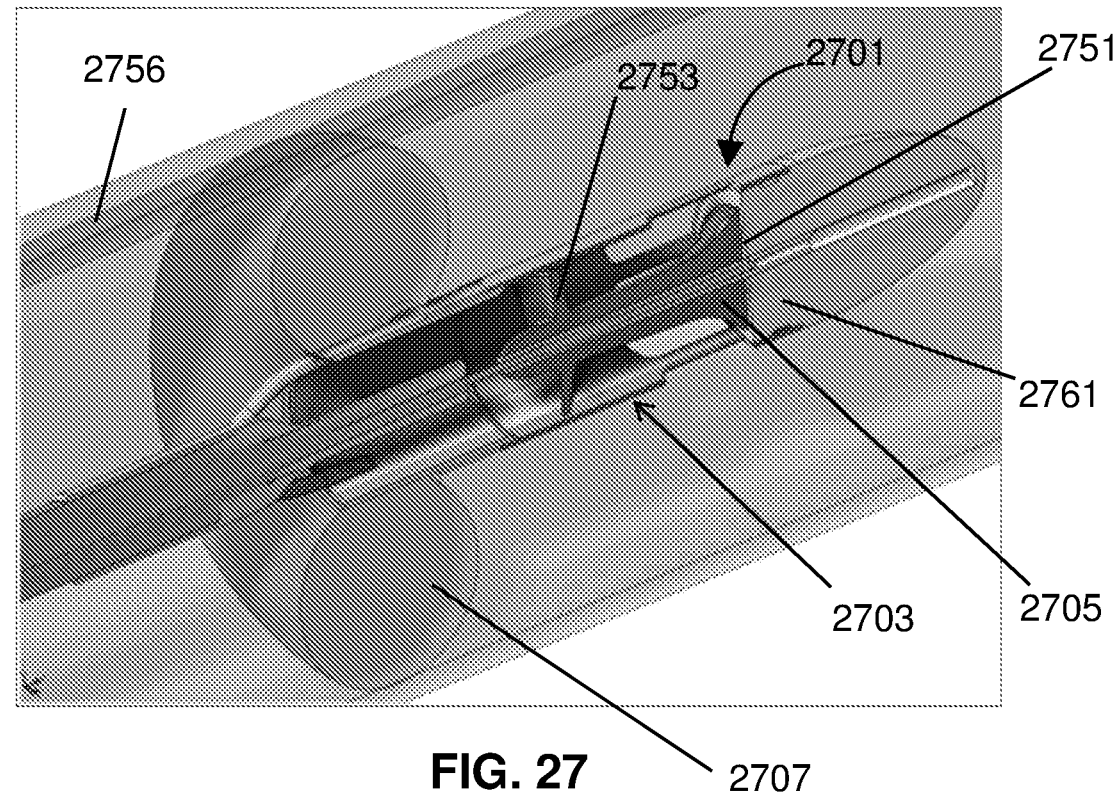
FIG. 27 is a cross-sectional view of an impeller assembly inside a vein.

FIG. 27 is a cross-sectional view of an impeller assembly 2601 inside a vein 2756. The impeller assembly 2701 comprises an impeller housing 2703 with an impeller 2705 inside. The impeller housing 2703 has an expandable member 2707 attached to an outer surface of the impeller housing 2703.

The impeller 2705 includes at least one blade 2753. The blade 2753 comprises a proximal end and a distal end. A core diameter of the impeller 2705 comprises a proximal end and a distal end. The core diameter proximal end is proximal of the proximal end of the blade 2753. The core diameter distal end and the blade distal end terminate substantially at the same axial region. The core diameter is smallest at the proximal end of the impeller 2705 and largest near the distal end of the core diameter. The core diameter may comprise a curved tapered surface.

The proximal end of the impeller 2705 core diameter may be spaced apart from the distal end of a cuff 2761. The proximal end of the impeller 2705 core diameter and the distal end of the cuff 2761 comprise a controlled proximal gap. The gap 2751 is preferably greater than 5 um. The gap 2751 may be greater than 10 um or 20 um. The gap 2751 may be preferably less than 150 um, 120 um, or 100 um. Ideally, the gap 2751 is between 25 um and 50 um.

The impeller 2705 may comprise an inner diameter, the inner diameter extending through at least a portion of the length of the impeller 2705 and being coaxial with the impeller 2705. The impeller 2705 may comprise a bearing arrangement distal of the distal surface. The bearing surface may include a ball bearing arrangement, for example, a ceramic bearing arrangement or a PTFE or PEEK bearing surface arrangement.

FIGS. 28A-F illustrates attachment and folding of an expandable member 2807. In particular, these drawings detail attachment of the expandable member 2807 to an outer surface of an impeller housing 2803 as wells as folding of the expandable member 2807 when the expandable member is inflated or when the catheter is being delivered or retrieved.

Figure 28A:
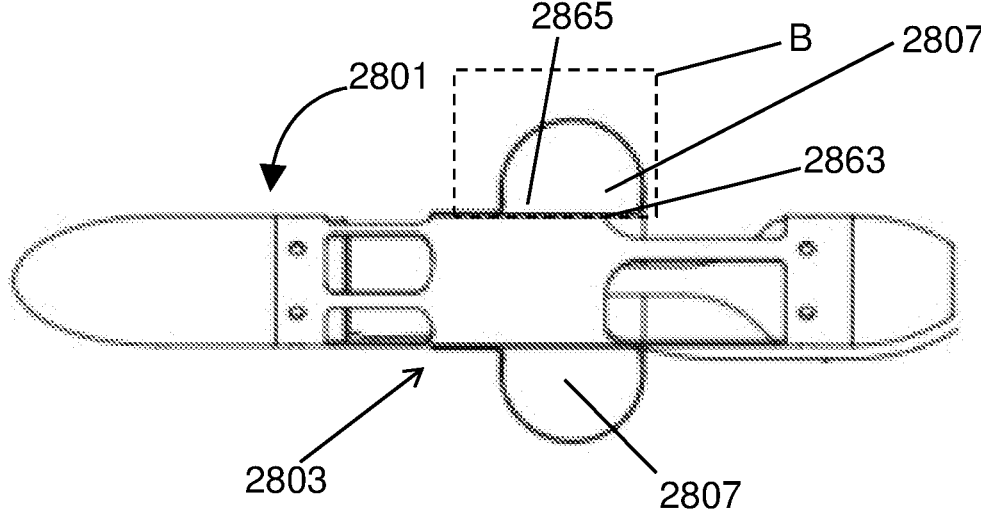
FIGS. 28A-F illustrates attachment and folding of an expandable member.

FIG. 28A is a partial cross-sectional view of an impeller assembly 2801. A portion of the cross-section demarcated by dashed lines and labeled B shows a portion of the expandable member 2807 and is enlarged in FIG. 28B. The expandable member 2807 includes at least one coupling 2863 attaching the expandable member 2807 with the impeller housing 2803. The coupling 2863 may create a sealed annular space in the expandable member 2807.

The coupling 2863 may comprise a laser weld joint, a solvent weld joint, an adhesive weld joint, a hot air or heated surface weld joint, or any other similar type of attachment. The coupling 2863 may comprise a prepared outer surface of the impeller housing 2803 onto which the expandable member 2807 is attached. For example, the impeller housing 2803 may be prepared such that the impeller housing 2803 includes at least one of a primed surface, a chemically activated surface, a plasma activated surface, a mechanically abraded surface, a laser ablated surface, an etched surface, or a textured surface. The prepared outer surface of the impeller housing 2803 may comprise a surface roughness, a patterned surface, or a high energy surface.

Figure 28B:
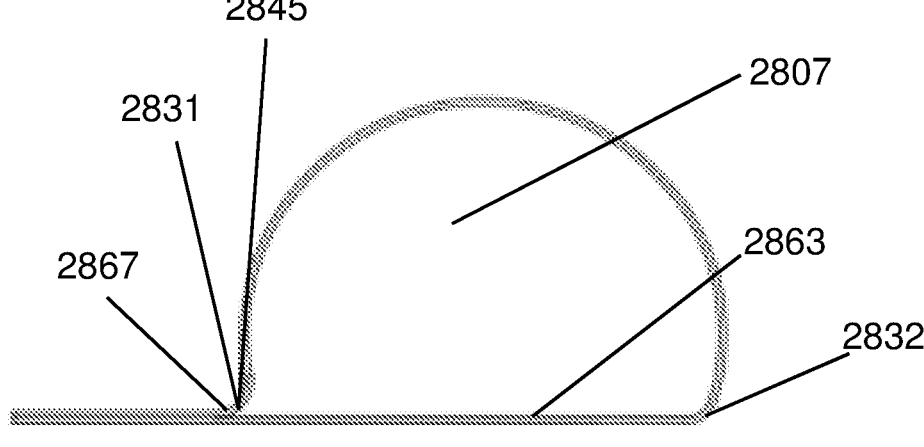

Referring to FIG. 28B, the expandable member 2807 may include at least one neck 2867, the neck 2867 may be dimensioned for joining with the impeller housing 2803. The expandable member 2807 may comprises a joint distal end 2831 and a joint proximal end 2832. The shape of the distal end 2831 may be configured to change as the expandable member is inflated/deflated (compare FIGS. 28B, 28D, and 28E) or when the catheter is moved inside a vein. In particular, the joint distal end 2831 may comprise a distal neck segment joined to the impeller housing 2803 and a distal transition segment 2845 that is integral with the neck 2867 but not attached to the impeller housing 2803. As the expandable member 2807 is inflated, the distal transition segment 2867 may fold inward. The joint proximal end may comprise a neck 2832 joined to the impeller housing 2803 and a proximal transition segment that is integral with the neck but not joined to the impeller housing. The expandable member 2807 may be configured to be substantially rigid in the expanded configuration. The expandable member 2807 may be configured to be conformable in the expanded configuration. The expandable member 2807 may be made from a polyurethane, or pebax or nylon material. The expandable member 2807 may be made from polytetrafluoroethylene.

Figure 28C:
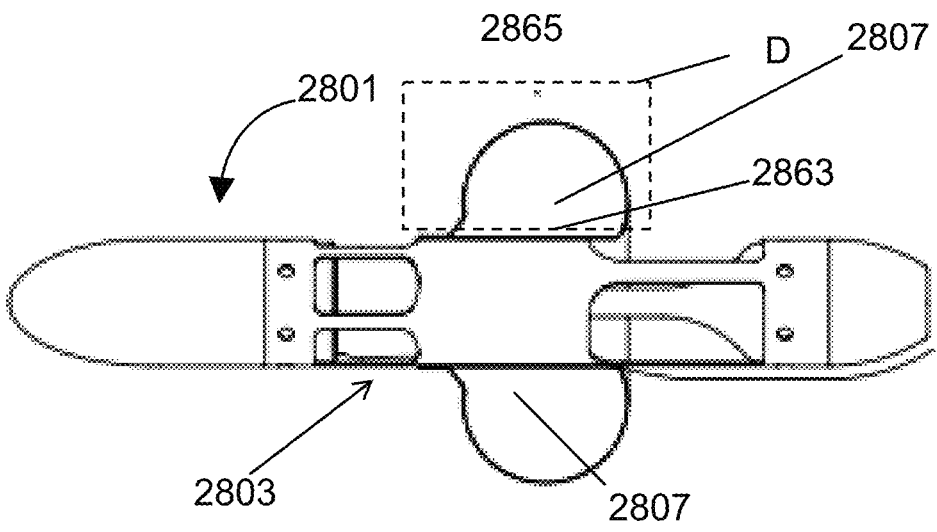
Figure 28D:
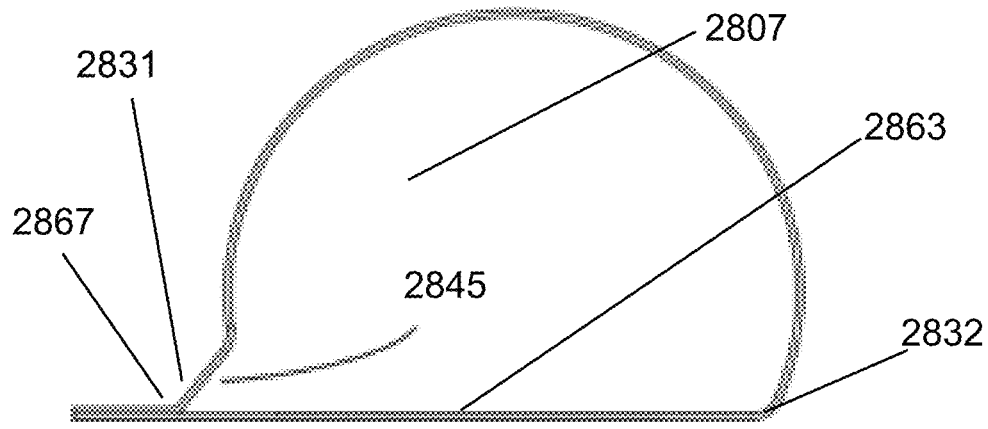

FIG. 28C is a partial cross-sectional view of the impeller assembly 2801 in which the expandable member 2807 is partially inflated. The portion of the partial cross-section showing the expandable member 2807 (labeled D) is enlarged in FIG. 28D. Notably, the shape of the distal neck changes as the expandable member 2807 is inflated (compare FIG. 28D in which the expandable member is partially inflated to FIG. 28B in which the expandable member is fully inflated).

Figure 28E:
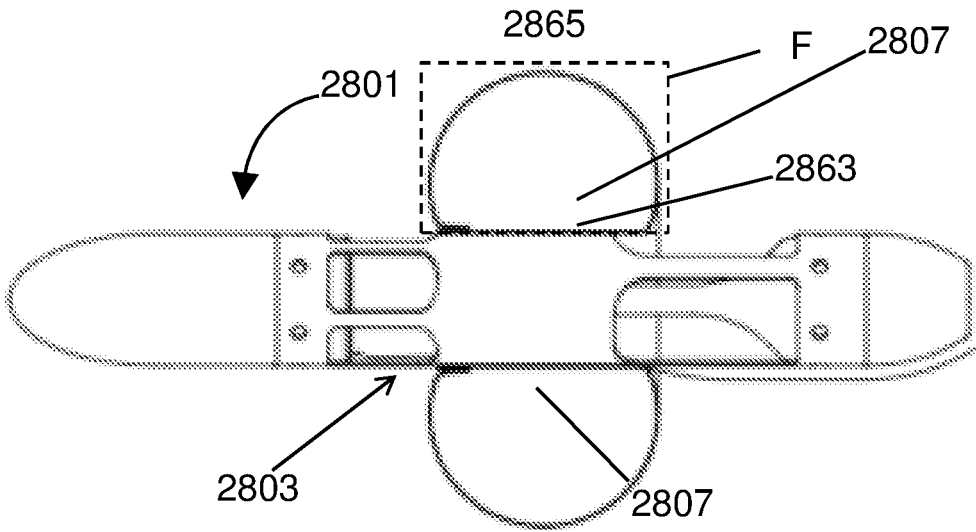
Figure 28F:
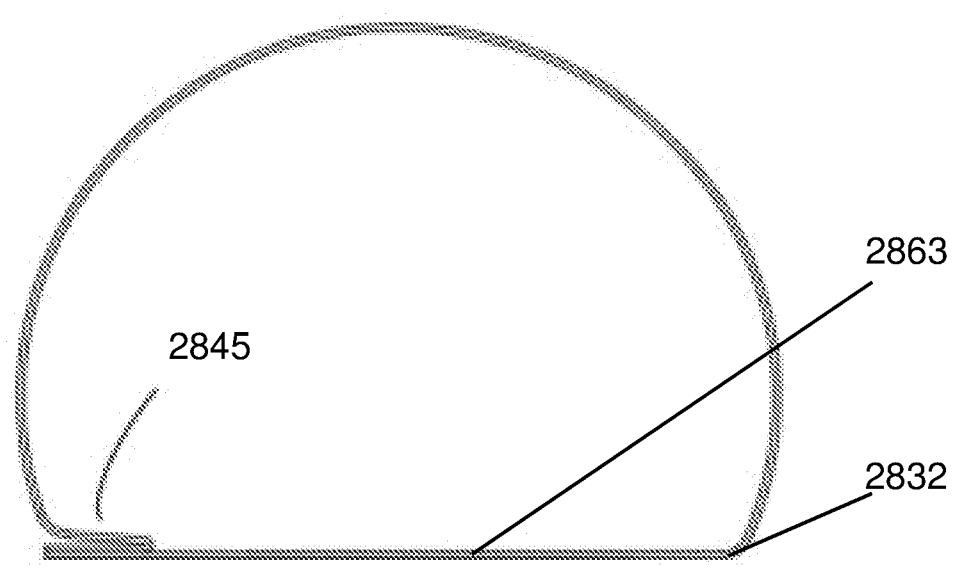

FIG. 28E is a partial cross-sectional view of the impeller assembly 2801 with moderately inflated expandable member 2807. The portion of the partial cross-section showing the expandable member 2807 (labeled F) is enlarged in FIG. 28F. In particular, the expandable member 2807 is inflated more than the expandable member 2807 illustrated in FIG. 28D. Upon inflating the expandable member 2807, the distal transition segment 2845 may fold outward eliminating a potential recirculation zone at the interface between the balloon and housing 2803.

FIG. 29 shows an impeller assembly 2901 with an expandable member 2907 having an elongated surface 2974 for interfacing with a wall of a blood vessel. The elongated surface 2974 increases an interaction between the blood vessel and the impeller assembly 2901 to restrict movement of the impeller assembly inside the blood vessel. The expandable member 2907 may comprise a compliant material. The compliant material may be a polyurethane or silicone. The compliant material may stretch 100% to 800%, thus creating an elongated surface 2974. In other embodiments, the expandable member 2907 may comprise a non-compliant material, which may expand to one specific size or size range, even as internal pressure increases.

FIG. 30 shows an impeller assembly 3001 with a two-part expandable member 3007. The two-part expandable member 3007 includes a first part 3065 comprising a compliant material and a second part 3066 comprising a non-compliant material. The first part 3065 and second part 3066 may be attached to each other and to the impeller housing 3003 to define an annular space for inflation. Preferably, the first part 3065 of the expandable member 3007 comprises a portion of the expandable member 3007 that interacts with a wall of a blood vein during operating of the catheter.

Figure 31:
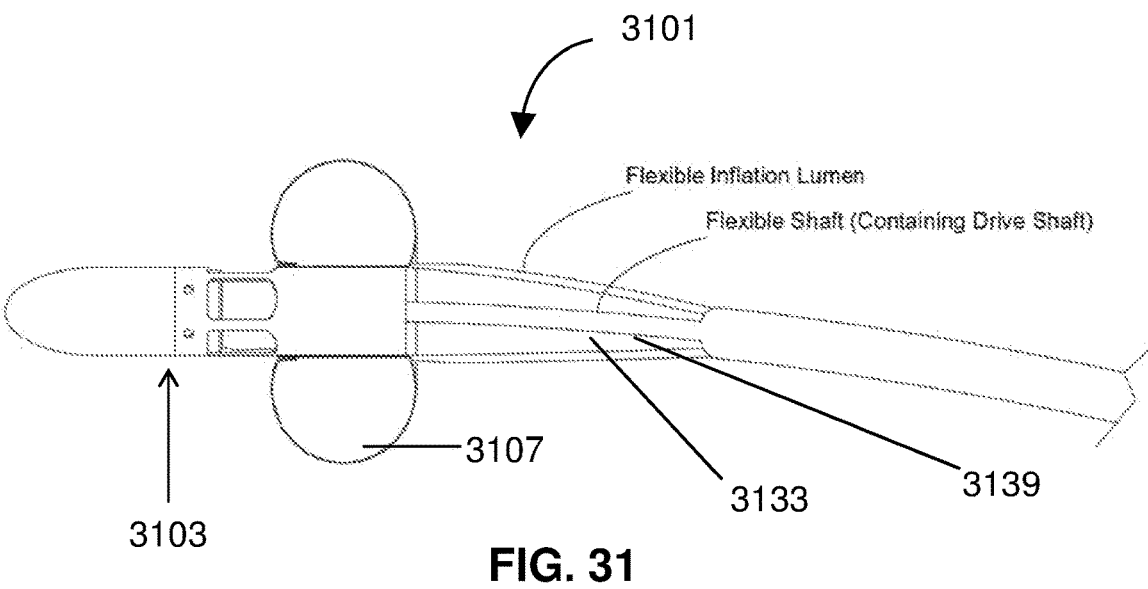
FIG. 31 is a partial cross-sectional view of a distal portion of a catheter.

FIG. 31 is a partial cross-sectional view of a distal portion of a catheter 3101. The distal portion of the catheter 3101 is attached to an impeller housing 3103 with an expandable member 3107 mounted to an outer surface of the impeller housing 3103. The impeller housing 3103 is connected to a distal portion of a catheter 3101 by a plurality of proximal struts 3133. The proximal struts 3133 preferably comprise a flexible material, for example, latex, silicone, or Teflon, to provide for easier navigation inside a vein of a patient. The proximal struts 3133 may be configured to conform to anatomical curvatures. A drive shaft 3139 connecting a motor to an impeller disposed inside the impeller housing 3103 may comprise a flexible drive cable.

Figure 32:
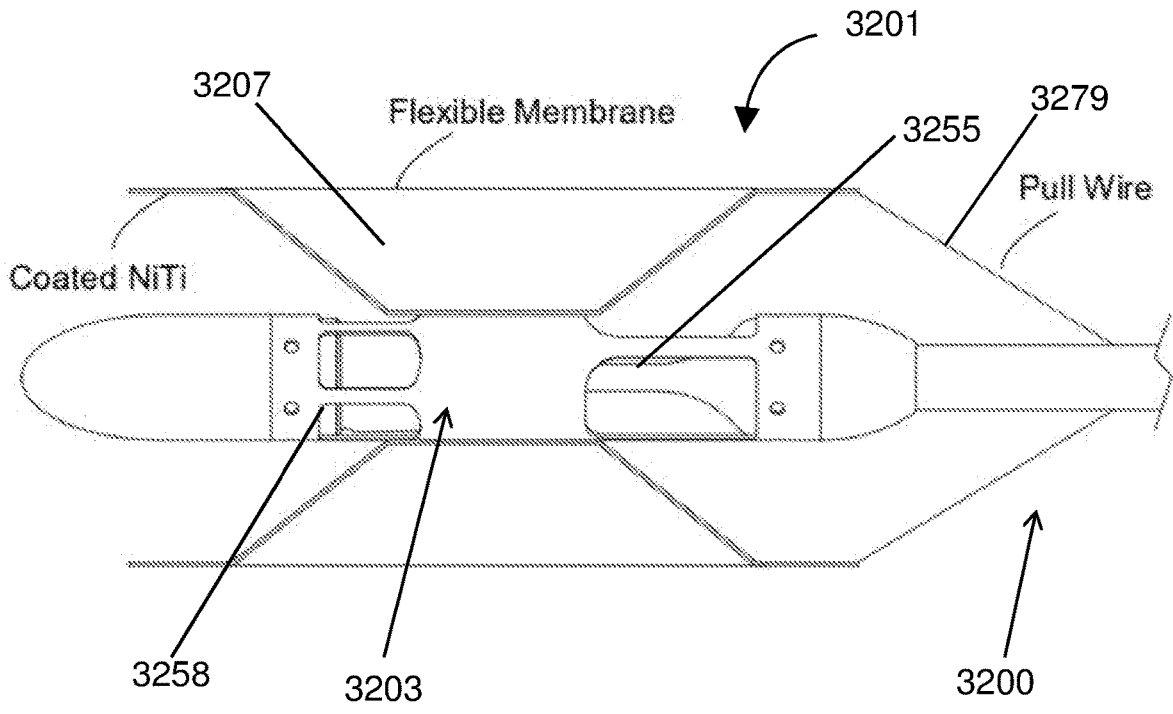
FIG. 32 is a partial cross-section of a self-expanding impeller assembly.

FIG. 32 is a partial cross-section of a self-expanding impeller assembly 3201. The impeller assembly 3201 comprises an impeller housing 3203 with an impeller 3205 disposed therein. An expandable body 3207 is attached to a surface of the impeller housing 3203 between proximal inlets 3255 and distal outlets 3258.

In an expanded configuration, the expandable body 3207 is configured to oppose a wall of a vein over a longitudinal segment of the vein. The longitudinal segment of apposition extends proximal of the proximal inlets 3255. The longitudinal segment of apposition extends distal of the distal inlets 3258. The expandable body 3207 is configured to provide a proximal flow directing funnel that extends from a region of apposition with the vessel wall to the distal end of the inlets 3255. The proximal flow directing funnel is configured to promote converging flow pattern at the entrance to the proximal inlets 3255. The expandable body 3207 may be configured to provide a distal flow directing funnel that extends from a proximal region of the outlets 3258 to a region of apposition with the vessel wall to the distal end of the outlets 3258. The distal flow directing funnel may be configured to promote diverging flow pattern distal of the exit of the outlets 3258. The diverging flow pattern may be configured so as to impart a gradual deceleration of fluid distal of the outlets and maintain a larger proportion of the pressure gain developed by the impeller 3205 by reducing recirculating or negative velocity flow patterns.

The expandable body 3207 may comprise a nitinol membrane, a non-compliant membrane, or a porous membrane. The longitudinal segment of the expandable body 3207 may comprise a compliant material. Preferably, the flow directing funnels of the expandable body 3207 comprise a relatively less compliant material (or a semi compliant material or a non-compliant material).

The catheter 3200 may comprise a plurality of pull wires 3279 attached to the expandable body 3207 and configured to facilitate collapse of the expandable body 3207 in preparation for the removal of the catheter 3200 from the body.

Figures 33, 34:
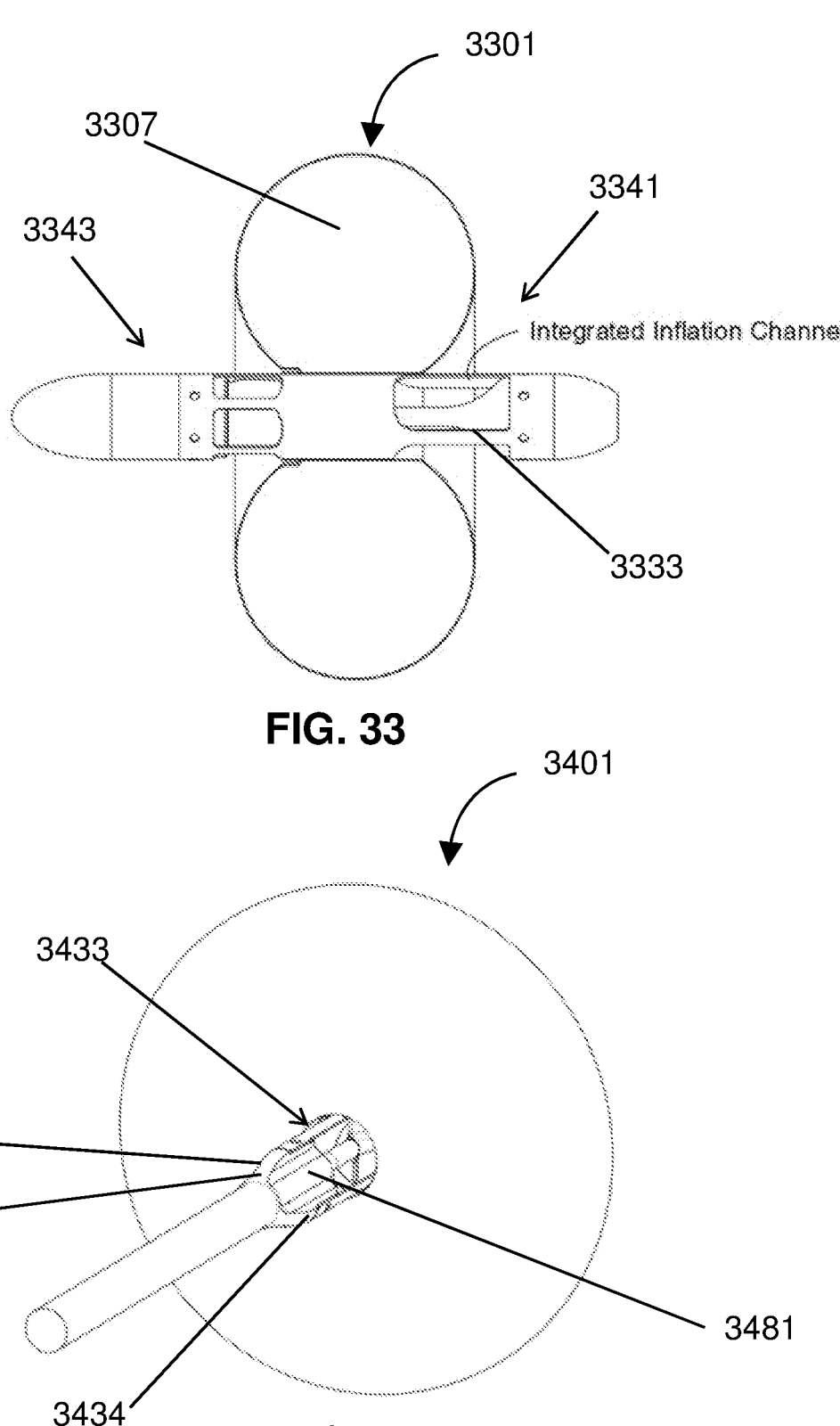
FIG. 33 shows a partial cross-section of an impeller assembly.
FIG. 34 shows an inlet of an impeller assembly.

FIG. 33 shows a partial cross-section of an impeller assembly 3301. The impeller assembly 3301 comprises proximal struts 3333 attaching a proximal portion 3341 of the impeller assembly 3301 to a distal portion 3343 of the impeller assembly 3301. At least one proximal strut 3333 comprises an inflation lumen, i.e., an integrated inflation channel, extending through the proximal strut 3333 to an interior of an expandable member 3307 that is attached to an outer surface of the impeller assembly 3301. The inflation lumen provides a structure for inflating the expandable member 3307. The inflation lumen is preferably terminated within the inlet to minimize disruption to the flow inside the housing. This is facilitated by the more proximally positioned expandable member 3307.

FIG. 34 shows an inlet 3433 of an impeller assembly 3401. The inlet 3433 is configured to provide easier fluid flow into the assembly 3401. This configuration includes a proximal hub 3480 with at least one flow basin 3481. The flow basin 3481 extends from a proximal region of the proximal hub 3480 and terminates at the inlet 3433. The flow basin 3481 extends between a first and second strut 3433, 3434. The flow basin 3481 may be configured to modulate a flow of blood upstream of the inlets. For example, the flow basin 3481 may progressively slope inwards along the length of the flow basin 3481 towards the inlet 3433.

Figure 35:
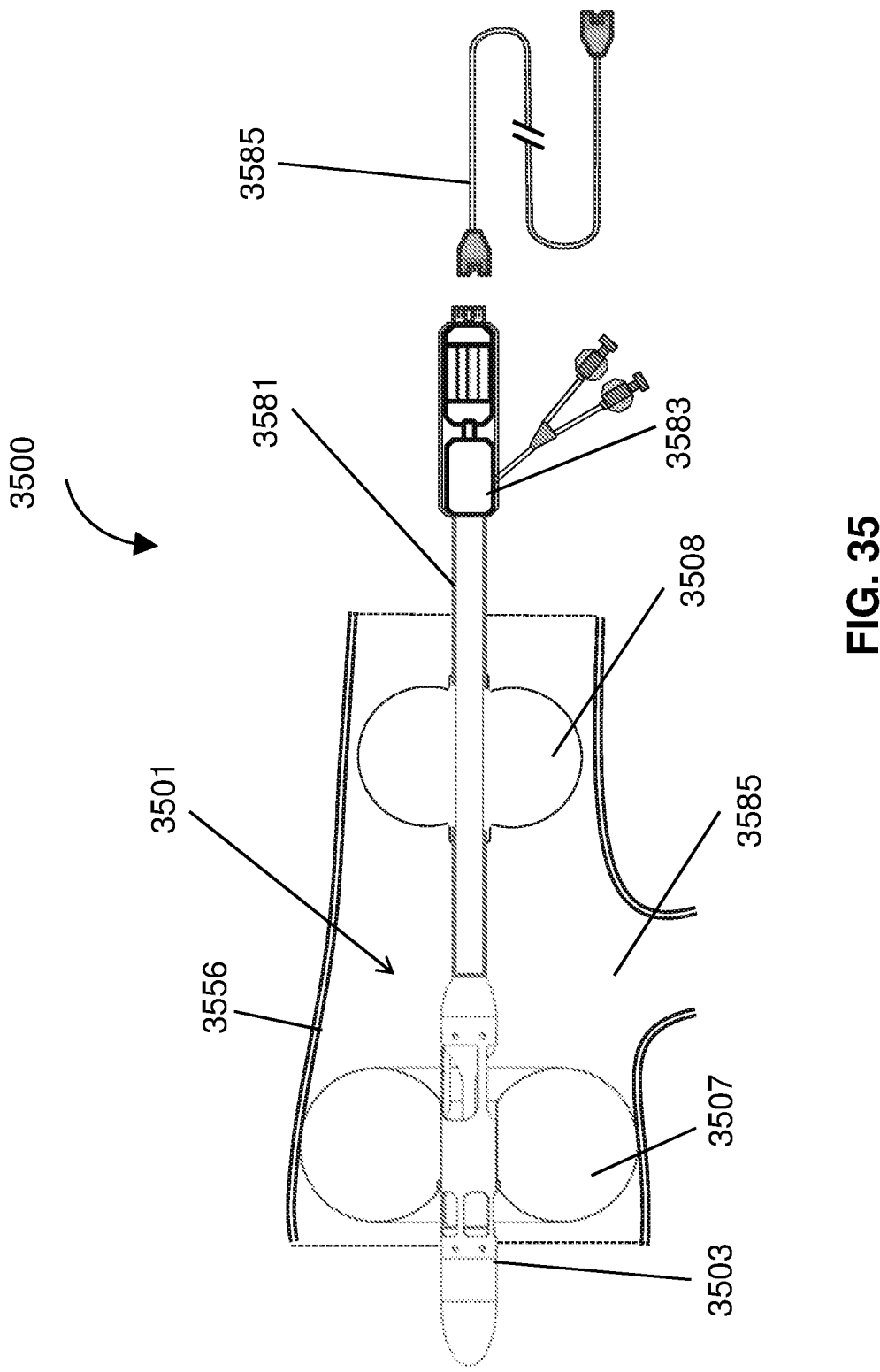
FIG. 35 is an exemplary catheter system.

FIG. 35 is an exemplary catheter system 3500. In particular, FIG. 35 illustrates a catheter 3500 according to aspects of the invention to show interactions between an impeller assembly 3501 of the catheter 3500 and a blood vessel wall 3556. The catheter 3500 includes the impeller assembly 3501, a catheter shaft 3581, a proximal expandable member 3508, a hub 3583 and a motor (not shown).

The impeller assembly 3501 is dimensioned for placement inside a blood vessel with a shaft 3581 extending from the impeller assembly 3501 to a position exterior of the patient. The shaft 3581 may comprise a multilumen shaft. A first proximal expandable member 3508 is attached to the shaft 3581 and may be configured to restrict a flow of blood to the impeller assembly 3501.

A motor may be connected to an impeller housed within the impeller assembly 3501 and may be configured to drive the impeller at high RPMs. The impeller assembly 3501 may comprise a distal expandable member 3507 mounted onto an outer surface of an impeller housing 3503 and wrapping around the impeller housing 3503, for example, like an expandable ring. The distal expandable member 3503 may be configured to appose a vessel wall 3556 during operation of the catheter.

The proximal expandable member 3508 may be mounted on the catheter shaft 3581 proximal of the impeller assembly 3501. The proximal expandable member 3508 may be spaced apart from the impeller assembly 3501. For example, the proximal expandable member 3508 may be a distance of 1-10 cm upstream of the impeller assembly 3501, preferably about no more than about 5 cm.

The proximal expandable member 3508 may be dimensioned for placement (inflation) between the vessel access site and an outflow port of a thoracic duct 3585. The expandable members 3507, 3508 are preferably configured to atraumatically contact a vessel wall.

In some embodiments, a proximal expandable member 3508 may be configured to reduce a volume of blood flowing in the vessel by impeding a flow of flood. The proximal expandable member 3508 may be configured to adjust the volume of blood flowing in the vessel by impeding, restricting, guiding, or directing the flow of blood. For example, the proximal expandable member 3508 may include an orifice for fluid to flow across the expandable member 3508 while the expandable member 3508 is in an expanded state. For example, the orifice may substantially comprise one of an annular ring or a crescent shape with a lumen through a body of the expandable member 3508. The orifice may comprise a valley or a recess in the outer surface of the expandable member 3508. The orifice may comprise a channel underneath the expandable member 3508. The expandable member 3508 may comprise a shape that defines the orifice. For example, the expandable member 3508 may be shaped at least partially as a spherical, conical, or cylindrical shape and the orifice comprises an annular ring or a crescent. The expandable member 3508 shape may comprise, for example, a double D shape and the orifice may be defined by surfaces between the two joining shapes. The expandable member 3508 may comprise a helical shape wrapped around the catheter shaft 3581 and the orifice may comprise a channel defined by a space between adjacent spirals.

The proximal expandable member 3581 may comprises a compliant material and the compliant material may comprise a compliance-pressure relationship. The expandable member 3581 may be processed so the compliance pressure relationship is repeatable. The expandable member 3581 may comprise an annealed member. The expandable member 3581 may be configured to achieve a precise diameter at a given pressure. The expandable member 3581 may be configured to have minimal hysteresis when inflated, deflated and inflated again.

The hub 3583 may be configured to facilitate inflation of a distal expandable member 3507, and may be configured to at least partially inflate the proximal expandable member 3508. For example, the hub 3583 may include access to one or more lumens that extend through the catheter shaft 3581 and connect to a proximal and/or distal expandable member 3508, 3507. The expandable members can be inflated by infusing a fluid into the lumens at the hub 3583. The hub 3583 may be configured to inflate the proximal expandable member 3508 into apposition with an innominate vessel.

The device may comprise a connector cable 3585 configured to connect the catheter to a console (not shown), the console may comprise a computer with hardware, software and a user interface. The console can be configured to operate the device.

Figure 36:
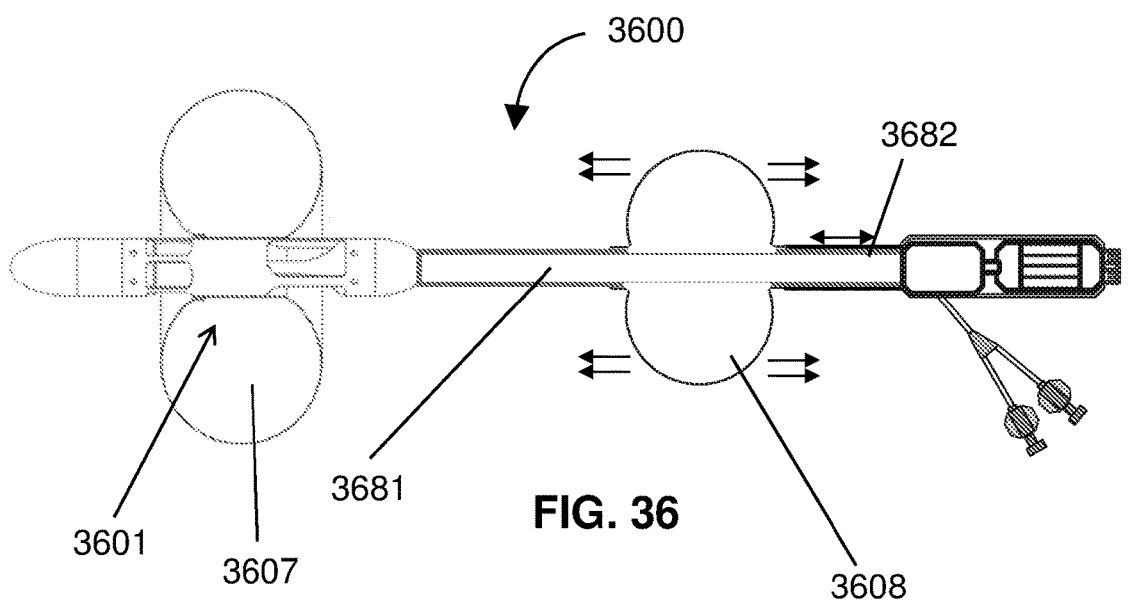
FIG. 36 shows a catheter with an expandable member slidably mounted along a shaft of the catheter.

FIG. 36 shows a catheter 3600 with an expandable member 3608 slidably mounted along a shaft 3681 of the catheter 3600. The catheter 3600 comprises a first catheter shaft 3681 and a second catheter shaft 3682. The catheter 3600 includes an impeller assembly 3601 attached to a distal end of the first catheter shaft 3681. The proximal expandable member 3608 mounted near a distal end of said second catheter shaft 3682.

The first catheter shaft 3681 may comprise a multilumen tubing wherein a first lumen is configured to facilitate inflation of a distal expandable member 3607 and a second lumen is configured to transmit mechanical or electrical energy to facilitate the operation and control of an impeller disposed within the impeller assembly 3601.

The second catheter shaft 3682 may comprise a multilumen tubing wherein a first lumen is configured to encapsulate the first catheter shaft 3681 and a second lumen is configured to inflate the proximal expandable member 3608. The first and second catheter shafts 3681, 3682 may be configured to facilitate relative axial movement (indicated by arrows) between the distal expandable member 3607 and the proximal expandable member 3608. The relative axial movement may be limited distally. The relative axial movement may be is limited proximally. The catheter 3600 may include a first stop and a second stop and axial movement of second shaft 3682 may be limited by the first and second stops. The first and second stops may be mounted on the first shaft 3681, exterior of the patient (inside or around the hub). The axial movement may comprise fine movements. The fine movements may comprise, for example, a thread or ratchet mechanism.

Relative axial movement between the distal expandable member 3607 and the proximal expandable member 3608 may provide better anatomical placement, i.e., accurate placement of the distal expandable member 3607 in the innominate vein and then accurate placement of the proximal expandable member 3608 between the vessel wall access site and the thoracic duct.

The first and second shafts 3681, 3682 may extend exterior of the patient. The second shaft 3682 may be coupled and decoupled to the first shaft during use. In a collapsed state, the catheter may be dimensioned for advancement through a valve and lumen of a sheath. The second shaft 3682 may comprise a distal segment and a proximal segment. The distal segment may comprise a tubular member and an inflation lumen with the proximal expandable member sealingly welded (bonded) to a distal segment so as to create an inflation space in the expandable member 3607 that is in fluid communication with the inflation lumen.

The proximal segment of the second shaft may comprise an inflation lumen and a member configured to transmit axial push and pull forces to the distal segment of the second shaft 3682. The proximal segment of the second shaft may be concentric or eccentric with the first shaft. The inflation lumen of the proximal segment may be integral with a wall of the proximal segment of the second shaft.

Figure 37:
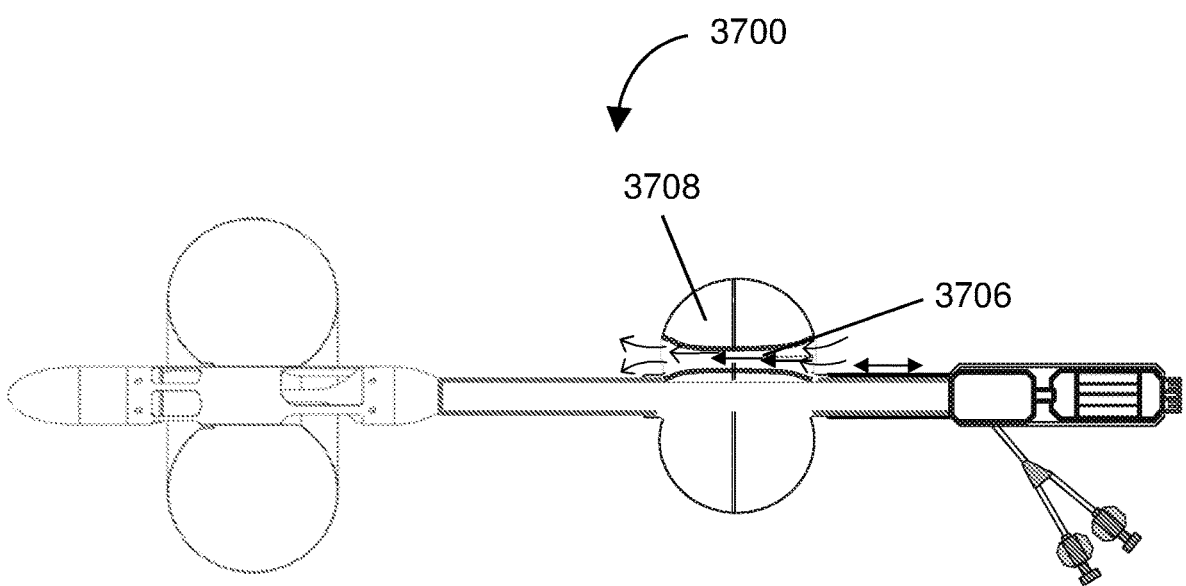
FIG. 37 shows a fluid channel across an expandable member that allows a controlled amount of blood flow.

FIG. 37 shows a fluid channel across an expandable member 3708 that allows a controlled amount of blood flow. The proximal expandable member 3708 may be configured to oppose a wall of a vessel. The proximal expandable member 3708 may comprise a flow channel 3706, the flow channel 3706 defining a lumen through the body of the expandable member 3708. Flow is indicated by black arrows. The flow channel 3706 may comprise a collapsed state and an expanded configuration. The flow channel 3706 may be configured to expand when the expandable member 3708 is inflated. The expandable member 3708 may comprise at least one inner membrane, the inner membrane may be configured to support the body flow channel 3706 in the expanded state. The proximal expandable member 3708 may be configured to allow 100 ml or more fluid to cross the expandable member 3708 per minute.

Figure 38:
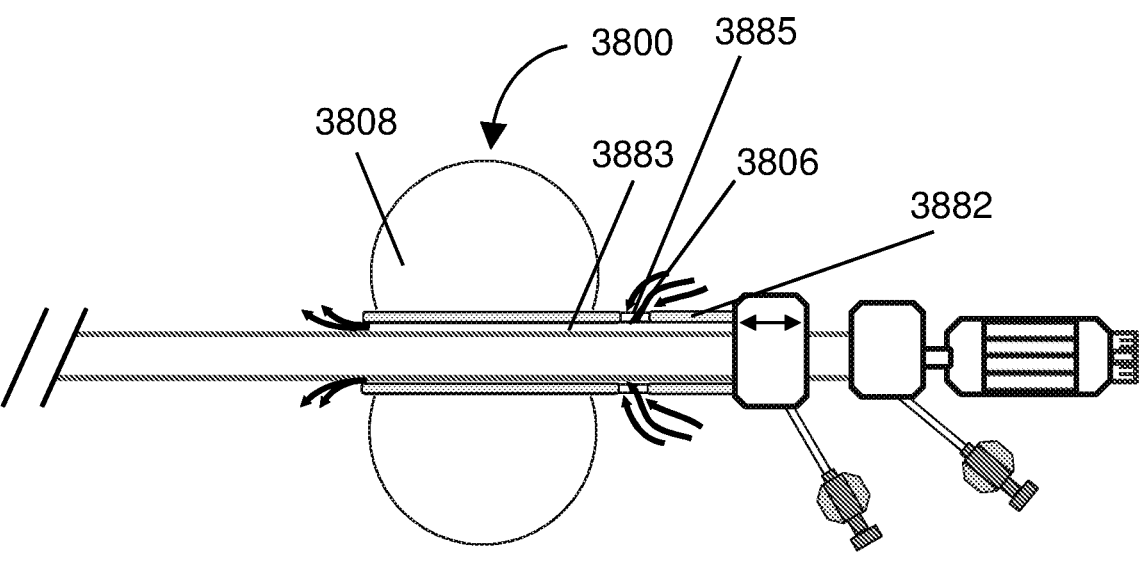
FIG. 38 shows a catheter with an alternative bypass channel.

FIG. 38 shows a catheter 3800 with an alternative bypass channel 3806. A second shaft 3882 comprises a tubular member with a distal end and a proximal end and a lumen 3883 extending through both distal and proximal ends. The lumen 3883 may be sized to provide a fluid flow pathway underneath the inflated expandable member 3808 in a distal segment. The second shaft 3882 may comprise an entry port 3885 at the proximal end of the distal segment of the second shaft 3882, the entry port may be configured to facilitate blood flow into said fluid flow pathway.

Figure 39:
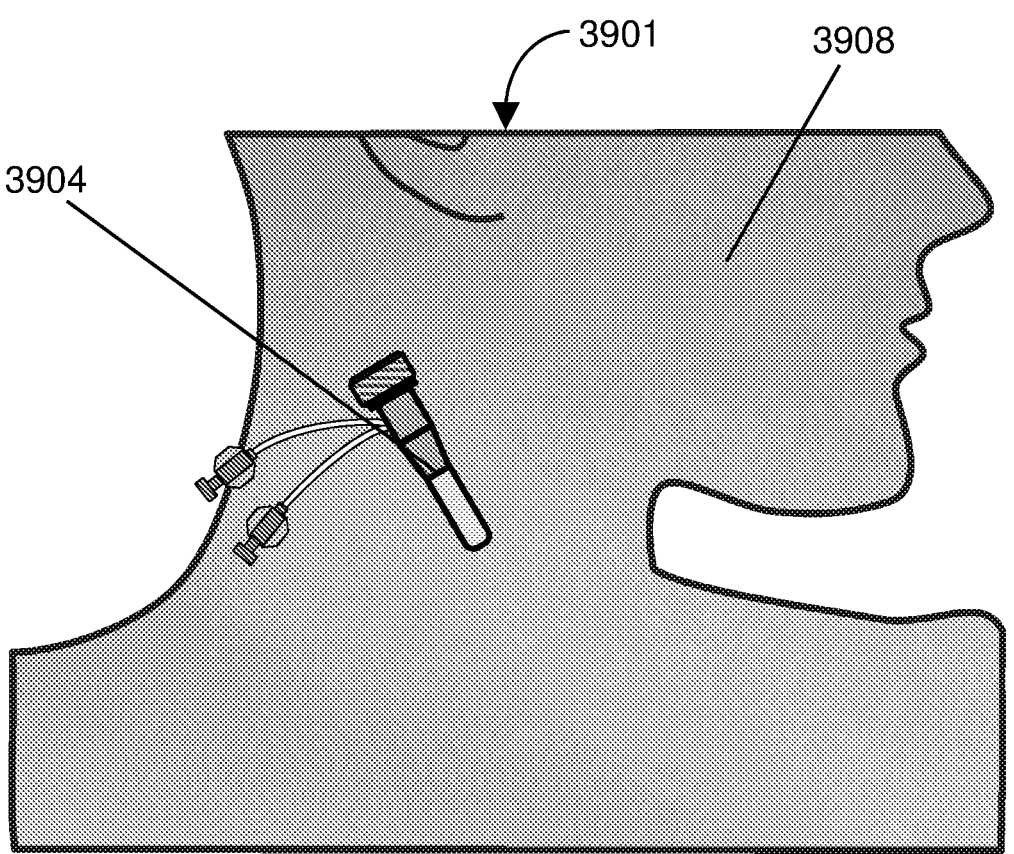
FIG. 39 shows a patient interface with a sheath in situation.

FIG. 39 shows a patient interface 3900 with a sheath 3904 in situation. A proximal expandable member, a flow entry port, and pressure sensor, may be on the sheath. The catheter system may comprise a catheter and a flow control sheath 3904, the catheter comprising an impeller assembly at a distal end of an elongated shaft, the flow control sheath 3904 comprising a flow restrictor, a fluid channel and a pressure sensor.

The system may be configured for transdermal insertion into a vein of a patient 3908. Insertion of the catheter comprises transdermal insertion in a region of the neck. The flow control sheath 3904 may be configured for placement so as to provide an access platform for other components of the system. The flow control sheath 3904 may comprise a flow restrictor adjacent a tip. The flow restrictor may comprise an expanded state and a collapsed state. In the collapsed state the flow restrictor may be configured to collapse completely onto the shaft of the sheath. In the collapsed state, the OD of the flow restrictor may be substantially the same as the shaft of the sheath. The restrictor may sit in an annular recess in a diameter of the shaft of the flow control sheath in the collapsed configuration. In the expanded configuration, the flow restrictor may be configured to at least partially restrict fluid flow through the jugular vein. The flow restrictor may be configured to control the rate of flow through the jugular vein. The flow restrictor may be configured to prevent inadvertent displacement of the flow control sheath during the procedure.

The flow control sheath may comprise a pressure sensor, the pressure sensor may be configured to measure pressure in a vein upstream of the restrictor. The sheath may comprise a lumen in a wall of the sheath and the pressure sensor may be positioned in said lumen. The pressure sensing lumen may comprise a port, the port may be configured to establish a hydrostatic connection between blood in the vein and the pressure sensor. The pressure sensor and the pressure sensing lumen may be sized to prevent blood flow ingress into the pressure sensing lumen.

Figure 40:
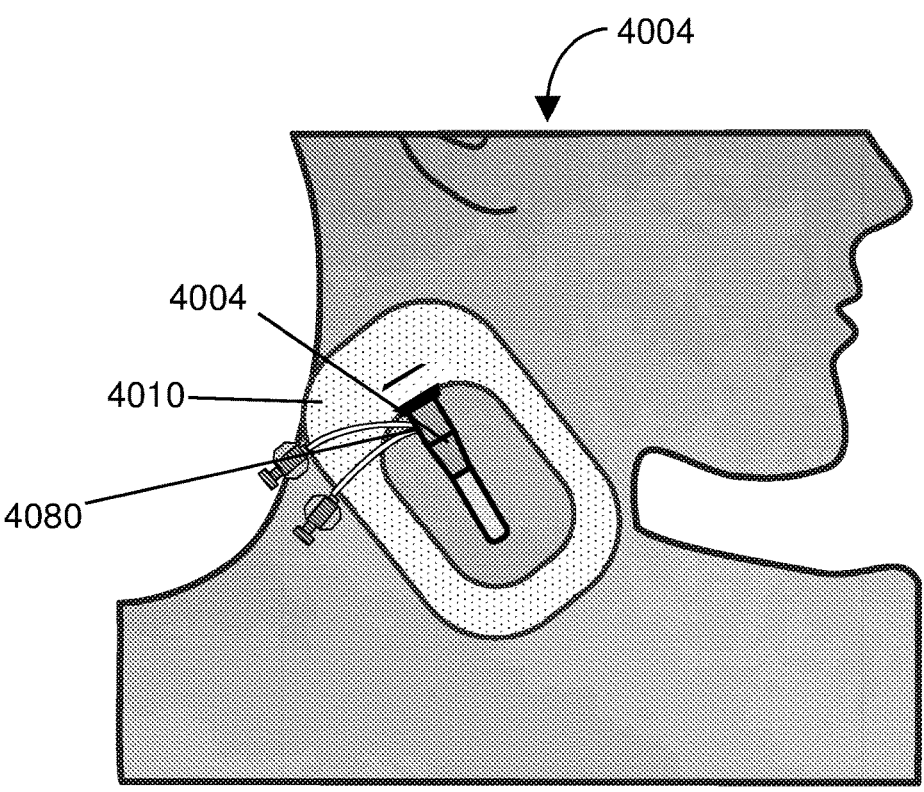
FIG. 40 shows a patient interface with a sheath held in situation by an adhering membrane.

FIG. 40 shows a patient interface 4000 with a sheath 4004 held in situation by an adhering membrane 4010. The adhering member 4010 helps maintain a sterile region around an access site and secures a hub 4080 of the sheath 4004 to the skin. This reduces irritation to the patient by movement of the hub 4080 made by accidental forces. The membrane 4010 may be shaped so as to allow second or tertiary layers to be added to tie all of the various system elements of the sheath 4004 or catheter together or to the skin.

Figure 41:
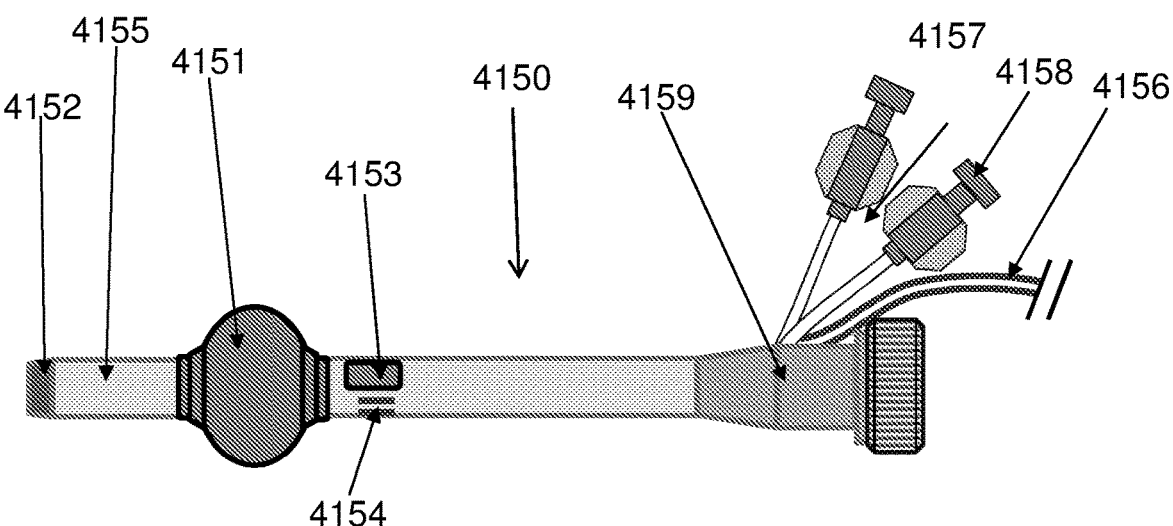
FIG. 41 shows a flow control sheath.

FIG. 41 shows a flow control sheath 4150. Shown are various features of the flow control sheath 4150 according to some preferred embodiments. In particular, the flow control sheath 4150 may include a restrictor 4151 (shown in an inflated state), a sheath tip 4152, a port 4153, a pressure sensor 4154, a sheath shaft 4155, and a hub 4159, the hub 4159 including a pressure sensor lead 4156, an inflation side port 4157, a flushing and infusion side port 4158. At least one suturing hole may be added to the hub 4159 to facilitate fixation to the patient.

Figure 42:
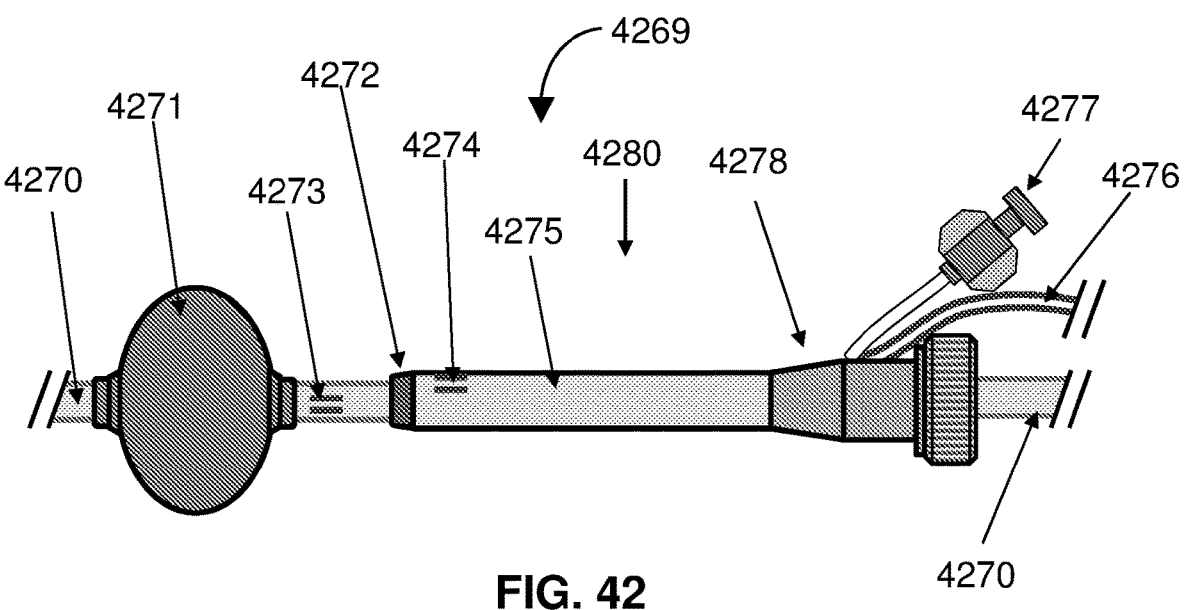
FIG. 42 shows a proximal portion of a catheter system.

FIG. 42 shows a proximal portion of a catheter system 4200. A catheter 4269 that is similar to the catheter described in FIG. 40 is disposed within a catheter sheath 4280. The catheter 4269 includes a shaft 4270, a proximal expandable member 4271 (depicted in an expanded state), and a catheter pressure sensor 4273. The sheath 4280 includes a sheath tip 4272, a sheath pressure sensor 4274, a sheath shaft 4275, a pressure sensor lead 4276, an inflation side port 4277, and hub 4278.

Figure 43:
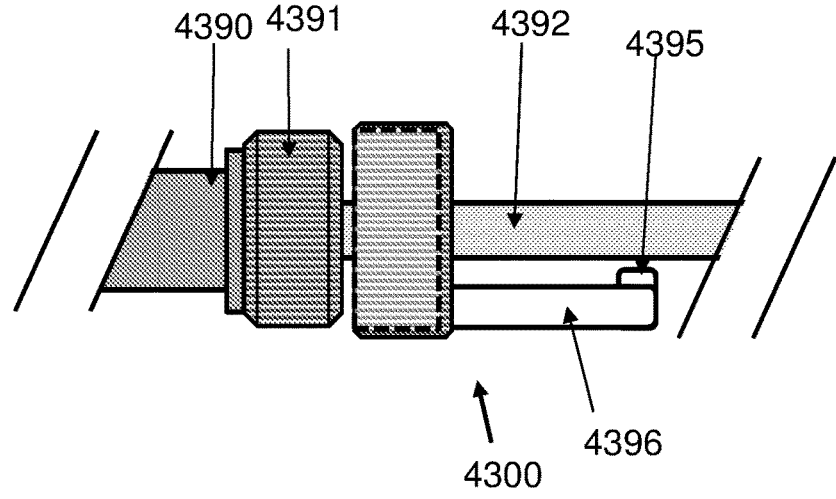
FIG. 43 illustrates a locking mechanism for fixing a catheter shaft to a hub of a sheath during therapy.

FIG. 43 illustrates a locking mechanism 4300 for fixing a catheter shaft 4392 to a hub 4391 of a sheath 4390 during therapy. The locking mechanism 4300 includes an arm 4396 with a catheter shaft grip 4395 attached to a distal end of the arm 4396. When engaged, the catheter shaft grip 4395 attaches to the catheter shaft 4392 preventing movement. The locking mechanism 4300 is advantageous because it prevents migration of a distal expandable member of the catheter system, described above, during therapy. The locking mechanism 4300 is configured to lock the catheter shaft 4392 to the sheath 4390 during at least a portion of the procedure.

The locking mechanism 4300 may be configured for easy engagement and disengagement. The locking mechanism may be configured to prevent relative movement between the catheter distal balloon and the access sheath 4390. The locking mechanism 4300 may comprise a clip 4395 on locking mechanism 4300; the clip on mechanism 4300 may be configured to be clipped onto the catheter shaft 4392 from one side of the shaft 4392. The locking mechanism 4300 may be pre-mounted on the catheter shaft 4392 such that the locking mechanism 4300 may slide into position when fixation is required.

The locking mechanism may be integral with the sheath. The locking mechanism may optionally attach to the sheath. Preferably, the locking mechanism may be a Tuohy Borst type locking mechanism.

Figure 44:
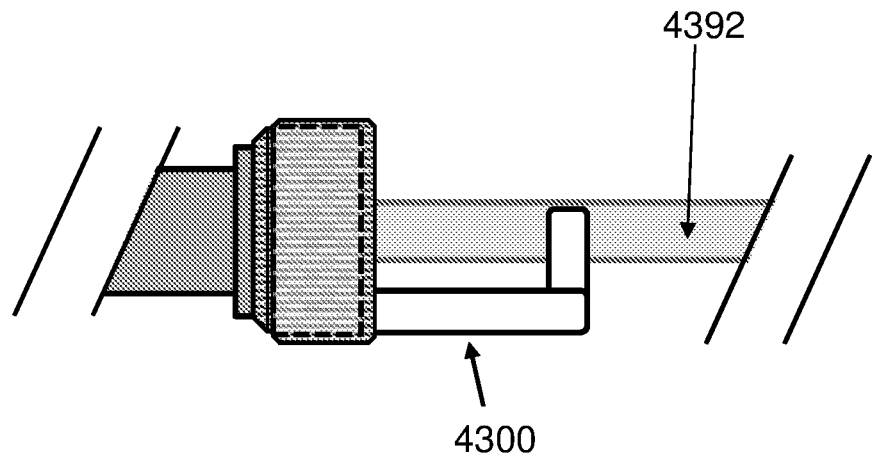
FIG. 44 shows the locking mechanism engaged with the catheter shaft.

FIG. 44 shows the locking mechanism 4300 engaged with the catheter shaft.

Figure 45:
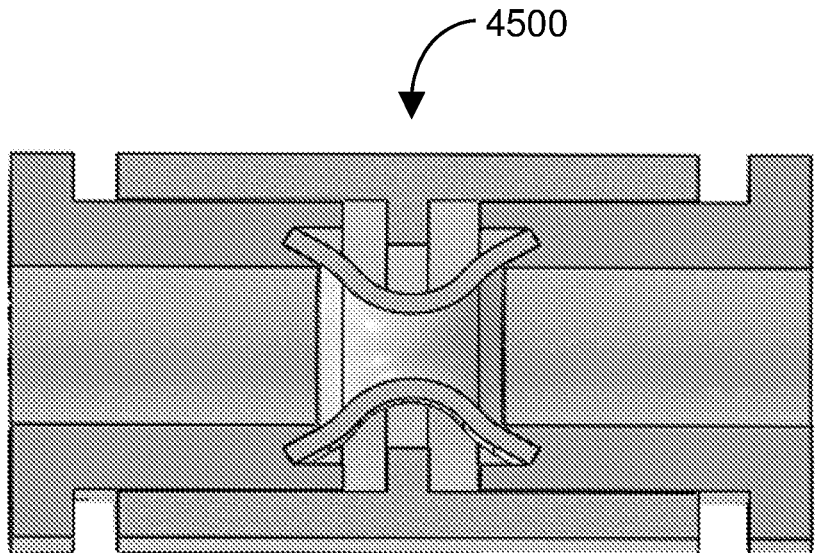
FIG. 45 shows a schematic of a push lock mechanism.

FIG. 45 shows a schematic of a push lock mechanism 4500.

Figure 46:
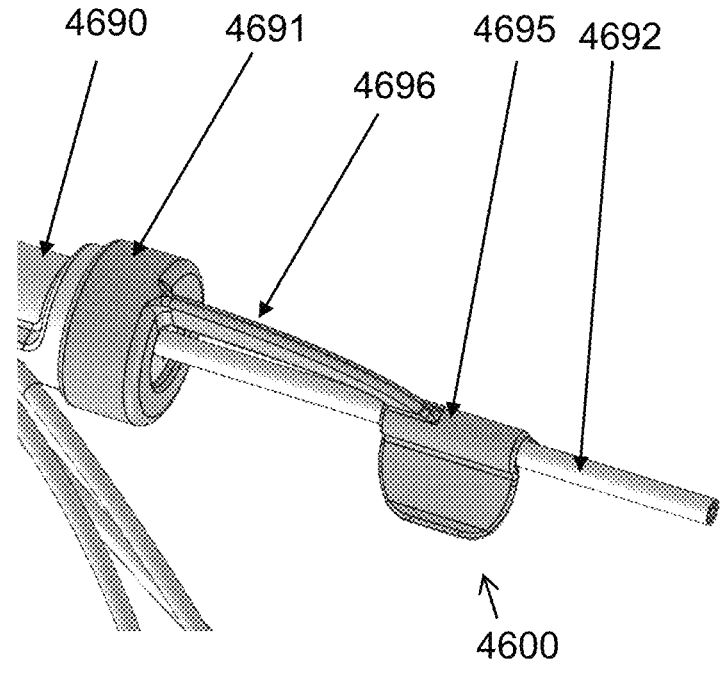
FIG. 46 shows an alternative locking mechanism.

FIG. 46 shows an alternative locking mechanism 4600. The locking mechanism 4600 includes an arm 4696 attached to a hub 4691 of a sheath 4690. The arm 4696 includes a catheter shaft grip 4695 attached to a distal end of the arm 4696. When engaged, the catheter shaft grip 4695 attaches to the catheter shaft 4692 preventing movement. A further embodiment of a locking system may include a C shaped shaft which may be secured over the catheter shaft proximal to the sheath. The shaft would be configured so that when the shaft is slid into the sheath hub it creates an interference lock between the catheter shaft OD and Sheath ID.

Figure 47:
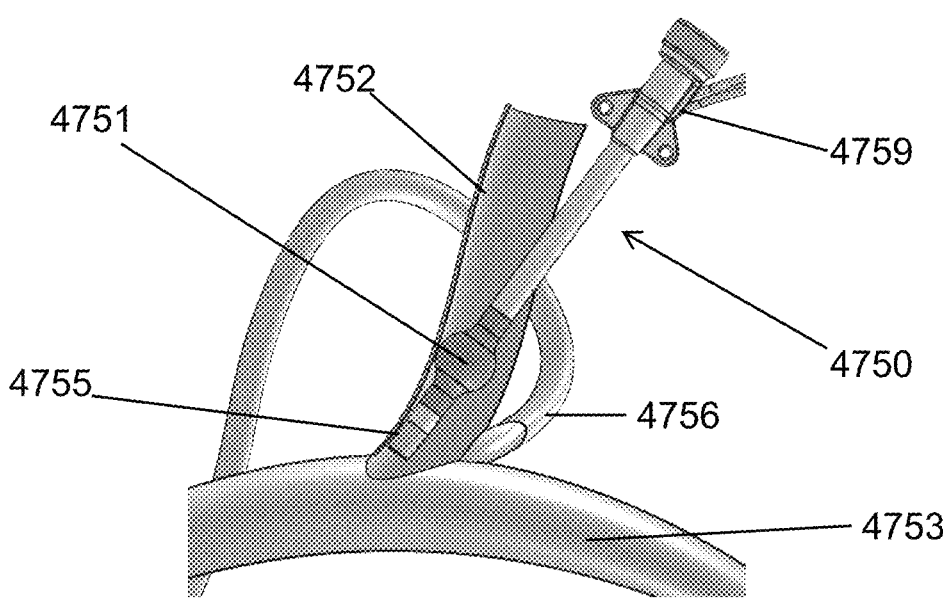
FIG. 47 is a partial cutaway of a jugular vein showing a flow control sheath inserted therein.

FIG. 47 is a partial cutaway of a jugular vein 4752 showing a flow control sheath 4750 inserted therein. The restrictor 4751 of the sheath 4750 is shown in a deployed state with the restrictor 4751 opposing a wall of the jugular vein 4752. In a preferred position, the shaft 4755 of the sheath 4750 terminates adjacent to a junction of the subclavian vein 4753 and the thoracic duct 4756. The hub 4759 is external to the jugular vein 4752.

Figure 48:
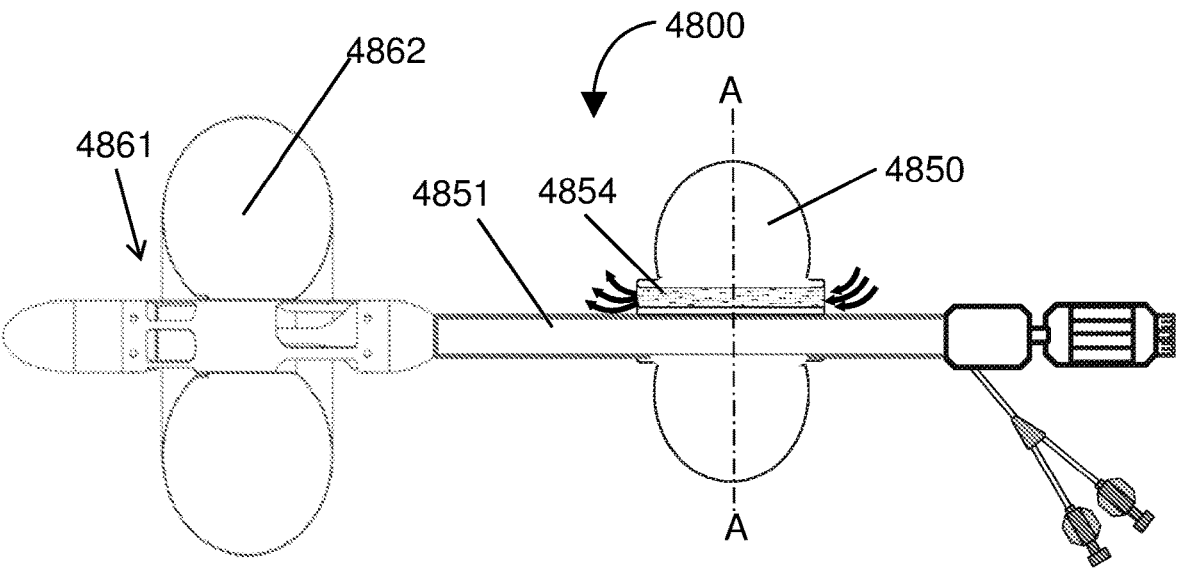
FIG. 48 shows an indwelling catheter system.

FIG. 48 shows an indwelling catheter system 4800 according to aspects of the invention. The indwelling catheter system 4800 includes a catheter shaft 4851 with an impeller assembly 4861 mounted to a distal portion thereof. The catheter shaft 4851 includes a proximal expandable member 4850 attached to an outer surface of the catheter shaft 4851. The proximal expandable member 4850 comprises a flow channel 4854 that allows fluid to bypass the proximal expandable member 4850 at a controllable rate.

Figure 49:
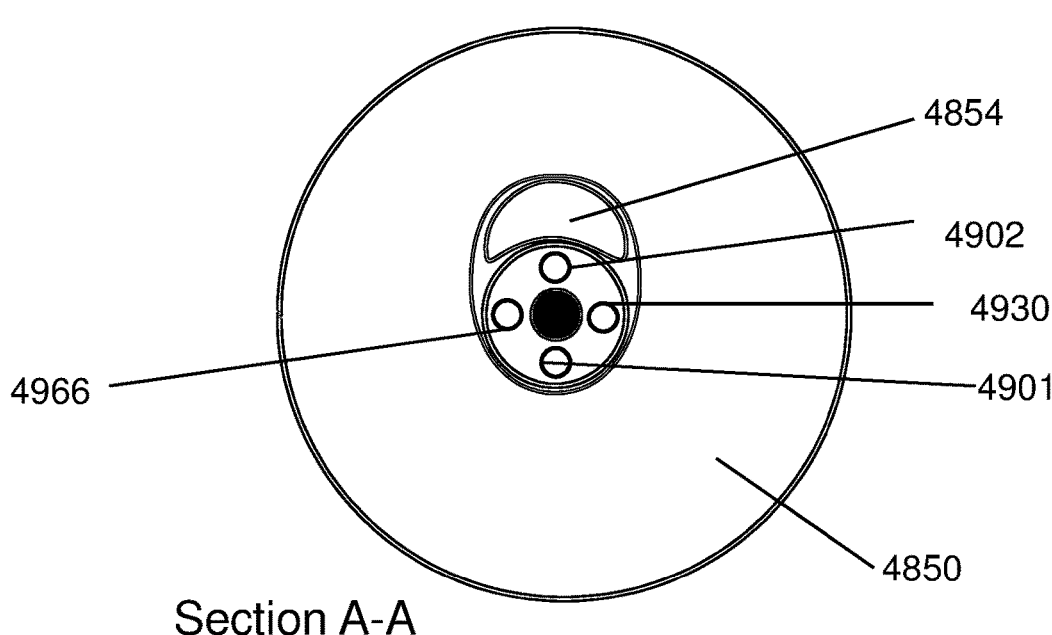
FIG. 49 is a cross-section taken along line A-A of FIG. 48.

FIG. 49 is a cross-section taken along line A-A of FIG. 48 to reveal internal lumens of the catheter shaft 4851. The internal lumens extend internally through the catheter shaft 4851. Shown is a proximal expandable member lumen 4901 for delivering fluids, i.e., gas or a liquid, used to inflate the proximal expandable member 4850. A separate distal expandable member lumen 4902 is provided for delivering fluids to inflate the distal expandable member 4862. The separate lumens allow the proximal and distal expandable members 4850, 4862 to be manipulated independently of one another during therapeutic treatments. A pressure sensor lumen 4966 is provided for sending and receiving electrical signals with one or more pressure sensors disposed on the catheter system 4800. One or more reinforcement lumens 4930 may be provided to reinforce the catheter 4800 so that the catheter 4800 can be more easily navigated through the body.

Figure 50:
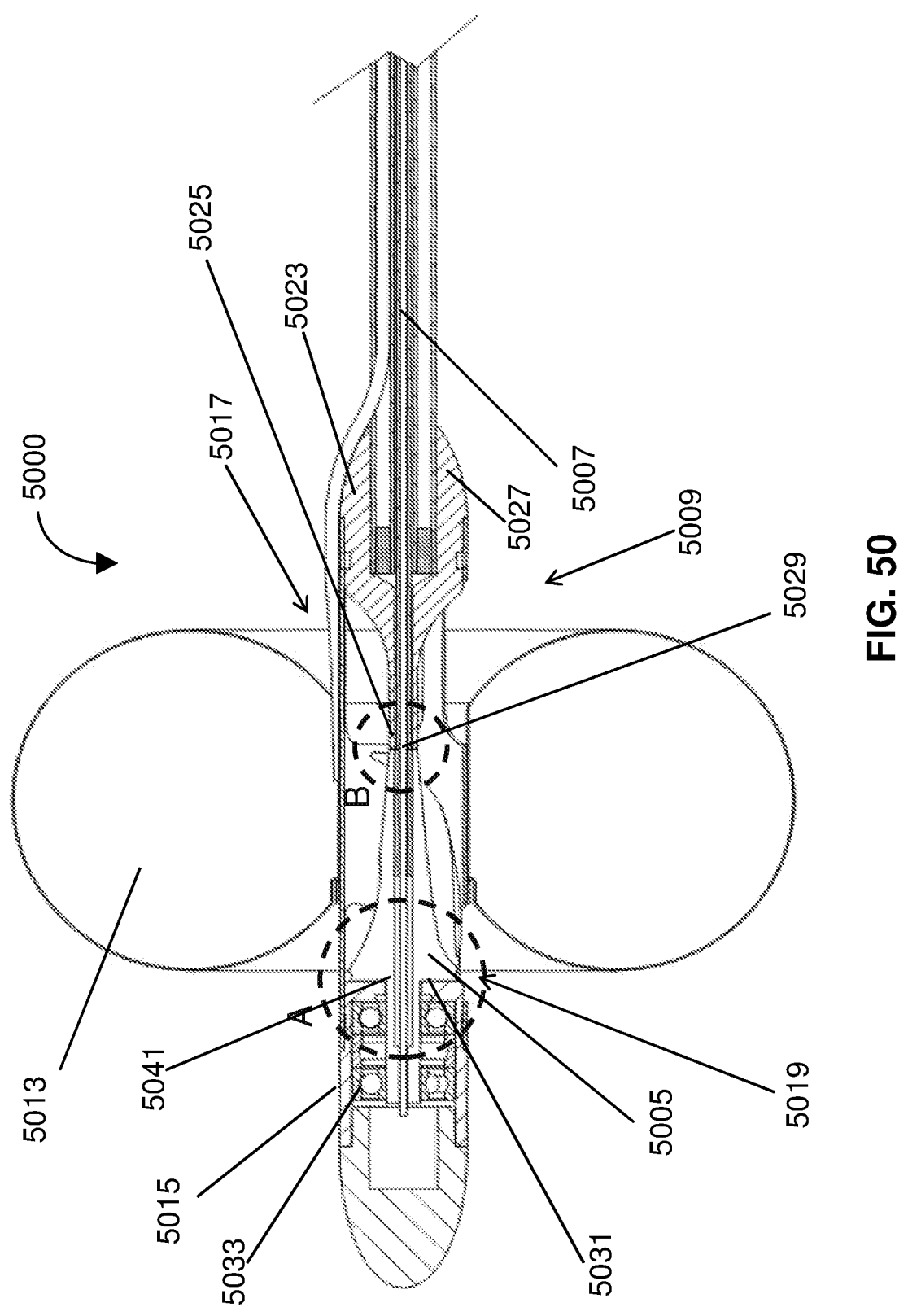
FIG. 50 is an indwelling catheter.

FIG. 50 is an indwelling catheter 5000. The catheter 5000 includes mechanical components, e.g., an impeller 5005 and/or drive shaft 5007, and a purge system. The purge system operates to exclude biological fluids and materials from the catheter 5000 and mechanical components operating within the catheter 5000. In that manner, body fluids are prevented from entering the crevasses of the catheter 5000, ensuring smooth and efficient operation of the mechanical parts, e.g., impeller 5005 and drive shaft 5007, within the catheter 5000 while also preventing the patient's body fluid from travelling to a proximal portion of the catheter 5000 outside of the patient's body, where it could leak out of the catheter. The purge system would further prevent air entering the vein though the same channels.

The catheter 5000 may be used to reduce pressure in a region of a venous system. The catheter 5000 includes an impellor assembly 5009 mounted at the distal end of the catheter 5000. The impellor assembly 5009 comprises an expandable member 5013, a cage 5015 with an inlet region 5017 and an outlet region 5019 and an impellor therein. The impellor 5005 may rotate at high RPMs within the cage 5015. The impellor 5005 may further include a distal surface, a proximal surface and an impellor blade surface. The distal surface, proximal surface and impeller blade surface configured to rotate in close proximity to adjacent surfaces inside the cage, but without contacting said adjacent surfaces.

The impellor assembly 5009 may further comprise a cuff 5023. The cuff 5023 may include a distal surface 5025 and a proximal surface 5027. The impeller 5005 rotates in clearance of the distal surface of a cuff 5023.

The clearance between the cuff distal surface 5025 and the impeller 5005 comprises a proximal gap 5029 and the proximal gap 5029 is configured to remain fixed during operation. The proximal gap 5029 is configured to define a transition between a static cuff and a rotating impeller 5005. The proximal gap 5029 is configured to allow blood to flow across the proximal gap 5029 without flow disturbance, flow recirculation, or vortices. The proximal gap 5029 may be in fluid communication with a catheter lumen which is in fluid communication with a fluid reservoir exterior of the patient. The proximal gap 5029 may be configured to prevent blood flow from entering the proximal gap 5029.

In preferred embodiments, the proximal gap 5029 includes a resistive fluid pressure configured to prevent blood from entering the proximal gap. For example, the resistive fluid may be a purge fluid delivered from a fluid reservoir external to the patient. The purge fluid can be used to purge or flush the proximal gap 5029 clearing debris; for example, as described in co-owned U.S. Provision Application 62/629,914, which is incorporated herein by reference. The resistive fluid pressure may comprise a hydrostatic fluid pressure, which may include a pulse of fluid pressure. The fluid pressure comprises a solution that may include saline, dextrose or a heparin solution.

The viscosity of the purge solution may be tailored to effectively purge small gaps and orifices. The solution may also be immiscible with blood to prevent blood contact with the purges surfaces. For example, the solution may be a hydrophobic solution. In some embodiments, the proximal gap 5029 may include a seal, such as, for example, a spring loaded seal.

A clearance between a distal-most surface of the impellor 5005 and a tip 5031 comprising a bearing housing 5033 may comprise a distal gap 5041 and the distal gap 5041 may be configured to remain fixed during operation. The distal gap 5041 may be configured to define a transition between a rotating impeller 5005 and a static tip 5031. The distal gap 5041 may be configured to allow blood to flow across the distal gap without flow disturbance, recirculation, or vortices.

In preferred embodiments, the distal gap 5041 is in fluid communication with a catheter lumen which is in fluid communication with a fluid reservoir exterior of the patient. The distal gap 5041 may be configured to prevent blood flow from entering the distal gap, for example, by providing a purge from the fluid reservoir as discussed above. The distal gap 5041 may comprise a resistive fluid pressure configured to prevent blood from entering the distal gap. The resistive fluid pressure comprises a hydrostatic fluid pressure. The resistive fluid pressure comprises a pulse of fluid pressure. The fluid pressure comprises a solution, for example, a saline, dextrose or a heparin solution. The viscosity of the purge solution may be tailored to effectively purge small gaps and orifices. The solution may also be immiscible with blood to prevent blood contact with the purges surfaces. The solution may be a hydrophobic solution. The distal gap 5041 may comprise a seal, such as, for example, a spring loaded seal.

Figure 51:
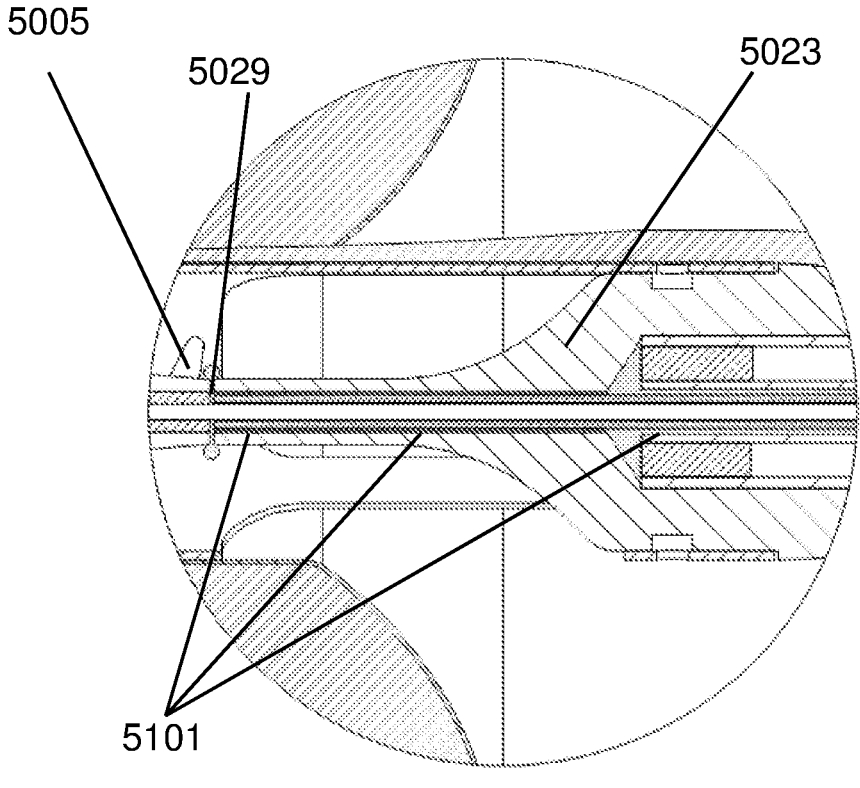
FIG. 51 is an expanded view of dotted circle B of FIG. 50 according to an embodiment of the invention.

FIG. 51 is an expanded view of dotted circle B of FIG. 50 according to an embodiment of the invention. In this embodiment, fluid is delivered from a purge channel 5101 extending along a central lumen of the device. The purge channel may be external to a PTFE liner that surrounds a central lumen of the catheter.

Figure 52:
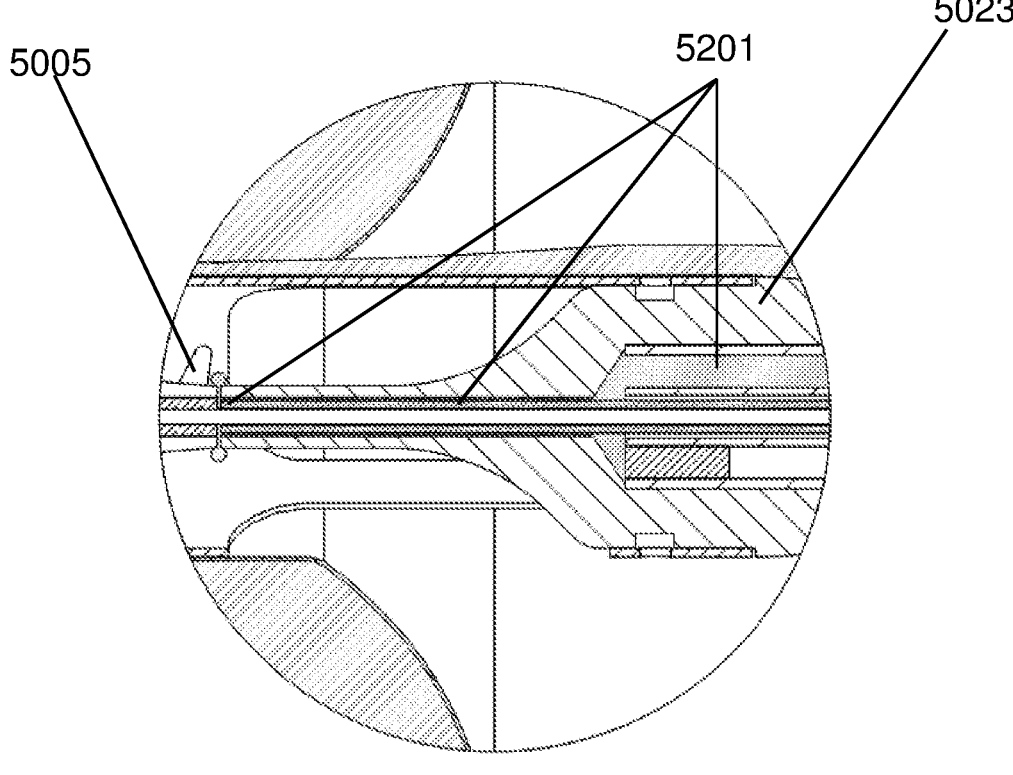
FIG. 52 is an expanded view of dotted circle B of FIG. 50 according to another embodiment of the invention.

FIG. 52 is an expanded view of dotted circle B of FIG. 50 according to another embodiment of the invention. In this embodiment, purge fluid is delivered from the reservoir exterior of the patient via a purge channel 5201 that travels through a lumen used for inflating the expandable member 5013. The purge channel 5201 is external to a PTFE liner of a drive cable.

Figure 53:
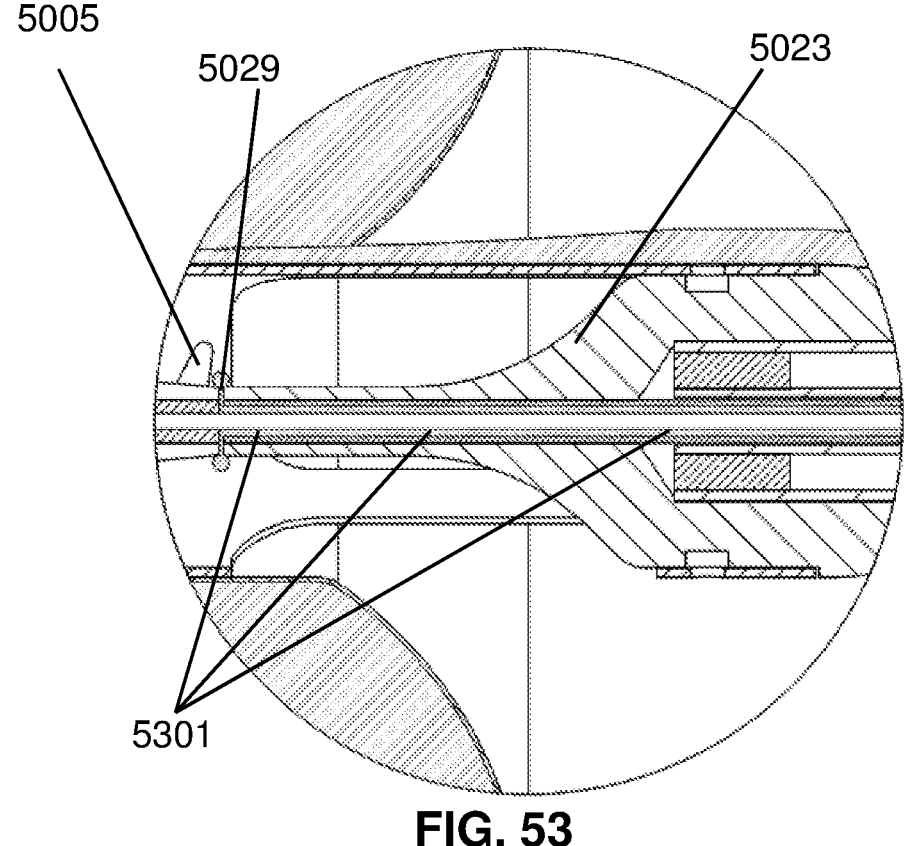
FIG. 53 is an expanded view of dotted circle B of FIG. 50 according to a different embodiment of the invention.

FIG. 53 is an expanded view of dotted circle B of FIG. 50 according to a different embodiment of the invention. In this embodiment, purge fluid is delivered from a purge channel 5301, the purge channel 5301 extending through a PTFE liner that surrounds a drive lumen.

Figure 54:
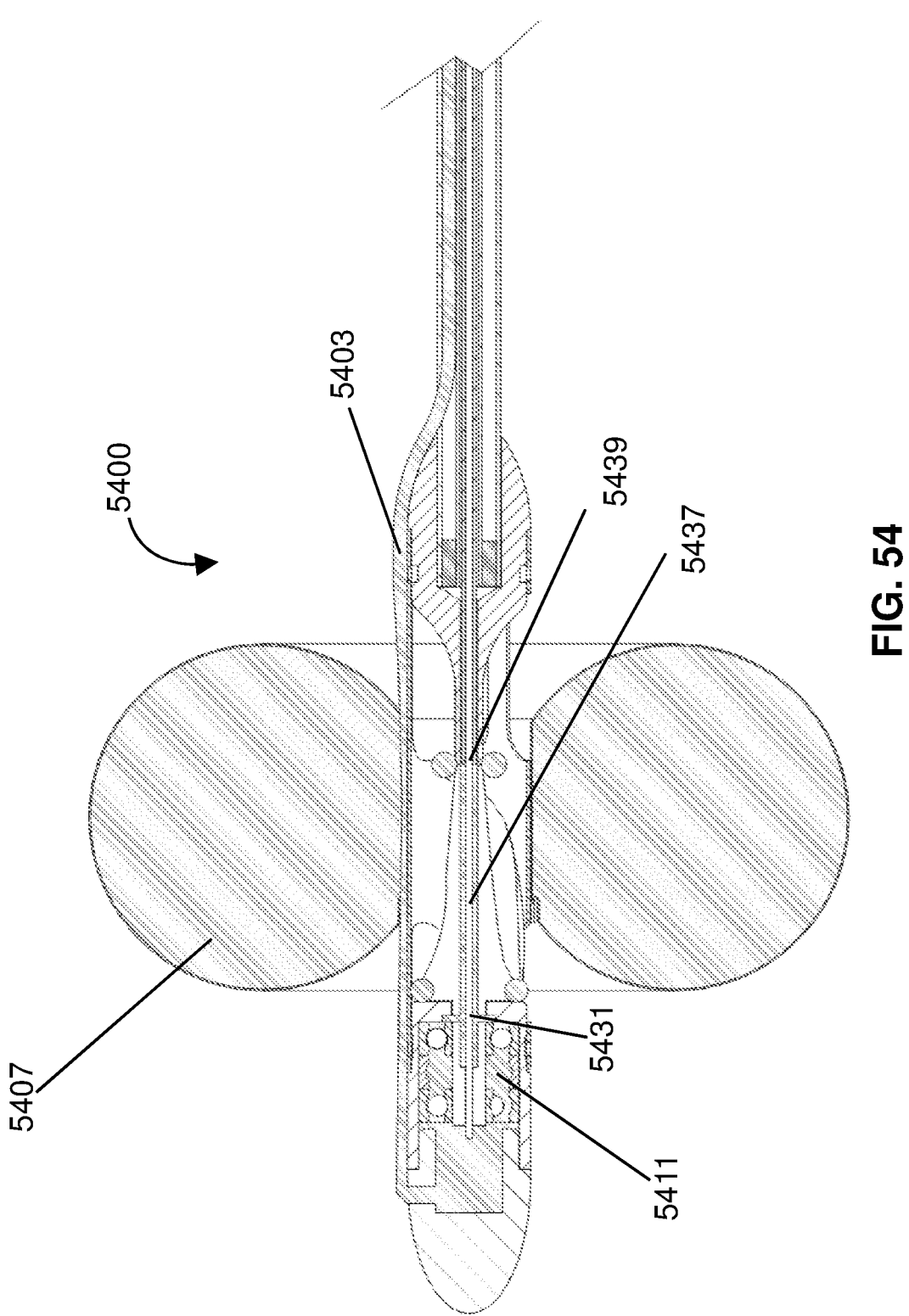
FIG. 54 illustrates a distal flush of an indwelling catheter.

FIG. 54 illustrates a distal flush of an indwelling catheter 5400. The flush, i.e., purge fluid, is delivered via a lumen 5403 of the expandable member 5407. The purge travels through the lumen 5403 and through a distal bearing housing 5411, preventing blood flood flow into bearings of the catheter. The purge fluid flows into the distal gap 5431 flushing and preventing blood from filling the distal gap 5431. The purge fluid travels down a second lumen 5437 to a proximal gap 5439 and flushes blood from the proximal gap 5439.

Figure 55:
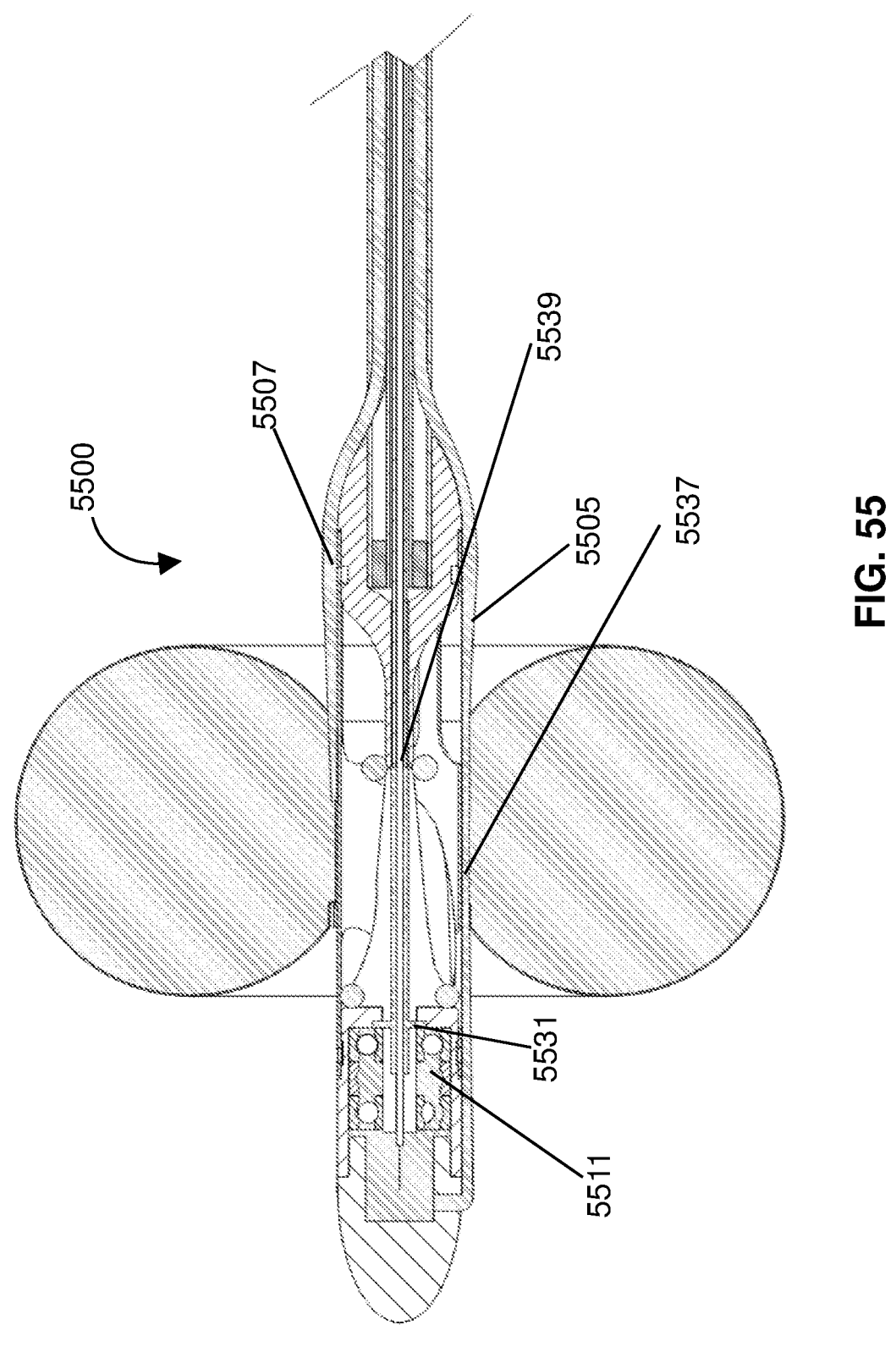
FIG. 55 illustrates distal flush of an indwelling catheter according to a different embodiment.

FIG. 55 illustrates distal flush of an indwelling catheter 5500 according to a different embodiment. In this embodiment, the purge fluid is delivered via a purge lumen 5505 that is separate and distinct of the lumen for inflating the expandable member 5507. The purge travels through the purge lumen 5505 and into a distal bearing housing 5511, thereby preventing blood flood flow into bearings of the catheter. The purge fluid flows into the distal gap 5531 flushing and preventing blood from filling the distal gap 5531. The purge fluid then travels down a second lumen 5537 to a proximal gap 5539 to flush blood from the proximal gap 5539.

Figures 56, 57:
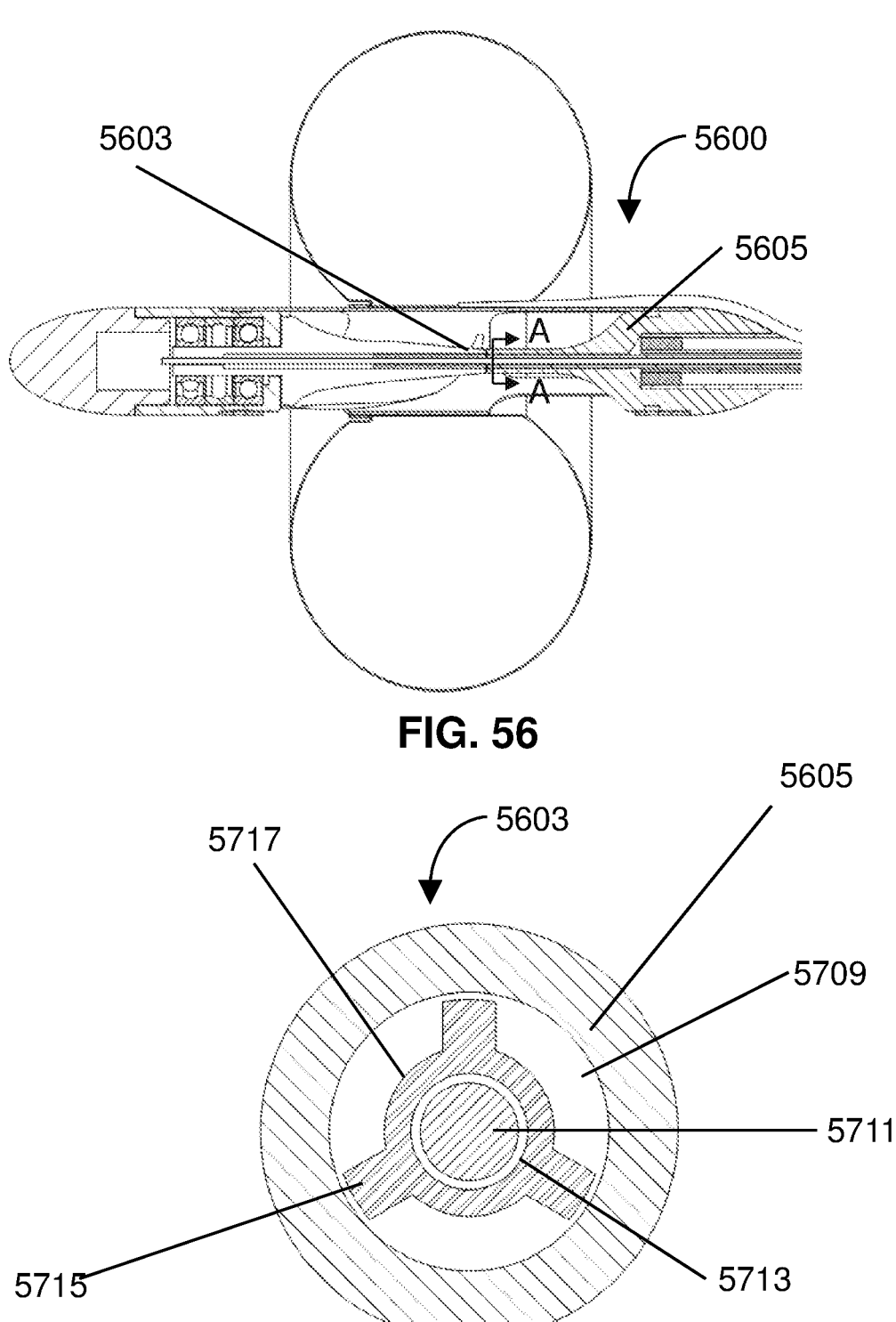
FIG. 56 shows an indwelling catheter with a purge system.
FIG. 57 shows a cross-section of the central lumen taken along line A-A of FIG. 56 according to one embodiment of the invention.

FIG. 56 shows an indwelling catheter 5600 with a purge system. The catheter 5600 includes a central lumen 5603 optimized for transporting purge fluid and maintaining concentricity of the catheter 5600 assembly. The internal structures of the central lumen 5306 can have various configurations some of which are detailed below in cross-sections taken through a cuff 5606 along line A-A.

FIG. 57 shows a cross-section of the central lumen 5603 taken along line A-A of FIG. 56 according to one embodiment of the invention. In this embodiment, a purge channel 5709 is external to a drive shaft 5711 that connects a motor to an impeller of the device. Between the purge channel and the drive shaft 5711 is a profiled extrusion 5713. The profiled extrusion 5713 includes a number of projections 5715, for example, at least two projections 5715, and preferably three projections 5715, the projections 5715 extend outward from a central hub 5717 that encases the drive shaft 5711. The profiled extrusion 5713 optimizes a purge cross sectional area and also helps to maintain assembly concentricity.

Figure 58:
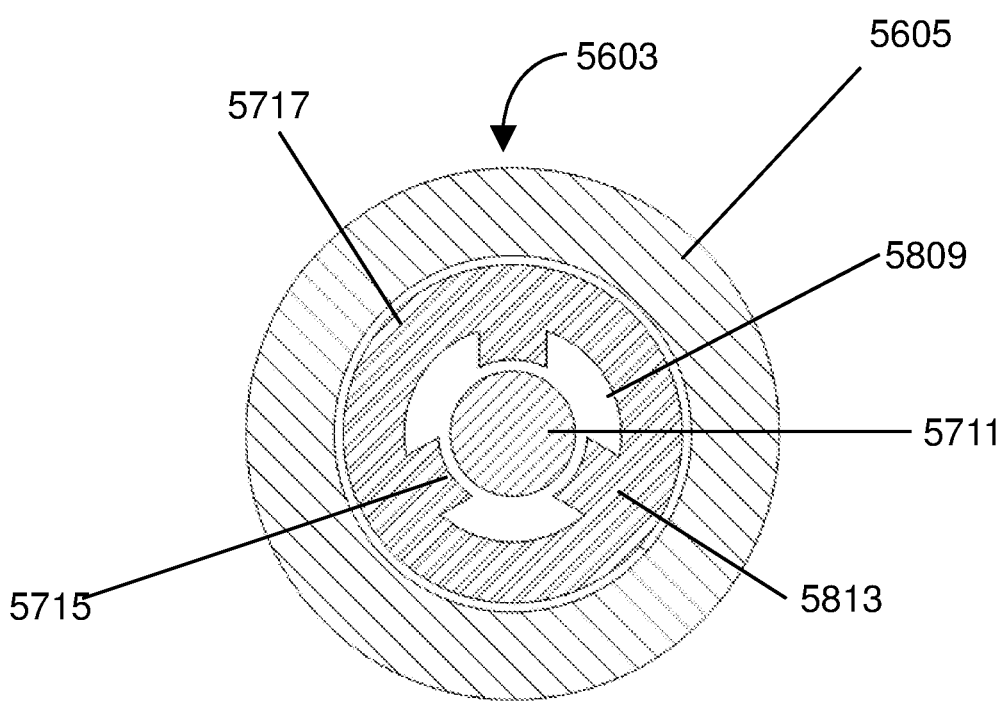
FIG. 58 shows a cross-section of the central lumen taken along line A-A of FIG. 56 according to a different embodiment of the invention.

FIG. 58 shows a cross-section of the central lumen 5603 taken along line A-A of FIG. 56 according to a different embodiment of the invention. In this embodiment, a purge channel 5809 is in association with the drive shaft 5711 connecting the motor to the impeller of the device. The purge channel 5809 is defined by a profiled extrusion 5813. The profiled extrusion 5813 includes a number of projections 5815, for example, at least two projections 5815, and preferably three projections 5815, the projections 5815 extending inward from an outer hub 5817 that encases the drive shaft 5711. The profiled extrusion 5813 defines and optimizes a purge cross-sectional area and maintains assembly concentricity.

Figure 59:
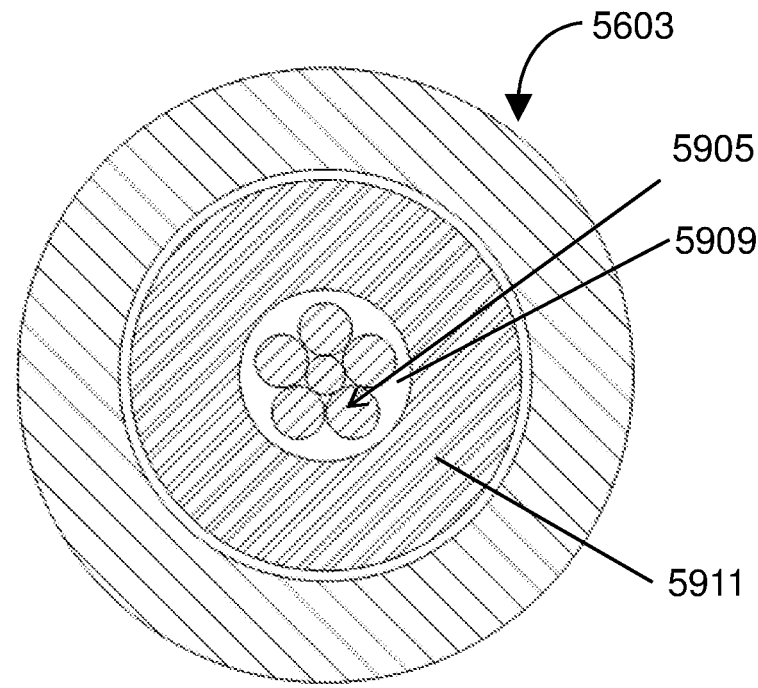
FIG. 59 shows a cross-section of the central lumen taken along line A-A of FIG. 56 according to another embodiment of the invention.

FIG. 59 shows a cross-section of the central lumen 5603 taken along line A-A of FIG. 56 according to another embodiment of the invention. In this embodiment, the central lumen 5603 houses a coil drive shaft 5905 connecting the motor to the impeller of the device. A purge channel 5909 surrounds the coil drive shaft 5905. The purge channel 5909 is defined by an outer hub 5911 that encases the coil drive shaft 5905.

Figures 60, 61:
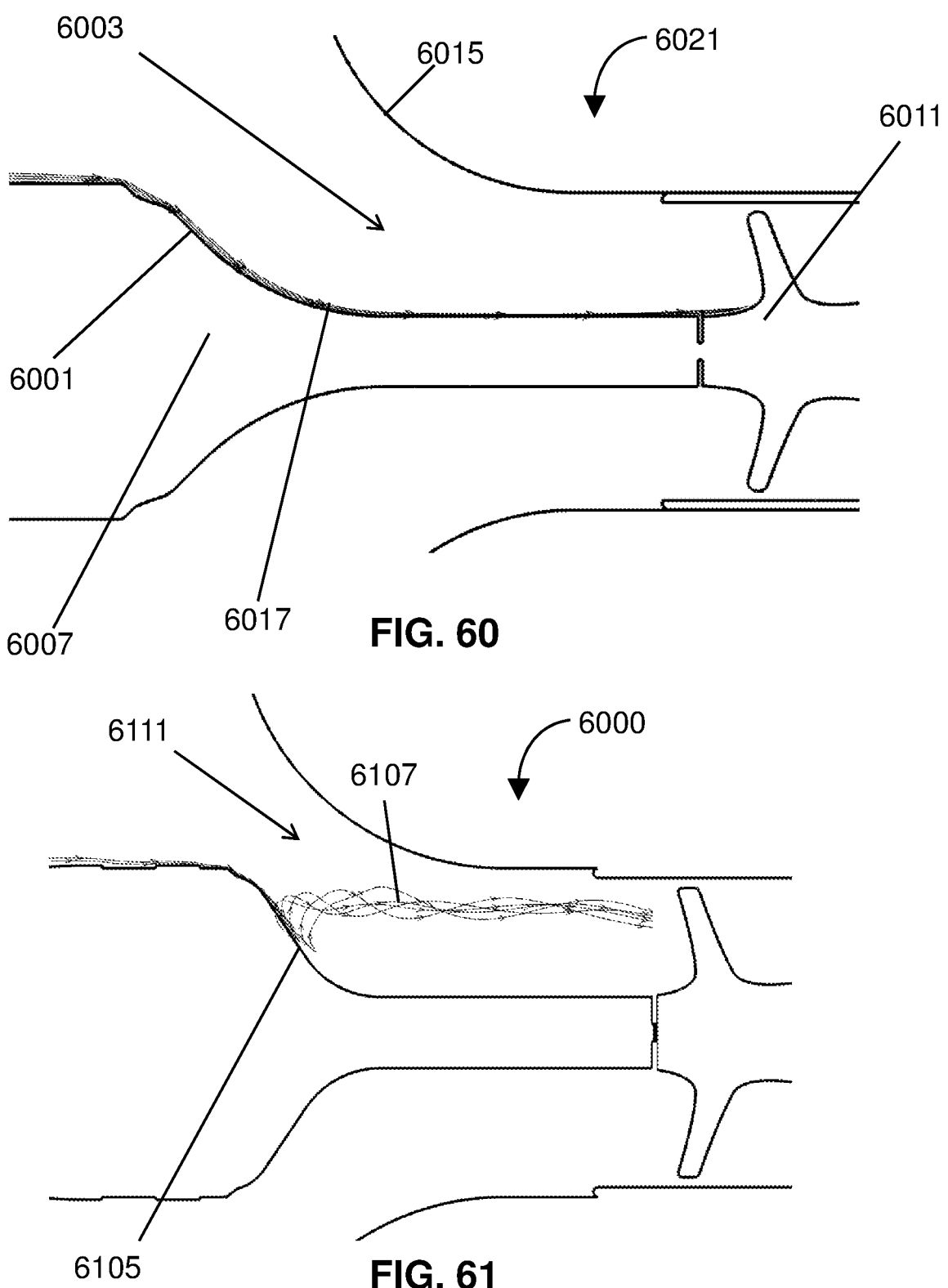
FIG. 60 shows an optimized guide surface of a cage inlet.
FIG. 61 shows a suboptimal guide surface.

FIG. 60 shows an optimized guide surface 6001 of a cage inlet 6003. With reference to FIG. 27, the optimized guide surface 6001 comprises a portion of a cuff 6007 that tapers towards the impeller 6011 in harmony with an outer boundary surface 6015. The optimized guide surface 6001 maintains axial momentum and prevents recirculation of fluid 6017 flowing into the cage assembly 6021. In particular, the optimized guide surface 6001 tapers in a manner that creates a flow field convergence and minimizes fluid divergence in the inlet region 6003. The optimized guide surface 6001 may comprise a curved tapered section. The optimized guide surface 6001 may be configured to smoothly reduce the cross sectional area along the length of the inlet 6003. For example, the change in cross sectional area of the optimized guide surface 6001 along the length of the inlet 6003 may be less than or equal to about 1 mm$^2$. The optimized guide surface 6001 may comprise a curved taper. The optimized guide surface 6001 may comprises a cylindrical section. The optimized guide surface 6001 may comprise a substantially conical section.

In some embodiments, the outer boundary surface 6015 tapers over at least a portion of the inlet region 6003. With reference to FIG. 17, the outer boundary surface 6015 may comprise a proximal surface of an expandable member. Alternatively, the outer boundary surface 6015 may comprise an inner surface of the cage.

FIG. 61 shows a suboptimal guide surface 6105. The suboptimal guide surface 6105 may cause disturbances in flow 6107 of fluid flowing into the inlet region 6111. In particular, the suboptimal guide surface 6105 comprises a steeper profile as compared to the optimized guide surface 6017 of FIG. 60. The steeper profile causes changes in axial momentum and fluid divergence of blood flowing into the inlet region 6111. These disturbances in flow 6107 are prevented by with the optimized guide surface 6017.

Figures 62, 63:
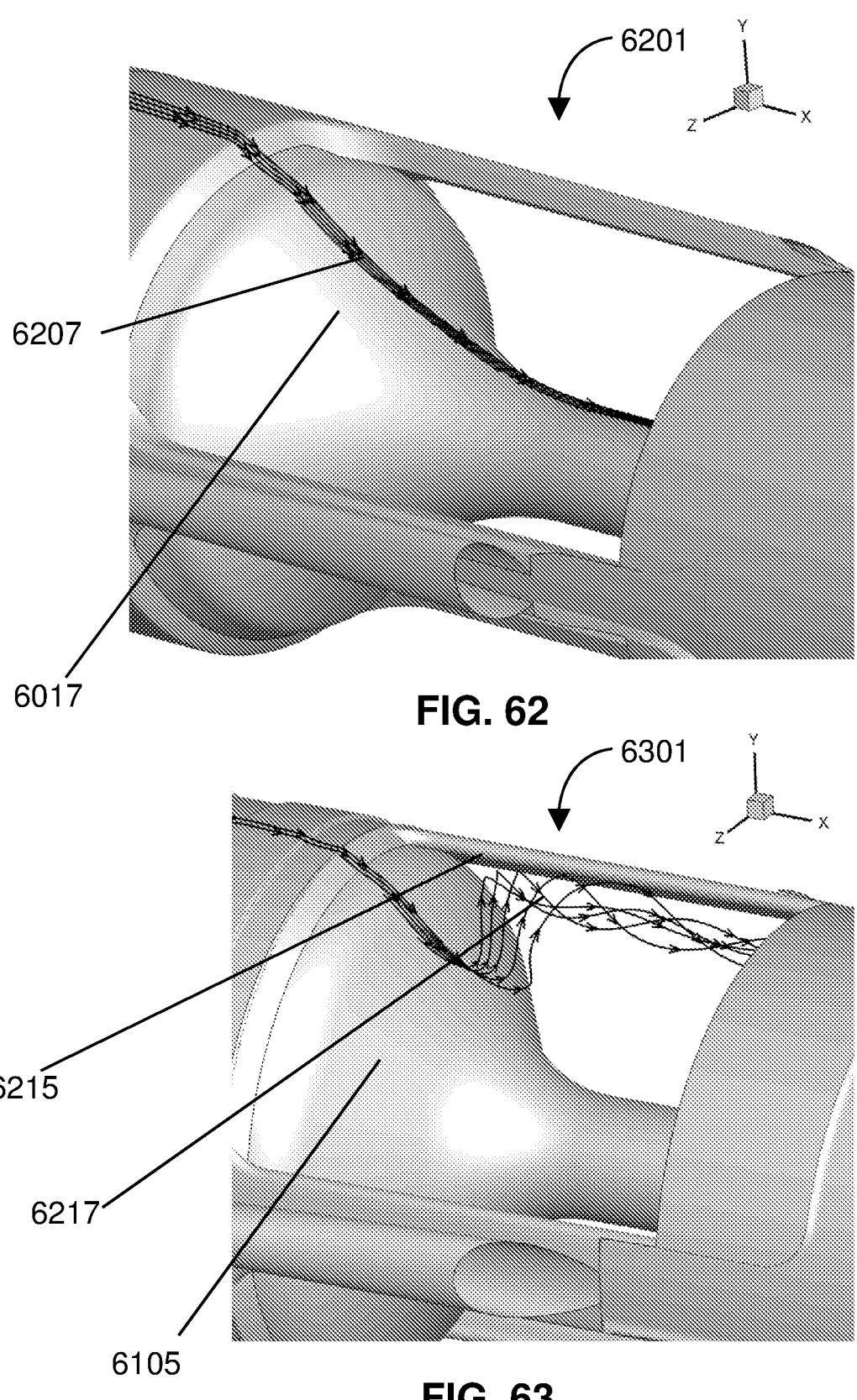
FIG. 62 shows a cage inlet.
FIG. 63 shows a suboptimal inlet configuration.

FIG. 62 shows a cage inlet 6201. Illustrated is an optimal configuration where fluid flow 6207 is aligned with the inlet 6201 along an optimized guiding surface 6017. The flow 6207 is primarily in the X-direction with no rotational component which promotes a smoothly flowing inlet 6201.

FIG. 63 shows a suboptimal inlet 6301 configuration. This suboptimal configuration includes a steep guide surface 6105 that causes recirculation and stalls the flow in the inlet. A rotational component of the velocity dominates and carries the flow underneath the inlet struts 6215. This phenomenon creates disrupted flow 6217 in the inlet 6301 and reduces the effectiveness of the inlet 6301 to guide flow towards the impeller.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device comprising:

a catheter comprising a proximal portion and a distal portion;

a cap secured to the distal portion;

one or more struts extending distally from the cap; and an impeller housing attached to distal ends of the one or more struts, the impeller housing comprising an impeller assembly with an impeller operably disposed within the impeller assembly and one or more outlets positioned at a distal portion of the impeller housing, wherein the impeller housing, the cap, and the one or more struts define an inlet region comprising a proximal end and a distal end, the inlet region positioned at a proximal portion of the impeller housing and configured to direct flow into the impeller housing, wherein the cap comprises a tapered guide surface extending distally from the distal end of the catheter into the inlet region, wherein the inlet region has a tapered surface and tapers towards the impeller such that fluid flow in the inlet region and into the impeller housing is aligned with the guide surface to thereby provide a continuously converging fluid flow pattern between the two tapered surfaces from the inlet proximal region to the inlet distal region configured to direct fluid flow into the impeller housing without recirculation.

2. The device of claim 1, further comprising an expandable member aligned over an exterior surface of the impeller housing, wherein an exterior surface of the expandable member is coupled to the exterior surface of the impeller housing, and wherein, when the expandable member is in an expanded state, the expandable member directs fluid flow to the inlet region of the impeller housing, wherein, when in the expanded state, a proximal face of the expandable member is substantially aligned with a distal portion of the inlet region.

3. The device of claim 2, wherein the expandable member comprises a fluidically sealed inflation space that is radially expandable relative to the impeller housing.

4. The device of claim 3, wherein the impeller assembly comprises an inflation tube connecting the inflation space to a lumen of the catheter, wherein the inflation tube extends, exterior of the proximal strut, between the catheter and the inflation space.

5. The device of claim 4, wherein the inflation space comprises an inflation port for expanding the expandable member.

6. The device of claim 1, wherein operation of the impeller within a blood vessel drives blood into the impeller assembly via the inlet region and out of the impeller assembly via the one or more outlets.

7. A method for treating edema, the method comprising: providing a device comprising:

a catheter comprising a proximal portion and a distal portion;

a cap secured to the distal portion;

one or more struts extending distally from the cap; and an impeller housing attached to distal ends of the one or more struts, the impeller housing comprising an impeller assembly with an impeller operably disposed within the impeller assembly and one or more outlets positioned at a distal portion of the impeller housing, wherein the impeller housing, the cap, and the one or more struts define an inlet region comprising a proximal end and a distal end, the inlet region positioned at a proximal portion of the impeller housing and configured to direct flow into the impeller housing, wherein the cap comprises a tapered guide surface extending distally from the distal end of the catheter into the inlet region, wherein the inlet region has a tapered surface and tapers towards the impeller such that fluid flow in the inlet region and into the impeller housing is aligned with the guide surface to thereby provide a continuously converging fluid flow pattern between the two tapered surfaces from the inlet proximal region to the inlet distal region configured to direct fluid flow into the impeller housing without recirculation; and operating the impeller to thereby decrease pressure at a lymphatic duct.

8. The method of claim 7, wherein the device further comprises an expandable member aligned over an exterior surface of the impeller housing, wherein an exterior surface of the expandable member is coupled to the exterior surface of the impeller housing, wherein the method further comprises expanding the expandable member and wherein, when the expandable member is in an expanded state, a proximal face of the expandable member is substantially aligned with a distal portion of the inlet region and the expandable member directs fluid flow to the inlet region of the impeller housing.

9. The method of claim 8, wherein the expandable member comprises a fluidically sealed inflation space that is radially expandable relative to the impeller housing.

10. The method of claim 9, wherein the impeller assembly comprises an inflation tube connecting the inflation space to a lumen of the catheter, wherein the inflation tube extends, exterior of the proximal strut, between the catheter and the inflation space.

11. The method of claim 10, wherein the inflation space comprises an inflation port for expanding the expandable member.

12. The method of claim 7, wherein operation of the impeller within a blood vessel drives blood into the impeller assembly via the inlet region and out of the impeller assembly via the one or more outlets.

* * * * *